US009085623B2

(12) United States Patent
Rother et al.

(10) Patent No.: US 9,085,623 B2
(45) Date of Patent: Jul. 21, 2015

(54) THERAPEUTIC METHODS USING ANTI-CD200 ANTIBODIES

(75) Inventors: Russell P. Rother, Oklahoma City, OK (US); Yan Yan, Cheshire, CT (US)

(73) Assignee: Alexion Pharmaceuticals, Inc., Cheshire, CT (US)

( * ) Notice: Subject to any disclaimer, the term of this patent is extended or adjusted under 35 U.S.C. 154(b) by 40 days.

(21) Appl. No.: 13/578,367

(22) PCT Filed: Feb. 11, 2011
(Under 37 CFR 1.47)

(86) PCT No.: PCT/US2011/024511
§ 371 (c)(1),
(2), (4) Date: Jan. 18, 2013

(87) PCT Pub. No.: WO2011/100538
PCT Pub. Date: Aug. 18, 2011

(65) Prior Publication Data
US 2013/0189258 A1 Jul. 25, 2013

Related U.S. Application Data

(60) Provisional application No. 61/337,962, filed on Feb. 11, 2010.

(51) Int. Cl.
C07K 16/28 (2006.01)
A61K 39/395 (2006.01)
A61K 39/00 (2006.01)

(52) U.S. Cl.
CPC ........ C07K 16/2803 (2013.01); A61K 39/39541 (2013.01); A61K 2039/505 (2013.01); C07K 2317/732 (2013.01)

(58) Field of Classification Search
None
See application file for complete search history.

(56) References Cited

U.S. PATENT DOCUMENTS

| | | | |
|---|---|---|---|
| 5,403,484 A | 4/1995 | Ladner et al. | |
| 5,595,721 A | 1/1997 | Kaminski et al. | |
| 6,338,851 B1 | 1/2002 | Gorczynski | |
| 6,652,858 B2 | 11/2003 | Gorczynski et al. | |
| 6,749,854 B2 | 6/2004 | Gorczynski et al. | |
| 6,955,811 B2 | 10/2005 | Gorczynski et al. | |
| 6,984,625 B2 | 1/2006 | Gorczynski | |
| 7,238,352 B2 | 7/2007 | Gorczynski et al. | |
| 7,368,535 B2 | 5/2008 | Gorczynski et al. | |
| 7,408,041 B2 | 8/2008 | Bowdish et al. | |
| 7,422,739 B2 | 9/2008 | Anderson et al. | |
| 7,435,412 B2 | 10/2008 | Bowdish et al. | |
| 7,435,803 B2 | 10/2008 | Hansen et al. | |
| 7,452,536 B2 | 11/2008 | Gorczynski et al. | |
| 7,887,798 B2 | 2/2011 | Gorczynski et al. | |
| 8,114,403 B2 * | 2/2012 | Bowdish et al. | 424/155.1 |
| 8,709,415 B2 * | 4/2014 | Bowdish et al. | 424/130.1 |
| 2002/0168364 A1 | 11/2002 | Gorczynski et al. | |
| 2002/0192215 A1 | 12/2002 | Hoek et al. | |
| 2004/0018972 A1 | 1/2004 | Gorczynski et al. | |
| 2004/0054145 A1 | 3/2004 | Gorczynski | |
| 2004/0175692 A1 | 9/2004 | Bowdish et al. | |
| 2004/0198661 A1 | 10/2004 | Bowdish et al. | |
| 2005/0048069 A1 | 3/2005 | Gorczynski et al. | |
| 2005/0074452 A1 * | 4/2005 | Bowdish et al. | 424/144.1 |
| 2005/0107314 A1 | 5/2005 | Gorczynski et al. | |
| 2005/0129690 A1 | 6/2005 | Bowdish et al. | |
| 2005/0169870 A1 | 8/2005 | Truitt et al. | |
| 2007/0036786 A1 | 2/2007 | Tuaillon et al. | |
| 2007/0065438 A1 | 3/2007 | Liversidge et al. | |
| 2007/0071675 A1 | 3/2007 | Wu et al. | |
| 2009/0053222 A1 * | 2/2009 | Gorczynski et al. | 424/133.1 |
| 2010/0267934 A1 * | 10/2010 | Van De Winkel et al. | 530/387.3 |

FOREIGN PATENT DOCUMENTS

| | | |
|---|---|---|
| JP | 2-46297 | 2/1990 |
| WO | 85/03508 A1 | 8/1985 |
| WO | 94/28027 A1 | 12/1994 |
| WO | 97/21450 A1 | 6/1997 |
| WO | 99/24565 A1 | 5/1999 |
| WO | 01/87336 A1 | 11/2001 |
| WO | 02/11762 A2 | 2/2002 |
| WO | 02/42332 A2 | 5/2002 |
| WO | 02/059280 A2 | 8/2002 |
| WO | 02/095030 A2 | 11/2002 |
| WO | 2004/060295 A2 | 7/2004 |
| WO | 2004/078938 A2 | 9/2004 |
| WO | WO 2006/020266 A2 | 2/2006 |
| WO | WO 2007/084321 A2 | 7/2007 |

(Continued)

OTHER PUBLICATIONS

Siva et al. (Cancer Immunol. Immunother. (2008) 57:987-996).*
Wright et al. (Immunology 2001 102 173-179).*
Moreaux et al. (Blood 2006;108:4194-4197).*
Kretz-Rommel et al. (J Immunol 2008; 180:699-705).*
Pallasch et al. (Leukemia Research 33 (2009) 460-464).*
Kawashima et al. (Lung Cancer 23 (1999) 67-70).*
Ohtaki et al. (Interactive CardioVascular and Thoracic Surgery 13 (2011) 220-222).*
Almefty et al. (J Neurosurg Pediatrics 12:251-257, 2013).*
Johnson et al. (British Journal of Cancer (2001) 85(11), 1619-1623).*
Maurer et al. (OncoImmunology 2012, 1:8, 1454-1456).*
Pankovik et al. (Vojnosanit Pregl. Nov. 2013;70(11):1010-4) (Abstract only).*
Raponi et al. (Leukemia & Lymphoma, Jun. 2011; 52(6): 1098-1107).*
Robak et al. (J Clin Oncol 2010, 28:1756-1765).*

(Continued)

Primary Examiner — Ilia Ouspenski
(74) Attorney, Agent, or Firm — Nelson Mullins Riley & Scarborough LLP; Jane E. Remillard, Esq.; Christopher L. Frank

(57) ABSTRACT

The present disclosure relates to anti-CD200 antibodies and to use of the antibodies in methods for treating autoimmune disorders and cancer. Also featured are biomarkers for use in selecting or prescribing a treatment modality for a patient with an autoimmune disorder and/or cancer. In addition, the disclosure features methods of treatment using an anti-CD200 antibody in combination with one or more additional therapeutic agents such as an anti-CD20 therapeutic agent.

11 Claims, 4 Drawing Sheets

(56) References Cited

FOREIGN PATENT DOCUMENTS

| WO | 2008/089022 A2 | 7/2008 |
| WO | WO 2009/014745 A1 | 1/2009 |

OTHER PUBLICATIONS

Tadashi et al. (Int J Clin Exp Pathol 2013;6(6):1177-1179).*
Coiffer et al. (Blood. Sep. 23, 2010; 116(12): 2040-2045).*
Palumbo et al. (Leukemia Research 33 (2009) 1212-1216).*
Hubert et al. (J Immunol 2004; 172:7485-7494).*
Rawstron et al. (Cytometry Part B 2010; 78B (Suppl. 1): S42-S46).*
Nathan, Carl et al., "Putting the brakes on innate immunity: a regulatory role for CD200?" Nature Immunology, vol. 2(1):17-19 (2001).
Ni, J. et al., "An immunoadhesin incorporating the molecule OX-2 is a potent immunosuppressant which prolongs allograft survival," FASEB Journal, vol. 13(5):A983, Poster Presentation 712.35 (1999).
Petermann, Kimberly B. et al., "CD200 is induced by ERK and is a potential therapeutic target in melanoma," The Journal of Clinical Investigation, vol. 117(12):3922-3929 (2007).
Preston, Sandy et al., "The leukocyte/neuron cell surface antigen OX2 binds to a ligand on macrophages," Eur. J. Immunol., vol. 27(8):1911-1918 (1997).
Ragheb, Rafik F.A. et al., "Exploration of OX-2 function in tolerance induction and graft acceptance using an anti-mouse OX-2 monoclonal antibody," Masters Abstracts International, vol. 38(4):971-972 (2000).
Ragheb, Rafik et al., "Preparation and functional properties of monoclonal antibodies to human, mouse and rat OX-2," Immunology Letters, vol. 68:311-315 (1999).
Reddy, N. M. et al., Rituximab resistance and its association with changes in the internal domain of CD20 antigen and down-regulation of pro-apoptotic protein Bax and Bak in both rituximab-resistant cell lines (Rrcl) and diffuse large B-cell lymphoma (DLBCL) patient (pt) samples, Journal of Clinical Oncology, 2006 ASCO Annual Meeting Proceedings, vol. 24(18S), Poster Presentation No. 17509 (2006).
Rijkers, Eva S.K. et al., "The inhibitory CD200R is differentially expressed on human and mouse T and B lymphocytes," Molecular Immunology, vol. 45:1126-1135 (2008).
Romagnani, Sergio et al., "Short Analytical Review, TH1 and TH2 in Human Diseases," Clinical Immunology and Immunopathology, vol. 80(3):225-235 (1996).
Rosenblum, Michael D. et al., "CD200 is a novel p53-target gene involved in apoptosis-associated immune tolerance," Blood, vol. 103(7):2691-2698 (2004).
Taylor, Neil et al., "Enhanced Tolerance to Autoimmune Uveitis in CD200-Deficient Mice Correlates wtih a Pronounced Th2 Switch in Response to Antigen Challenge," The Journal of Immunology, vol. 174:143-154 (2005).
Tedder, Thomas F. et al., "Isolation and structure of a cDNA encoding the B1 (CD20) cell-surface antigen of human B lymphocytes," Proc. Natl. Acad. Sci. USA, vol. 85:208-212 (1988).
Teeling, Jessica L. et al., "The Biological Activity of Human CD20 Monoclonal Antibodies Is Linked to Unique Epitopes on CD20," The Journal of Immunology, vol. 177:362-371 (2006).
Transplantation Tech., Inc. WO02095030, "Modulation of CD200 Receptors as a Novel Method of Immunosuppression," Expert Opin. Ther. Patents, vol. 13(5):711-715 (2003).
Wright, Gavin J. et al., "Lymphoid/Neuronal Cell Surface OX2 Glycoprotein Recognizes a Novel Receptor on Macrophages Implicated in the Control of Their Function," Immunity, vol. 13:233-242 (2000).
Wright, G.J. et al., "The lymphoid/neuronal OX-2 glycoprotein Interacts with a nove protein expressed by macrophages," Tissue Antigens, vol. 55(Suppl. 1):11, Poster Presentation A. 9 (2000).
Zhang, Shuli et al., "Molecular Mechanisms of CD200 Inhibition of Mast Cell Activation," The Journal of Immunology, vol. 173:6786-6793 (2004).
Long et al., "Antagonist anti-CD40 monoclonal antibody, CHIR-12.12, inhibits growth of a rituximab-resistant NHL xenograft model and achieves synergistic activity when combined with ineffective rituximab," retrieved from Biosis Database accession No. PRV200510271253, Database Biosis BioSciences Information Service (2004).
Supplementary European Search Report Application No. 11 74 2858, dated Jun. 12, 2013.
Almasri, Nidal M. et al., "Reduced Expression of CD20 Antigen as a Characteristic Marker for Chronic Lymphocytic Leukemia," American Journal of Hematology, vol. 40:259-263 (1992).
Banerjee, Debatri et al., "Blocking CD200-CD200 receptor axis augments NOS-2 expression and aggravates experimental autoimmune uveoretinitis in Lewis rats," Ocular Immunology and Inflammation, vol. 12(2):115-125 (2004).
Barclay, A. Neil et al., "CD200 and membrane protein interactions in the control of myeloid cells," Trends in Immunology, vol. 23(6):285-290 (2002).
Bello, Celeste et al., "Monoclonal Antibodies for B-Cell Lymphomas: Rituximab and Beyond," Hematology, pp. 233-242 (2007).
Borriello, Frank et al., "MRC OX-2 Defines a Novel T Cell Costimulatory Pathway," The Journal of Immunology, vol. 158:4548-4554 (1997).
Broderick, Cathryn et al., "Constitutive Retinal CD200 Expression Regulates Resident Microglia and Activation State of Inflammatory Cells during Experimental Autoimmune Uveoretinitis," American Journal of Pathology, vol. 161 (5):1669-1677 (2002).
Burge, Daniel J. et al., "Pharmacokinetic and Pharmacodynamic Properties of TRU-015, a CD2O-Directed Small Modular Immunopharmaceutical Protein Therpeutic, in Patients with Rheumatoid Arthritis: A Phase I, Open-Label, Dose-Escalation Clinical Study," Clinical Therapeutics, vol. 30(10):1806-1816 (2008).
Chen, Z. et al., "Cloning and characterization of the murine homologue of the rat/human MRC OX-2 gene," Biochimica et Biophysica Acta, vol. 1362:6-10 (1997).
Chen, Dang-Xiao et al., "Discrete Monoclonal Antibodies Define Functionally Important Epitopes in the CD200 Molecule Responsible for Immunosuppression Function," Transplantation, vol. 79:282-288 (2005).
Chen, Dang-Xiao et al., "Synthetic peptides from the N-terminal regions of CD200 and CD200R1 modulate immunosuppressive and anti-inflammatory effects of CD200-CD200R1 interaction," International Immunology, vol. 17 (3):289-296 (2005).
Cherwinski, Holly M. et al., "The CD200 Receptor Is a Novel and Potent Regulator of Murine and Human Mast Cell Function," The Journal of Immunology, vol. 174:1348-1356 (2005).
Cui, Weiguo et al., "CD200 and its receptor, CD200R, modulate bone mass via the differentiation of osteoclasts," PNAS, vol. 104(36):14436-14441 (2007).
Ebert, Ellen C. et al., "Selective Immunosuppressive Action of a Factor Produced by Colon Cancer Cells," Cancer Research, vol. 50:6158-6161 (1990).
Ennishi, D. et al., "CD5 expression is potentially predictive of poor outcome among biomarkers in patients with diffuse large B-cell lymphoma receiving rituximab plus Chop therapy," Annals of Oncology, vol. 19:1921-1926 (2008).
Fallarino, Francesca et al., "Murine Plasmacytoid Dendritic Cells Initiate the Immunosuppressive Pathway of Tryptophan Catabolism in Response to CD200 Receptor Engagement," The Journal of Immunology, vol. 173:3748-3754 (2004).
Frediberg, Jonathan W., "Unique Toxicities and Resistance Mechanisms Associated with Monoclonal Antibody Therapy," Hematology, pp. 329-334 (2005).
Gorczynski, R.M. et al., "A CD200FC Immunoadhesin Prolongs Rat Islet Xenograft Survival in Mice," Transplantation, vol. 73(12):1948-1953 (2002).
Gorczynski, Reginald M. et al., "An Immunoadhesin Incorporating the Molecule OX-2 Is a Potent Immunosuppressant That Prolongs Allo- and Xenograft Survival," The Journal of Immunology, vol. 163:1654-1660 (1999).
Gorczynski, Reginald M. et al., "Anti-CD200R Ameliorates Collagen-Induced Arthritis in Mice," Clinical Immunology, vol. 104(3):256-264 (2002).

(56) References Cited

OTHER PUBLICATIONS

Gorczynski, R.M. et al., "Anti-Rat OX-2 Blocks Increased Small Intestinal Transplant Survival After Portal Vein Immunization," Transplantation Proceedings, vol. 31:577-578 (1999).
Gorczynski, Reginald M. et al., "Augmented Induction of CD4+ CD25+ Treg using Monoclonal Antibodies to CD200R," Transplantation, vol. 79:1180-1183 (2005).
Gorczynski, Reginald M., "CD200 and its receptors as targets for immunoregulation," Current Opinion in Investigational Drugs, vol. 6(5):483-488 (2005).
Gorczynski, Reginald M. et al., "CD200 Immunoadhesin Suppresses Collagen-Induced Arthritis in Mice," Clinical Immunology, vol. 101(3):328-334 (2001).
Gorczynski, Reginald et al., "CD200 Is a Ligand for All Members of the CD200R Family of Immunoregulatory Molecules," the Journal of Immunology, vol. 172:7744-7749 (2004).
Gorczynski, R. et al., "Dendritic Cells Expressing TGFbeta/IL-10, and Cho Cells With OX-2, Increase Graft Survival," Transplantation Proceedings, vol. 33:1585-1566 (2001).
Gorczynski, Reg M., "Evidence for an Immunoregulatory Role of OX2 with Its Counter Ligand (OX2L) in the Regulation of Transplant Rejection, Fetal Loss, Autoimmunity and Tumor Growth," Archivum Immunologiae et Therapiae Experimentalis, vol. 49:303-309 (2001).
Gorczynski, R.M. et al., "Evidence for Persistent Expression of OX2 as a Necessary Component of Prolonged Renal Allograft Survival Following Portal Vein Immunization," Clinical Immunology, vol. 97(1):69-78 (2000).
Gorczynski, R.M. et al., "Evidence of a role for CD200 in regulation of immune rejection of leukaemic tumour cells in C57BL/6 mice," Clin. Exp. Immunol., vol. 126:220-229 (2001).
Gorczynski, Laura et al., "Evidence That an Ox-2-Positive Cell Can Inhibit the Stimulation of Type 1 Cytokine Production by Bone Marrow-Derived B7-1 (and B7-2)-Positive Dendritic Cells," The Journal of Immunology, vol. 162:774-781 (1999).
Gorczynski, Reginald M. et al., "Increased Expression of the Novel Molecule OX-2 is Involved in Prolongation of Murine Renal Allograft Survival," Transplantation, vol. 65(8):1106-1114 (1998).
Gorczynski, Reginald M. et al., "Induction of Tolerance-Inducing Antigen-Presenting Cells in Bone Marrow Cultures in Vitro Using Monoclonal Antibodies to CD200R," Transplantation, vol. 77(8):1138-1144 (2004).
Gorczynski, R.M. et al., "Persistent expression of OX-2 is necessary for renal allograft survival," FASEB Journal, vol. 14(6):A1069, Poster Presentation No. 102.4 (2000).
Gorczynski, Reginald M. et al., "Receptor Engagement on Cells Expressing a Ligand for the Tolerance-Inducing Molecule OX2 Induces an Immunoregulatory Population That Inhibits Alloreactivity in Vitro and in Vivo," The Journal of Immunology, vol. 165:4845-4860 (2000).
Gorczynski, R.M. et al., "Structural and Functional Heterogeneity in the CD200R Family of Immoregulatory Molecules and their Expression at the Feto-maternal Interface," American Journal of Reproeuctive Immunology, vol. 52:147-163 (2004).
Gorczynski, R.M. et al., "Synergy in Induction of Increased Renal Allograft Survival after Portal Vein Infusion of Dendritic Cells Transduced to Expression TGFbeta and IL-10, along with Administration of Cho Cells Expressing the Regulatory Molecule OX-2," Clinical Immunology, vol. 95(3):182-189 (2000).
Gorczynski, Reginald M., "Transplant tolerance modifying antibody to CD200 receptor, but not CD200, alters cytokine production profile from stimulated macrophages," Eur. J. Immunol., vol. 31:2331-2337 (2001).
Hatherley, Deborah et al., "The CD200 and CD200 receptor cell surface proteins interact through their N-terminal immunoglobulin-like domains," Eur. J. Immunol., vol. 34:1688-1694 (2004).
Hernandez-Ilizaliturri, F.J. et al., "Strategies to overcoming rituximab-chemotherapy resistance by targeting the autophagy pathway using bortezomib in combination with the BCL-2 inhibitor obatoclax in non-Hodgkin's lymphomas (NHL)," Journal of Clinical Oncology, 2009 ASCO Annual Meeting Proceedings, vol. 27(15S), Poster Presentation No. 8543, 1 page (2009).
Hoek, Robert M., "Down-Regulation of the Macrophage Lineage Through Interaction with OX2 (CD200)," Science, vol. 290(5497):1768-1771 (2000).
Hoek, R.M., et al., "Macrophage regulation by the B7.112 homologue OX2?" FASEB Journal, vol. 14(6):A1232, Poster Presentation No. 193.1 (2000).
Holodick, Nichol E. et al., "Adult Bm generates CD5+ B1 cells containing abundant N-region additions," Eur. J. Immunol., vol. 39(9):2383-2394 (2009).
Hutchings, N. J. et al., "Interactions of Cytoplasmic Region of OX2R are Consistent wtih an Inhibitory Function," Annual Congress of the British Society for Immunology, vol. 101(Suppl. 1), Poster Presentation No. 10.6, 1 page (2000).
Kausar, Fariha et al., "Ocrelizumab: a step forward in the evolution of B-cell therapy," Expert Opin. Biol. Ther., vol. 9 (7):889-895 (2009).
Kretz-Rommel, Anke et al., "CD200 Expression on Tumor Cells Suppresses Antitumor Immunity: New Approaches to Cancer Immunotherapy," The Journal of Immunology, vol. 178:5595-5605 (2007).
Kretz-Rommel, Anke et al., "The Immuno-Regulatory Protein CD200 Is Overexpressed in a Subset of B-Cell Lymphocytic Leukemias and Plays a Role in Down-Regulating the TH1 Immune Response," J. Immunother., vol. 27 (6):S46 (2004).
Levene, Adam P. et al., "Therapeutic monoclonal antibodies in oncology," Journal of the Royal Society of Medicine, vol. 98:146-152 (2005).
Marti, G.E. et al., "CD20 and CD5 Expression in B-Chronic Lymphocytic Leukemia," Ann. N.Y. Acad. Sci., vol. 651:480-483 (1992).
Mcwhirter, John R. et al., "Antibodies selected from combinatorial libraries block a tumor antigen that plays a key role in immunomodulation," PNAS, vol. 103(4):1041-1046 (2006).
Milani, Cannon et al., "Veltuzumab, an anti-CD20 mAb for the treatment of non-Hodgkin's lymphoma, chronic lymphocytic leukemia and immune thrombocytopenic purpura," Current Opinion in Molecular Therapeutics, vol. 11 (2):200-207 (2009).
Morschhauser, Franck et al., "Humanized Anti-CD20 Antibody, Veltuzumab, in Refractory/Recurrent Non-Hodgkin's Lymphoma: Phase I/II Results," Journal of Clinical Oncology, vol. 27(20):3346-3353 (2009).

* cited by examiner

THERAPEUTIC METHODS USING ANTI-CD200 ANTIBODIES

CROSS-REFERENCE TO RELATED APPLICATIONS

This application is a national stage filing under 35 U.S.C. §371 of International Application No. PCT/US2011/024511, filed Feb. 11, 2011, which claims the benefit of the filing date under 35 U.S.C. §119(e) to U.S. provisional patent application Ser. No. 61/337,962, filed on Feb. 11, 2010, the entire contents of which is hereby incorporated by reference. International Application No. PCT/US2011/024511 was published under PCT Article 21(2) in English.

SEQUENCE LISTING

The instant application contains a Sequence Listing which has been submitted via EFS-Web and is hereby incorporated by reference in its entirety. Said ASCII copy, created on Aug. 10, 2012, is named ALXN1520.txtALXN152301 Seq.txt, and is 19,633 bytes in size.

TECHNICAL FIELD

The field of the invention is medicine, immunology, molecular biology, and protein chemistry.

BACKGROUND

Human CD200 protein is a type 1a transmembrane glycoprotein that is normally expressed on thymocytes (e.g., T cells and B cells), neurons, and endothelial cells. Through engagement with its cognate receptor, CD200R, CD200 protein transduces an immunoregulatory signal that can suppress T-cell-mediated immune responses. CD200 knockout animal studies as well as experiments using antagonist anti-CD200 antibodies and recombinant CD200-Fc fusion proteins have demonstrated that CD200 protein is an immunosuppressive agent in autoimmune disorder and during transplantation. See, e.g., Hoek et al. (2000) *Science* 290:1768-1771 and Gorczynski et al. (1999) *J Immunol* 163:1654-1660. The interaction between CD200 and CD200R results in altered cytokine profiles and promotes a $T_H2$ T cell response over a $T_H1$ response. (See, e.g., Kretz-Rommel (2007) *J Immunol* 178:5595-5605.)

SUMMARY

The present disclosure is based, at least in part, on the discovery by the inventors that administration of an anti-CD200 antibody to an animal model of an autoimmune disease (autoimmune hemolytic disease) resulted in a marked decrease in production by the animal of disease-associated autoantibodies. Administration of the anti-CD200 antibody also resulted in a marked delay in onset of production of autoantibodies in the mice. Because production of autoantibodies by a host is causative or associated with a number of autoimmune disorders (e.g., myasthenia gravis and Guillain-Barré syndrome), the inventors believe that an anti-CD200 antibody will be useful for treating patients suffering from any one of a variety of autoimmune disorders.

Accordingly, in one aspect, the disclosure features a method for treating an autoimmune disorder in a human. The method includes administering to a human having an autoimmune disorder an amount of an anti-CD200 antibody that is sufficient to reduce in the human the concentration of an autoantibody (or the production or expression of an autoantibody) associated with the autoimmune disorder to thereby treat the autoimmune disorder.

In some embodiments, administration of the anti-CD200 antibody can reduce the autoantibody concentration in the blood of the human by at least 10%, 20%, 50%, 75%, or more than 75%. In some embodiments, administration of the anti-CD200 antibody to the human can completely eliminate detectable autoantibody in the human.

The disclosure also features a methods for preventing an autoimmune disorder or delaying the onset of the autoimmune disorder, which method includes administering to a human having an autoimmune disorder an amount of an anti-CD200 antibody that is sufficient to: (i) prevent the generation, production, or expression by the human of an autoantibody associated with the autoimmune disorder or (ii) delay the generation of, or the onset of production or expression by the human of, the autoantibody associated with the autoimmune disorder, to thereby prevent or delay the onset of the autoimmune disorder.

In yet another aspect, the disclosure features a method for treating an autoimmune disorder in a human, which method includes chronically administering to a human having an autoimmune disorder an anti-CD200 antibody in an amount and with a frequency sufficient to maintain in the human a reduced concentration of an autoantibody associated with the autoimmune disorder to thereby treat the autoimmune disorder.

In some embodiments, the anti-CD200 antibody can be administered to the human in an amount and with a frequency to maintain a greater than 10%, 20%, 50%, 75%, or greater than 75% reduction in the concentration of the autoimmune antibody as compared to the concentration of the antibody prior to administration of the anti-CD200 antibody.

The inventors also discovered several biomarkers evidencing the occurrence in a human of an immunomodulatory effect by an anti-CD200 antibody administered to animals with an autoimmune disorder. For example, the inventors have observed that following administration of an anti-CD200 antibody to an animal, the concentration of several leukocyte and bone marrow cell subsets is reduced in the animals. The inventors have also discovered that the concentration of, e.g., F4/80$^+$ lymphocytes in spleen are increased following administration of the anti-CD200 antibody to the animal. While the disclosure is not bound by any particular theory or mechanism of action, the inventors believe that monitoring a patient treated with an anti-CD200 antibody for the occurrence of one or more of these biomarkers is useful for, at bottom, determining whether the anti-CD200 antibody is capable of producing an immunomodulatory effect in the human to which the antibody is administered. Moreover, one or more of the biomarkers are also useful for identifying a dose—a threshold dose—of an anti-CD200 antibody, such as samalizumab (ALXN6000), that by virtue of its immunomodulatory effect in the human is sufficient to achieve a clinically-meaningful effect on the disease (i.e., sufficient to treat a disease such as cancer or an autoimmune disorder). To wit, as described in the working examples an anti-CD200 antibody was capable of reducing the expression of autoimmune antibodies in a mouse model of autoimmune disease.

Accordingly, the disclosure also features a method for treating a disorder in a human, the method comprising administering to a human in need thereof an anti-CD200 antibody in an amount and with a frequency sufficient to treat the disorder by maintaining one or more of the following physiological conditions in the human: (i) a decreased (reduced) concentration of at least one CD200$^+$ leukocyte subset as compared to a control concentration; (ii) an increased concentration of F4/80$^+$ cells as compared to a control concentration; and (iii) a decreased (reduced) concentration of at least one bone marrow stem cell subset as compared to a control concentration. The disorder can be any disorder that a medical practitioner reasonably believes can be treated by a therapeutic anti-CD200 antibody. Such diseases include, e.g., a cancer or an autoimmune disease.

In some embodiments, the at least one CD200$^+$ leukocyte subset can be one selected from the group consisting of CD3$^+$/CD200$^+$ cells, CD45R$^+$/CD200$^+$ cells, CD5$^+$/CD200$^+$ cells, CD19$^+$/CD200$^+$ cells, CD138$^+$/CD200$^+$ cells, and CD200R$^+$/CD200$^+$ cells. In some embodiments, the at least one bone marrow stem cell subset can be one selected from the group consisting of CD200$^+$ bone marrow cells, Igk$^+$/CD200$^+$ bone marrow cells, CD138$^+$/CD200$^+$ bone marrow cells, c-kit$^+$/CD200$^+$ bone marrow cells, and c-kit$^+$/CD200$^+$/Lin$^{-/low}$ bone marrow cells. In some embodiments, the F4/80$^+$ cells can be F4/80$^+$ macrophages.

In some embodiments, at least one CD200$^+$ leukocyte subset or the F4/80$^+$ cells can be present in the peripheral blood of the human. In some embodiments, the leukocytes or cells are resident in the spleen.

In some embodiments, the antibody can be administered to the human in an amount and with a frequency to maintain at least two, or all three, of the physiological conditions in the human.

In some embodiments, the autoimmune disorder can be a hemolytic disorder or an autoimmune hemolytic anemia (AIHA) such as any of the AIHA known in the art of medicine (see below). In some embodiments, the autoimmune disorder can be one selected from the group consisting of chronic obstructive pulmonary disease, diabetes mellitus type 1, Goodpasture's syndrome, Grave's disease, Guillain-Barré syndrome, IgA nephropathy, scleroderma, Sjögren's syndrome, Wegener's granulomatosis, pemphigus vulgaris, rheumatoid arthritis, cold agglutinin disease, anti-phospholipid syndrome, warm autoimmune hemolytic anemia, paroxysmal cold hemoglobinuria, Hashimoto's disease, idiopathic thrombocytopenic purpura, myasthenia gravis, pulmonary biliary cirrhosis, and Miller Fisher syndrome.

In some embodiments, the autoimmune disorder can be the result of, or can be associated with, a cancer in the human. The cancer can be a liquid tumor such as, but not limited to, chronic lymphocytic leukemia (e.g., B cell chronic lymphocytic leukemia) or multiple myeloma.

In some embodiments, the methods described herein can include administering to the human at least one additional therapeutic agent for treating an autoimmune disorder or a cancer.

The inventors have discovered that administration of an anti-CD200 antibody to an animal resulted in a marked reduction in the concentration of CD5$^+$ cells (e.g., CD5$^+$ leukocytes) in the spleen of the animal. CD5 is a 67 kDa transmembrane glycoprotein that is expressed by T cells and a subset of B cells referred to as "B1 cells." See, e.g., Holodick et al. (2009) *Eur J Immunol* 39(9):2383-2394. B1 cells are integrally involved in host defense against infections and CD5$^+$ B1 cells spontaneously and constitutively express immunoglobulin. Id. CD5 expression by CLL cells has also been detected. In 1992, Almasri et al. reported that CD5$^+$ CLL cells express lower levels of CD20 as determined by flow cytometry. *Am J Hematol* 40:259, 261. See also Marti et al. (1992) "CD20 and CD5 expression in B-chronic lymphocytic leukemia" *Ann N.Y. Acad Sci* 651:480-483.

Rituximab is a chimeric, monoclonal anti-CD20 antibody clinically-approved for the treatment of, among other things, chronic lymphocytic leukemia (CLL). See, e.g., Christian and Lin (2008) *Semin Hematol* 45(2):95-103. Rituximab has been effective for treating CLL both as a single agent and in combination, e.g., with the CHOP regimen (cyclophosphamide, doxorubicin, vincristine, and prednisone). Id. However, Ennishi et al. reported a correlation between CD5 expression by CLL cells and poor outcome in CLL patients treated with a combined RCHOP regimen (rituximab and CHOP regimen). (2008) *Annals of Oncology* 19:1921, 1924 (FIG. 1). The report suggests that there exists a population of patients who receive less benefit from rituximab therapy and may require alternative therapies.

While the disclosure is not bound by any particular theory or mechanism of action, it is likely that CD5$^+$ CLL cells may be refractory to rituximab therapy at least in part because of a reduced expression of CD20. The inventors have shown that a therapeutic composition containing an anti-CD200 antibody is useful for reducing CD5$^+$ cell populations in an animal and thus believe that the composition is particularly useful for treating a subset of CLL patients that are refractory to treatment with anti-CD20 therapy (e.g., rituximab-resistant).

Accordingly, the disclosure also features a method for treating a human afflicted with a cancer or an autoimmune disorder, the method comprising administering to a human afflicted with a cancer or an autoimmune disorder an anti-CD200 antibody in an amount that is sufficient to treat the cancer or the autoimmune disorder, wherein the cancer or autoimmune disorder is resistant, or is suspected of being resistant, or is likely to become resistant, to therapy with an anti-CD20 therapeutic agent.

In another aspect, the disclosure features a method for treating a human afflicted with a cancer, the method comprising administering to a human afflicted with a cancer an anti-CD200 antibody in an amount that is sufficient to treat the cancer, wherein the cancer is resistant, is suspected of being resistant, or is likely to become resistant, to therapy with an anti-CD20 therapeutic agent.

In another aspect, the disclosure features another method for treating a human afflicted with a cancer, the method comprising: identifying a human as having a cancer that is resistant, or is suspected to be resistant, to treatment with an anti-CD20 therapeutic agent; and administering to the human an anti-CD200 antibody in an amount that is effective to treat the cancer.

In some embodiments, the cancer can comprise or consist of cancer cells that express CD5.

In some embodiments, more than one dose (e.g., at least two, three, four, five, six, seven, eight, nine, 10, 11, 12, 13, 14, 15, 16, 17, 18, 19, or 20 or more doses) of the anti-CD200 antibody is administered to the human. In some embodiments, more than 10 (e.g., more than 15, 20, 25, 30, or 35 or more) doses of the anti-CD200 antibody are administered to the human.

In some embodiments, the cancer is a solid tumor. Solid tumors include, e.g., lung cancer, breast cancer, colon cancer, pancreatic cancer, renal cancer, stomach cancer, liver cancer, bone cancer, neural tissue cancer (e.g., neuroblastoma), melanoma, thyroid cancer, ovarian cancer, testicular cancer, prostate cancer, cervical cancer, vaginal cancer, and bladder cancer. In some embodiments, the cancer is a liquid tumor. Liquid tumors include, e.g., leukemias (e.g., chronic lymphocytic leukemia such as B cell or T cell type chronic lymphocytic leukemia) and multiple myeloma. Bone cancers include, without limitation, osteosarcoma and osteocarcinomas.

In yet another aspect, the disclosure features a method for treating a human afflicted with a liquid tumor. The method includes administering to a human afflicted with a liquid tumor an anti-CD200 antibody in an amount that is sufficient to treat the liquid tumor, wherein at least a portion of the liquid tumor cells express CD5. The method can include determining whether the portion of liquid tumor cells express CD5.

In another aspect, the disclosure features a method for treating a human afflicted with a liquid tumor, which method includes: identifying a human as having a liquid tumor comprising cells that express CD5; and administering to the human an anti-CD200 antibody in an amount that is sufficient to reduce the concentration of the CD5-expressing liquid tumor cells in the human to thereby treat the liquid tumor.

In another aspect, the disclosure features a method for treating a human afflicted with a liquid tumor, the method comprising administering to a human afflicted with a liquid tumor an anti-CD200 antibody and an anti-CD20 therapeutic agent to thereby treat the liquid tumor, wherein at least a portion of the liquid tumor cells express CD5 prior to administering the antibody and agent.

In another aspect, the disclosure features a method for treating a human afflicted with a liquid tumor, wherein the method includes: identifying a human as being afflicted with a liquid tumor comprising tumor cells that express CD5; and administering to the human an anti-CD200 antibody and an anti-CD20 therapeutic agent to thereby treat the liquid tumor.

In some embodiments, the anti-CD20 therapeutic agent can be administered prior to administration of the anti-CD200 antibody. In some embodiments, the anti-CD200 antibody is administered prior to administration of the anti-CD20 therapeutic agent. The anti-CD200 antibody and the anti-CD20 therapeutic agent can be administered at the same time. The antibody can be administered using the same administration route (e.g., intravenous administration) or different route.

In some embodiments, the anti-CD200 antibody and anti-CD20 therapeutic agent can be administered to the human concurrently as a bispecific antibody that binds to human CD200 and to human CD20. That is, the therapeutic agent administered to the human has both the properties of an anti-CD200 antibody and the anti-CD20 therapeutic agent. In some embodiments, the bispecific anti-CD200 antibody/anti-CD20 antibody is a DVD-Ig antibody.

In some embodiments, at least 1%, 5%, 10%, 20%, 30%, 40%, 50%, or 60% or more of the liquid tumor cells express CD5.

The liquid tumor can be, e.g., a chronic lymphocytic leukemia or multiple myeloma. The liquid tumor can be, e.g., a B cell chronic lymphocytic leukemia.

In some embodiments, the anti-CD20 therapeutic agent is an anti-CD20 antibody such as, but not limited to, rituximab, ofatumumab, TRU-015, veltuzumab, ocrelizumab, or AME-133v.

In some embodiments, the anti-CD20 therapeutic agent is conjugated to a toxin. For example, in some embodiments, the anti-CD20 therapeutic agent is a toxin-antibody conjugate. The toxin can be, e.g., a small molecule drug or a toxic polypeptide (e.g., ricin or saporin). In some embodiments, the toxin can be a bacterial toxin, a fungal toxin, or a plant toxin. In some embodiments, the toxin can be a radioactive agent such as, but not limited to, $^{90}$Y, $^{186}$Re, $^{188}$Re, $^{64}$Cu, $^{67}$Cu, $^{212}$Pb, $^{212}$Bi, $^{213}$Bi, $^{123}$I, $^{125}$I, $^{131}$I, $^{111}$In, $^{211}$At, $^{32}$P, $^{177}$Lu, $^{47}$Sc, $^{105}$Rh, $^{109}$Pd, $^{153}$Sm, or $^{199}$Au. In some embodiments, the toxin-antibody conjugate is $^{90}$Y-ibritumomab tiuxetan or $^{131}$I-tositumomab.

In some embodiments, the anti-CD200 antibody inhibits the interaction between CD200 and CD200R.

In some embodiments of any of the methods described herein, the anti-CD200 antibody can contains the following paired set of CDRs: a heavy chain CDR1 (HCDR1) comprising the amino acid sequence: GFTFSGFAMS (SEQ ID NO:4); a heavy chain CDR2 (HCDR2) comprising the amino acid sequence: SISSGGTTYYLDSVKG (SEQ ID NO:5); a heavy chain CDR3 (HCDR3) comprising the amino acid sequence: GNYYSGTSYDY (SEQ ID NO:6); a light chain CDR1 (LCDR1) comprising the amino acid sequence: RASESVDSYGNSFMH (SEQ ID NO:7); a light chain CDR2 (LCDR2) comprising the amino acid sequence: RASNLES (SEQ ID NO:8); and a light chain CDR3 (LCDR3) comprising the amino acid sequence: QQSNEDPRT (SEQ ID NO:9).

In some embodiments of any of the methods described herein, the anti-CD200 antibody contains the following paired set of CDRs: a HCDR1 comprising the amino acid sequence: GFNIKDYYMH (SEQ ID NO:10); a HCDR2 comprising the amino acid sequence: WIDPENGDTKYAPKFQG (SEQ ID NO:11); a HCDR3 comprising the amino acid sequence: KNYYVSNYNFFDV (SEQ ID NO:12); a LCDR1 comprising the amino acid sequence: SASSSVRYMY (SEQ ID NO:13); a LCDR2 comprising the amino acid sequence: DTSKLAS (SEQ ID NO:14); and a LCDR3 comprising the amino acid sequence: FQGSGYPLT (SEQ ID NO:15).

In some embodiments of any of the methods described herein, the anti-CD200 antibody contains the following paired set of CDRs: a HCDR1 comprising the amino acid sequence: GFNIKDYYIH (SEQ ID NO:16); a HCDR2 comprising the amino acid sequence: WIDPEIGATKYVPKFQG (SEQ ID NO:17); a HCDR3 comprising the amino acid sequence: LYGNYDRYYAMDY (SEQ ID NO:18); a LCDR1 comprising the amino acid sequence: KASQNVRTAVA (SEQ ID NO:19); a LCDR2 comprising the amino acid sequence: LASNRHT (SEQ ID NO:20); and a LCDR3 comprising the amino acid sequence: LQHWNYPLT (SEQ ID NO:21).

In some embodiments of any of the methods described herein, the anti-CD200 antibody contains the following paired set of CDRs: a HCDR1 comprising the amino acid sequence: GYSFTDYIIL (SEQ ID NO:22); a HCDR2 comprising the amino acid sequence: HIDPYYGSSNYNLKFKG (SEQ ID NO:23); a HCDR3 comprising the amino acid sequence: SKRDYFDY (SEQ ID NO:24); a LCDR1 comprising the amino acid sequence: KASQDINSYLS (SEQ ID NO:25); a LCDR2 comprising the amino acid sequence: RANRLVD (SEQ ID NO:26); and a LCDR3 comprising the amino acid sequence: LQYDEFPYT (SEQ ID NO:27).

In some embodiments of any of the methods described herein, the anti-CD200 antibody contains the following paired set of CDRs: a HCDR1 comprising the amino acid sequence: GYTFTEYTMH (SEQ ID NO:28); a HCDR2 comprising the amino acid sequence: GVNPNNGGALYNQKFKG (SEQ ID NO:29); a HCDR3 comprising the amino acid sequence: RSNYRYDDAMDY (SEQ ID NO:30); a LCDR1 comprising the amino acid sequence: KSSQSLLDIDEKTYLN (SEQ ID NO:31); a LCDR2 comprising the amino acid sequence: LVSKLDS (SEQ ID NO:32); and a LCDR3 comprising the amino acid sequence: WQGTHFPQT (SEQ ID NO:33).

In some embodiments of any of the methods described herein, the anti-CD200 antibody contains the following paired set of CDRs: a HCDR1 comprising the amino acid sequence: AFNIKDHYMH (SEQ ID NO:34); a HCDR2 comprising the amino acid sequence: WIDPESGDTEYAPKFQG (SEQ ID NO:35); a HCDR3 comprising the amino acid sequence: FNGYQALDQ (SEQ ID NO:36); a LCDR1 comprising the amino acid sequence: TASSSVSSSYLH (SEQ ID NO:37); a LCDR2 comprising the amino acid sequence: STSNLAS (SEQ ID NO:38); and a LCDR3 comprising the amino acid sequence: RQYHRSPPIFT (SEQ ID NO:39).

In some embodiments, the anti-CD200 antibody and/or the anti-CD20 antibody is an IgG1, IgG2, IgG2a, IgG3, IgG4, IgM, IgA1, IgA2, IgA, IgD, or IgE antibody. In some embodiments, the anti-CD200 antibody and/or the anti-CD20 antibody is a murine antibody, a chimeric antibody, a humanized antibody, a single chain antibody, or a human antibody. In some embodiments, the anti-CD200 antibody or the anti-CD20 antibody is an antigen-binding antibody fragment selected from the group consisting of a Fab fragment, a F(ab')$_2$ fragment, a Fab' fragment, an scFv fragment, a minibody, a diabody, or a triabody In yet another aspect, the disclosure features a method for selecting a therapy for a patient afflicted with a liquid tumor, the method comprising: identifying a patient as having a liquid tumor comprising tumor cells that express CD5; and selecting for the patient an anti-CD200 antibody for use in treating the liquid tumor.

In another aspect, the disclosure features a method for prescribing a therapy for a patient afflicted with a liquid tumor, the method comprising: identifying a patient as having a liquid tumor comprising tumor cells that express CD5; and prescribing for the patient an anti-CD200 antibody for use in treating the liquid tumor. The anti-CD200 antibody can be a bispecific antibody such as one that comprises a first antigen-combining site and a second antigen-combining site, wherein the first antigen-combining site binds to CD200 and the second antigen-combining site binds to CD20.

In yet another aspect, the disclosure features a bispecific antibody that comprises a first antigen-combining site and a second antigen-combining site, wherein the first antigen-combining site binds to CD200 and the second antigen-combining site binds to CD20. The bispecific antibody can be, e.g., an IgG1, IgG2, IgG2a, IgG3, IgG4, IgM, IgA1, IgA2, IgA, IgD, or IgE antibody. In some embodiments, the bispecific anti-CD200/anti-CD20 antibody is a murine antibody, a chimeric antibody, a humanized antibody, a single chain antibody, or a human antibody. In some embodiments, the bispecific antibody can be used in any of the methods described herein (e.g., treating cancer or an autoimmune disease).

In yet another aspect, the disclosure features: (i) a nucleic acid encoding the bispecific antibody; (ii) a vector (e.g., an expression vector) comprising the nucleic acid; and (iii) a cell comprising the vector. In another aspect, the disclosure features a method for producing the antibody, the method comprising culturing the cell for a time and under conditions sufficient to allow for production of the antibody in the cell. The method can also include the step of isolating the bispecific antibody from the cell or from the media in which the cell is cultured.

In some embodiments, the bispecific antibody is a single chain diabody, a tandem single chain Fv fragment, a tandem single chain diabody, or a fusion protein comprising a single chain diabody and at least a portion of an immunoglobulin heavy chain constant region. In some embodiments, the bispecific antibody is a dual variable domain immunoglobulin.

In some embodiments, the first antigen combining site binds to a human CD200 protein, e.g., a human CD200 protein comprising the amino acid sequence depicted in any one of SEQ ID NOs:1 to 3. In some embodiments, the second antigen combining site binds to a human CD20 protein, e.g., a human CD20 protein comprising the amino acid sequence depicted in any one of SEQ ID NOs: 40 to 42. In some embodiments, the second antigen combining site binds to a human CD20 protein at an epitope that comprises at least part (e.g., at least 4 amino acids) of the amino acid sequence depicted in SEQ ID NO:41 and at least part (e.g., at least 4 amino acids) of the amino acid sequence depicted in SEQ ID NO:42.

In some embodiments, the first antigen combining site is obtained from samalizumab. In some embodiments, the second antigen combining site is obtained from rituximab, ofatumumab, TRU-015, veltuzumab, ocrelizumab, or AME-133v. The bispecific antibody can be conjugated to, or contain, a heterologous moiety such as a detectable label or a toxin.

"Polypeptide," "peptide," and "protein" are used interchangeably and mean any peptide-linked chain of amino acids, regardless of length or post-translational modification. The CD200 proteins described herein can contain or be wild-type proteins or can be variants that have not more than 50 (e.g., not more than one, two, three, four, five, six, seven, eight, nine, ten, 12, 15, 20, 25, 30, 35, 40, or 50) conservative amino acid substitutions. Conservative substitutions typically include substitutions within the following groups: glycine and alanine; valine, isoleucine, and leucine; aspartic acid and glutamic acid; asparagine, glutamine, serine and threonine; lysine, histidine and arginine; and phenylalanine and tyrosine.

The CD200 proteins and CD20 proteins described herein also include "antigenic peptide fragments" of the proteins, which are shorter than full-length proteins, but retain at least 10% (e.g., at least 10%, at least 15%, at least 20%, at least 25%, at least 30%, at least 35%, at least 40%, at least 50%, at least 55%, at least 60%, at least 70%, at least 80%, at least 90%, at least 95%, at least 98%, at least 99%, at least 99.5%, or 100% or more) of the ability of the full-length protein to induce an antigenic response in a mammal (see below under "Methods for Producing an Antibody"). Antigenic peptide fragments of a CD200 protein or a CD20 protein include terminal as well internal deletion variants of the protein. Deletion variants can lack one, two, three, four, five, six, seven, eight, nine, ten, 11, 12, 13, 14, 15, 16, 17, 18, 19, or 20 amino acid segments (of two or more amino acids) or non-contiguous single amino acids. Antigenic peptide fragments can be at least 6 (e.g., at least 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 110, 120, 130, 140, 150, 160, 170, 180, 190, or 200 or more) amino acid residues in length (e.g., at least 6 contiguous amino acid residues in any one of SEQ ID NOs:1 to 3). In some embodiments, an antigenic peptide fragment of a human CD200 protein is less than 225 (e.g., less than 200, 190, 180, 170, 160, 150, 140, 130, 120, 110, 100, 95, 90, 85, 80, 75, 60, 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, or 7) amino acid residues in length (e.g., less than 225 contiguous amino acid residues in any one of SEQ ID NOs:1 to 3). In some embodiments, an antigenic peptide fragment of a full-length CD200 protein is at least 6, but less than 225, amino acid residues in length.

In some embodiments, the human CD200 protein can have an amino acid sequence that is, or is greater than, 70 (e.g., 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100) % identical to the human CD200 protein having the amino acid sequence depicted in SEQ ID NO:1 or SEQ ID NO:2 (see below). In some embodiments, a human CD20 protein can have an amino acid sequence that is, or is greater than, 70 (e.g., 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100) % identical to the human CD200 protein having the amino acid sequence depicted in SEQ ID NO:40.

Percent (%) amino acid sequence identity is defined as the percentage of amino acids in a candidate sequence that are identical to the amino acids in a reference sequence, after aligning the sequences and introducing gaps, if necessary, to achieve the maximum percent sequence identity. Alignment for purposes of determining percent sequence identity can be achieved in various ways that are within the skill in the art, for instance, using publicly available computer software such as BLAST, BLAST-2, ALIGN, ALIGN-2 or Megalign (DNASTAR) software. Appropriate parameters for measuring alignment, including any algorithms needed to achieve maximal alignment over the full-length of the sequences being compared can be determined by known methods.

Amino acid sequences for exemplary human CD200 proteins and human CD20 proteins, as well as antigenic peptide fragments thereof are known in the art and are set forth below.

As used herein, the term "antibody" refers to a whole or intact antibody molecule (e.g., IgM, IgG (including IgG1, IgG2, IgG3, and IgG4), IgA, IgD, or IgE) or any antigen-binding fragment thereof. The term antibody includes, e.g., a chimerized or chimeric antibody, a humanized antibody, a deimmunized antibody, and a fully human antibody. Antigen-binding fragments of an antibody include, e.g., a single chain antibody, a single chain Fv fragment (scFv), an Fd fragment, an Fab fragment, an Fab' fragment, or an F(ab')$_2$ fragment. An scFv fragment is a single polypeptide chain that includes both the heavy and light chain variable regions of the antibody from which the scFv is derived. In addition, intrabodies, minibodies, triabodies, and diabodies (see, e.g., Todorovska et al. (2001) *J Immunol Methods* 248(1):47-66; Hudson and Kortt (1999) *J Immunol Methods* 231(1):177-189; Poljak (1994) *Structure* 2(12):1121-1123; Rondon and Marasco (1997) *Annual Review of Microbiology* 51:257-283, the disclosures of each of which are incorporated herein by reference in their entirety) are also included in the definition of antibody and are compatible for use in the methods described herein. Bispecific antibodies (including DVD-Ig antibodies; see below) are also embraced by the term "antibody." Bispecific antibodies are monoclonal, preferably human or humanized, antibodies that have binding specificities for at least two different antigens.

Unless otherwise defined, all technical and scientific terms used herein have the same meaning as commonly understood by one of ordinary skill in the art to which this disclosure pertains. In case of conflict, the present document, including definitions, will control. Preferred methods and materials are described below, although methods and materials similar or equivalent to those described herein can also be used in the practice or testing of the presently disclosed methods and compositions. All publications, patent applications, patents, and other references mentioned herein are incorporated by reference in their entirety.

Other features and advantages of the present disclosure, e.g., methods for treating a rituximab-resistant cancer (e.g., chronic lymphocytic leukemia), will be apparent from the following description, the examples, and from the claims.

DETAILED DESCRIPTION

The present disclosure relates to anti-CD200 antibodies and to use of the antibodies in methods for treating autoimmune disorders or cancer. Also featured are biomarkers for use in selecting or prescribing a treatment modality for a patient with an autoimmune disorder and/or cancer. In addition, the disclosure features methods of treatment using an anti-CD200 antibody in combination with one or more additional therapeutic agents such as an anti-CD20 therapeutic agent. While in no way intended to be limiting, exemplary anti-CD200 antibodies and CD200-binding fragments thereof, conjugates, pharmaceutical compositions and formulations, biomarkers, and methods employing any of the foregoing are elaborated on below and are exemplified in the working Examples.

Anti-CD200 Antibodies

Figure 3:
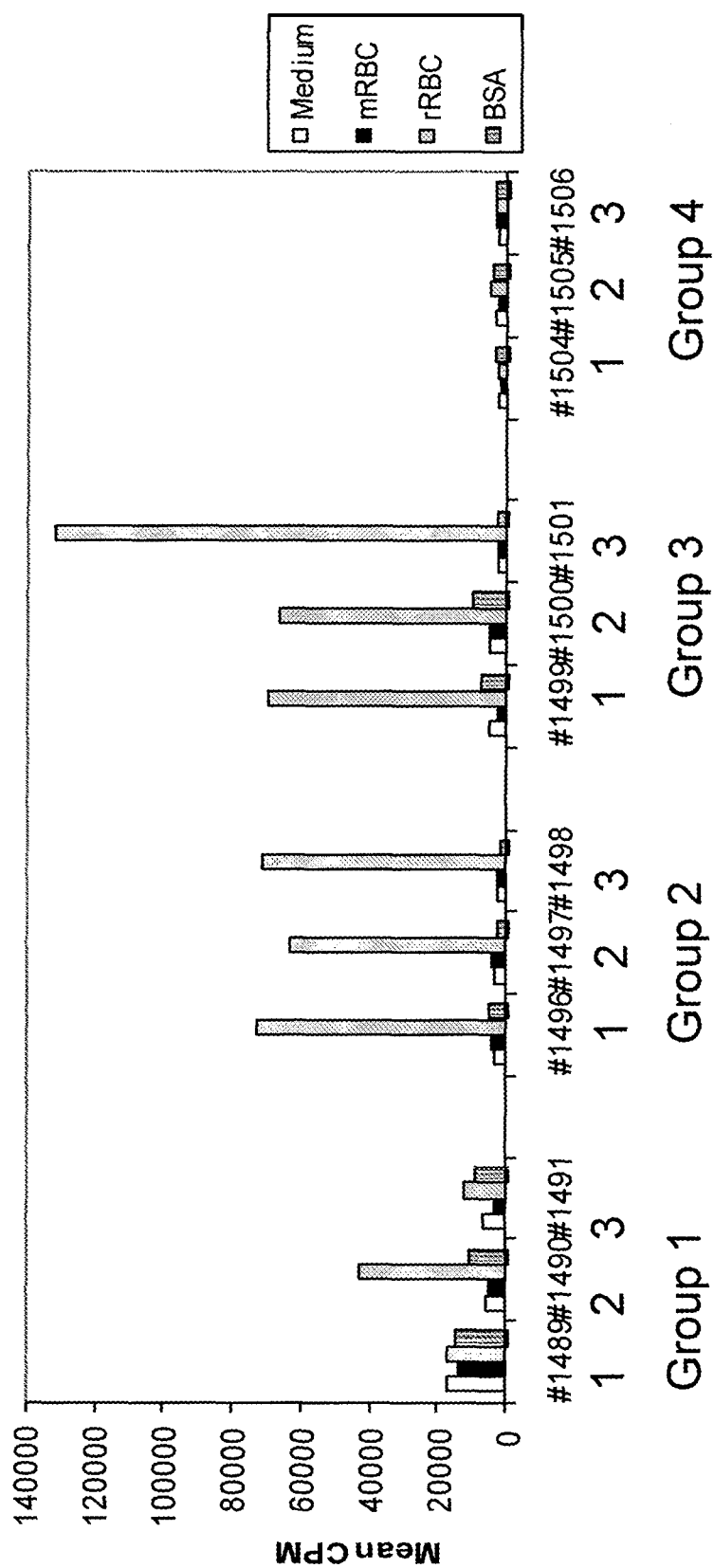
FIG. 3 is a bar graph depicting the reduction in antigen-induced proliferation of splenocytes isolated from mice treated with an anti-CD200 antibody. The Y-axis represents the mean counts per minute of $^3$H-thymidine radioactivity in nucleic acid isolated from each cell population. The X-axis represents individual mice, three (3) depicted in each group. For each mouse, the four measurements are for proliferation of splenocytes induced by medium alone, mouse red blood cells (mRBC), rat red blood cells (rRBC), or bovine serum albumin (BSA). The mice of Group 1 were treated with an anti-CD200 antibody with effector function (Antibody 1) at a dose of 5 mg/kg. The mice of Group 2 were treated with Antibody 1 at a dose of 1 mg/kg. The mice of Group 3 were treated with a control antibody that does not bind to CD200 and the mice of Group 4 were not treated with an antibody or immunized with the rat red blood cells.

The disclosure features antibodies that bind to a human CD200 polypeptide (sometimes the antibodies are referred to herein as "anti-CD200 antibodies"). Also featured are antigen-binding (CD200-binding) fragments of the antibodies. In some embodiments, an anti-CD200 antibody described herein binds to an epitope in the human CD200 protein. For example, the anti-CD200 antibody can bind to an epitope in the human CD200 protein comprising, or consisting of, the following amino acid sequence: MERLVIRMPFSHLSTYS-LVWVMAAVVLCTAQVQVVTQDEREQLYTPASLKC SLQNAQEALIVTWQKKKAVSPENMVTF-SENHGVVIQPAYKDKINITQLGLQN STITFWNITLE-DEGCYMCLFNTFGFGKISGTA-CLTVYVQPIVSLHYKFSEDHLN ITCSATARPAPMVFWKVPRSGIEN-STVTLSHPNGTTSVTSILHIKDPKNQVGKE VICQV-LHLGTVTDFKQTVNKGYWFSV-PLLLSIVSLVILLVLISILLYWKRHRNQ DREP (SEQ ID NO:1; Genbank Accession No. NP_005935.2). SEQ ID NO:1 depicts the amino acid sequence for a full-length, precursor human CD200 isoform A protein. In some embodiments, an anti-CD200 antibody described herein binds to an epitope in the human CD200 protein comprising, or consisting of, the following amino acid sequence: MERLTLTRTIG-GPLLTATLLGKTTINDYQVIRMPFSHL-STYSLVWVMAAVVLC TAQVQVVTQDEREQLYTPASLKCS-LQNAQEALIVTWQKKKAVSPENMVTFS ENHGVVIQ-PAYKDKINITQLGLQNSTITFWNITLE-DEGCYMCLFNTFGFGKISG TACLTVYVQPIVSLHYKFSEDHLNITC-SATARPAPMVFWKVPRSGIENSTVTL SHPNGTTS-VTSILHIKDPKNQVGKEVICQV-LHLGTVTDFKQTVNKGYWFSVPL LLSIVSLVILLVLISILLYWKRHRNQDREP (SEQ ID NO:2; Genbank Accession No. NP_001004196.2). SEQ ID NO:2 depicts the amino acid sequence of a full-length CD200 isoform B protein. In some embodiments, the anti-CD200 antibody binds to an epitope present in a human CD200 protein having the following amino acid sequence: VIRM-PFSHLSTYSLVWVMAAVVLCTAQVQV-VTQDEREQLYTTASLKCSLQN AQEALIVTWQKKKAVSPENMVTFSENH-GVVIQPAYKDKINITQLGLQNSTITF WNITLEDEG-CYMCLFNTFGFGKISGTACLTVYVQPIV-SLHYKFSEDHLNITCS ATARPAPMVFWKVPRSGIENSTVTLSHP-NGTTSVTSILHIKDPKNQVGKEVIC QVLHLGTVTD-FKQTVNKGYWFSVPLLLSIVSLVILLV-LISILLYWKRHRNQDR GELSQGVQKMT (SEQ ID NO:3; Genbank Accession No. CAA28943.1; FIG. 3 of McCaughan et al. (1987) *Immunogenetics* 25:329-335). SEQ ID NO:3 is an exemplary sequence for a full-length human CD200 protein.

In some embodiments, an anti-CD200 antibody described herein binds to an epitope within the extracellular portion of a CD200 protein. For example, in some embodiments, the anti-CD200 antibody can bind to CD200 protein at an epitope within or overlapping with: (i) amino acids 1 to 233 of the amino acid sequence depicted in SEQ ID NO:1; (ii) amino acids 1 to 258 of the amino acid sequence depicted in SEQ ID NO:2; or amino acids 1 to 229 of the amino acid sequence depicted in SEQ ID NO:3.

In some embodiments, the anti-CD200 antibody binds to an epitope in the human CD200 protein lacking the leader sequence. For example, an anti-CD200 antibody described herein can bind to a CD200 protein at an epitope within or overlapping with amino acids 31 to 233 of the amino acid sequence depicted in SEQ ID NO:1, which corresponds to the extracellular portion of the mature form of human CD200 isoform A less the amino terminal leader sequence. In some embodiments, an anti-CD200 antibody described herein can bind to a CD200 protein at an epitope within or overlapping with amino acids 56 to 258 of the amino acid sequence depicted in SEQ ID NO:2, which corresponds to the extracellular portion of the mature form of human CD200 isoform B less the amino terminal leader sequence. In some embodiments, an anti-CD200 antibody described herein can bind to a CD200 protein at an epitope within or overlapping with amino acids 27 to 229 of the amino acid sequence depicted in SEQ ID NO:3, which corresponds to the extracellular portion of the mature form of human CD200 less the amino terminal leader sequence.

An "epitope" refers to the site on a protein (e.g., a human CD200 protein) that is bound by an antibody. "Overlapping epitopes" include at least one (e.g., two, three, four, five, or six) common amino acid residue(s).

In some embodiments, the anti-CD200 antibody specifically binds to a human CD200 protein (e.g., the human CD200 protein having the amino acid sequence depicted in SEQ ID NO:1, SEQ ID NO:2, SEQ ID NO:3, or the extracellular domains of the mature forms of the CD200 proteins). The terms "specific binding" or "specifically binds" refer to two molecules forming a complex (e.g., a complex between an anti-CD200 antibody and a CD200 protein) that is relatively stable under physiologic conditions. Typically, binding is considered specific when the association constant ($K_a$) is higher than $10^6$ M$^{-1}$. Thus, an anti-CD200 antibody can specifically bind to a CD200 protein with a $K_a$ of at least (or greater than) $10^6$ (e.g., at least or greater than $10^7$, $10^8$, $10^9$, $10^{10}$, $10^{11}$ $10^{12}$, $10^{13}$, $10^{14}$, or $10^{15}$ or higher) M$^{-1}$. Examples of antibodies that specifically bind to a human CD200 protein are described in, e.g., U.S. Pat. Nos. 7,408,041; 7,427,665; 7,435,412; and 7,598,353, the disclosures of each of which are incorporated herein by reference in their entirety.

The amino acid sequences for several exemplary anti-CD200 antibodies are described in, e.g., U.S. Pat. No. 7,408, 041. For example, the anti-CD200 antibody can comprise the amino acid sequence of the heavy and light chain variable regions of one of the Fab antibodies—d1B10, d1A5, d1B5, c2aB7, c1A10, or c2aA10—depicted in FIG. 23 of U.S. Pat. No. 7,408,041, the sequences depicted in FIG. 23 being incorporated herein by reference in their entirety. In some embodiments, an anti-CD200 antibody described herein contains a paired set of heavy chain CDRs and light chain CDRs of one of the Fab antibodies depicted in FIG. 23 of U.S. Pat. No. 7,408,041. For example, an anti-CD200 antibody described herein contains the paired set of CDRs from the d1B10 Fab antibody: a heavy chain CDR1 (HCDR1) comprising the following sequence: GFTFSGFAMS (SEQ ID NO:4); a heavy chain CDR2 (HCDR2) comprising the following sequence: SISSGGTTYYLDSVKG (SEQ ID NO:5); a heavy chain CDR3 (HCDR3) comprising the following sequence: GNYYSGTSYDY (SEQ ID NO:6); a light chain CDR1 (LCDR1) comprising the following sequence: RASESVDSYGNSFMH (SEQ ID NO:7); a light chain CDR2 (LCDR2) comprising the following sequence: RASNLES (SEQ ID NO:8); and a light chain CDR3 (LCDR3) comprising the following sequence: QQSNEDPRT (SEQ ID NO:9).

In another example, an anti-CD200 antibody described herein can contain the paired set of CDRs from the d1A5 Fab antibody: (i) a HCDR1 comprising the following sequence: GFNIKDYYMH (SEQ ID NO:10); a HCDR2 comprising the following sequence: WIDPENGDTKYAPKFQG (SEQ ID NO:11); a HCDR3 comprising the following sequence: KNYYVSNYNFFDV (SEQ ID NO:12); a LCDR1 comprising the following sequence: SASSSVRYMY (SEQ ID NO:13); a LCDR2 comprising the following sequence: DTSKLAS (SEQ ID NO:14); and a LCDR3 comprising the following sequence: FQGSGYPLT (SEQ ID NO:15).

In another example, an anti-CD200 antibody described herein can comprise the paired set of CDRs from the d1B5 Fab antibody: a HCDR1 comprising the following amino acid sequence: GFNIKDYYIH (SEQ ID NO:16); a HCDR2 comprising the following amino acid sequence: WIDPEIGATKYVPKFQG (SEQ ID NO:17); a HCDR3 comprising the following amino acid sequence: LYGNYDRYYAMDY (SEQ ID NO:18); a LCDR1 comprising the following amino acid sequence: KASQNVRTAVA (SEQ ID NO:19); a LCDR2 comprising the following amino acid sequence: LASNRHT (SEQ ID NO:20); and a LCDR3 comprising the following amino acid sequence: LQHWNYPLT (SEQ ID NO:21).

In another example, an anti-CD200 antibody described herein can contain the paired set of CDRs from the c2aB7 Fab antibody: a HCDR1 comprising the amino acid sequence: GYSFTDYIIL (SEQ ID NO:22); a HCDR2 comprising the amino acid sequence: HIDPYYGSSNYNLKFKG (SEQ ID NO:23); a HCDR3 comprising the amino acid sequence: SKRDYFDY (SEQ ID NO:24); a LCDR1 comprising the amino acid sequence: KASQDINSYLS (SEQ ID NO:25); a LCDR2 comprising the amino acid sequence: RANRLVD (SEQ ID NO:26); and a LCDR3 comprising the amino acid sequence: LQYDEFPYT (SEQ ID NO:27). Samalizumab (ALXN6000) contains the aforementioned paired CDR set of the c2aB7 Fab antibody originally set forth in FIG. 23 of U.S. Pat. No. 7,408,041.

In yet another example, an anti-CD200 antibody described herein can contain a paired set of CDRs from the c1A10 Fab antibody: a HCDR1 comprising the amino acid sequence: GYTFTEYTMH (SEQ ID NO:28); a HCDR2 comprising the amino acid sequence: GVNPNNGGALYNQKFKG (SEQ ID NO:29); a HCDR3 comprising the amino acid sequence: RSNYRYDDAMDY (SEQ ID NO:30); a LCDR1 comprising the amino acid sequence: KSSQSLLDIDEKTYLN (SEQ ID NO:31); a LCDR2 comprising the amino acid sequence: LVSKLDS (SEQ ID NO:32); and a LCDR3 comprising the amino acid sequence: WQGTHFPQT (SEQ ID NO:33).

And in yet another example, an anti-CD200 antibody described herein can contain a paired set of CDRs from the c2aA10 Fab antibody: a HCDR1 comprising the amino acid sequence: AFNIKDHYMH (SEQ ID NO:34); a HCDR2 comprising the amino acid sequence: WIDPESGDTEYAPKFQG (SEQ ID NO:35); a HCDR3 comprising the amino acid sequence: FNGYQALDQ (SEQ ID NO:36); a LCDR1 comprising the amino acid sequence: TASSSVSSSYLH (SEQ ID NO:37); a LCDR2 comprising the amino acid sequence: STSNLAS (SEQ ID NO:38); and a LCDR3 comprising the amino acid sequence: RQYHRSPPIFT (SEQ ID NO:39).

Additional exemplary sets of CDRs of anti-CD200 antibodies are described in, e.g., U.S. Pat. No. 7,427,665. In some embodiments, the anti-CD200 antibody is samalizumab (ALXN6000).

Methods for determining whether an antibody binds to a protein antigen and/or the affinity for an antibody to a protein antigen are known in the art. For example, the binding of an antibody to a protein antigen can be detected and/or quantified using a variety of techniques such as, but not limited to, Western blot, dot blot, surface plasmon resonance method (e.g., BIAcore system; Pharmacia Biosensor AB, Uppsala, Sweden and Piscataway, N.J.), or enzyme-linked immunosorbent assay (ELISA). See, e.g., Harlow and Lane (1988) "Antibodies: A Laboratory Manual" Cold Spring Harbor Laboratory Press, Cold Spring Harbor, N.Y.; Benny K. C. Lo (2004) "Antibody Engineering: Methods and Protocols," Humana Press (ISBN: 1588290921); Borrebaek (1992) "Antibody Engineering, A Practical Guide," W.H. Freeman and Co., NY; Borrebaek (1995) "Antibody Engineering," $2^{nd}$ Edition, Oxford University Press, NY, Oxford; Johne et al. (1993) *J Immunol Meth* 160:191-198; Jonsson et al. (1993) *Ann Biol Clin* 51:19-26; and Jonsson et al. (1991) *Biotechniques* 11:620-627.

In some embodiments, the anti-CD200 antibody can cross-block binding of another antibody that binds to an epitope within, or overlapping with, a human CD200 protein. In some embodiments, the anti-CD200 antibody can crossblock binding of an antibody that binds to an epitope within, or overlapping with, a peptide fragment of a human CD200 protein. The peptide fragment can be a fragment of a human CD200 protein having the amino acid sequence depicted in, e.g., any one of SEQ ID NOs:1 to 3. As used herein, the term "crossblocking antibody" refers to an antibody that lowers the amount of binding of anti-CD200 antibody to an epitope on a CD200 protein relative to the amount of binding of the anti-CD200 antibody to the epitope in the absence of the antibody. Suitable methods for determining whether a first antibody crossblocks binding of a second antibody to an epitope are known in the art.

Methods for identifying the epitope to which a particular antibody (e.g., an anti-CD200 antibody) binds are also known in the art. For example, the binding epitope of an anti-CD200 antibody can be identified by measuring the binding of the antibody to several (e.g., three, four, five, six, seven, eight, nine, 10, 15, 20, or 30 or more) overlapping peptide fragments of a CD200 protein (e.g., several overlapping fragments of a protein having the amino acid sequence depicted in, e.g., any one of SEQ ID NOs:1 to 3). Each of the different overlapping peptides is then bound to a unique address on a solid support, e.g., separate wells of a multi-well assay plate. Next, the anti-CD200 antibody is interrogated by contacting it to each of the peptides in the assay plate for an amount of time and under conditions that allow for the antibody to bind to its epitope. Unbound anti-CD200 antibody is removed by washing each of the wells. Next, a detectably-labeled secondary antibody that binds to the anti-CD200 antibody, if present in a well of the plate, is contacted to each of the wells, and unbound secondary antibody is removed by washing steps. The presence or amount of the detectable signal produced by the detectably-labeled secondary antibody in a well is an indication that the anti-CD200 antibody binds to the particular peptide fragment associated with the well. See, e.g., Harlow and Lane (supra), Benny K. C. Lo (supra), and U.S. Patent Application Publication No. 20060153836, the disclosure of which is incorporated by reference in its entirety. A particular epitope to which an antibody binds can also be identified using BIAcore chromatographic techniques (see, e.g., Pharmacia BIAtechnology Handbook, "Epitope Mapping," Section 6.3.2, (May 1994); and Johne et al. (1993) *J Immunol Methods* 160:20191-8).

In some embodiments, an anti-CD200 antibody, or a CD200-binding fragment thereof, described herein binds to a human CD200 polypeptide expressed on the surface of a cell. Methods for determining whether an antibody binds to a protein expressed on the surface of a cell are known in the art and described in, e.g., Petermann et al. (2007) *J Clin Invest* 117(12):3922-9; Rijkers et al. (2008) *Mol Immunol* 45(4): 1126-35; and Kretz-Rommel (2007) *J Immunol* 178(9):5595-605.

In some embodiments, an anti-CD200 antibody or CD200-binding fragment thereof described herein inhibits the interaction between CD200 protein and the CD200 receptor. Methods for determining whether an agent (such as an antibody) inhibits the interaction between CD200 and CD200R are known in the art and described in, e.g., Hatherly and Barclay (2004) *Eur J Immunol* 34(6):1688-94.

In some embodiments, the anti-CD200 antibody or CD200-binding fragment thereof inhibits the formation of osteoclasts in vitro and/or in vivo. Suitable methods for determining whether an antibody inhibits the formation of osteoclasts are known in the art and described in, e.g., PCT Publication No. WO 2008/089022 and Cui et al. (2007) *Proc Natl Acad Sci USA* 104(36):14436-14441. For example, murine bone marrow cells can be cultured in the presence of, e.g., RANKL and M-CSF in the presence or absence of an anti-CD200 antibody. A decrease in the percentage of osteoclasts formed from the bone marrow cells in the presence of the antibody as compared to the percentage of osteoclasts formed in the absence of the antibody indicates that the antibody inhibits osteoclast formation in vitro.

Since CD200 is expressed on normal cells such as endothelial cells, albeit at lower levels than on cancer cells, it could be in some embodiments advantageous to administer a variant anti-CD200 antibody (or CD200-binding fragment thereof) with a constant region modified so that it does not mediate, or has decreased ability to mediate, antibody-dependent cell-mediated cytotoxicity (ADCC), whereby antibodies bind Fc receptors on natural killer (NK) cells or macrophages leading to cell death, or complement-dependent cytotoxicity (CDC), which is cell death induced via activation of the complement cascade (reviewed in Daeron (1997) *Annu Rev Immunol* 15:203-234; Ward and Ghetie (1995) *Therapeutic Immunol* 2:77-94; and Ravetch and Kinet (1991) *Annu Rev Immunol.* 9:457-492). Such a modification would be useful to limit damage to normal cells. CD200 expression is also upregulated on some activated normal cells (e.g., activated T cells), rendering such cells vulnerable to killing by an anti-CD200 antibody with effector function. It may be advantageous to use an anti-CD200 antibody lacking effector function to avoid killing of these cells by ADCC or CDC. The effector function of an anti-CD200 antibody can be eliminated by replacing an immunoglobulin constant region that has effector function (e.g., the IgG1 constant domain) for a constant region that does not have effector function (e.g., an IgG2/IgG4 fusion constant region). See, e.g., Burton et al. (1992) *Adv Immun* 51:1-18; Canfield et al. (1991) *J Exp Med* 173:1483-1491; and Mueller et al. (1997) *Mol Immunol* 34(6):441-452). For example (and in accordance with Kabat numbering), the IgG1 and IgG4 constant regions contain $G_{249}G_{250}$ residues whereas the IgG2 constant region does not contain residue 249, but does contain $G_{250}$. In a G2/G4 hybrid constant region, where the 249-250 region comes from the G2 sequence, the constant region can be further modified to introduce a glycine residue at position 249 to produce a G2/G4 fusion having $G_{249}/G_{250}$. Additional methods for eliminating effector function are described below.

It is understood that any of the above-described anti-CD200 antibodies can be incorporated into the bispecific anti-CD200/anti-CD20 antibodies described herein.

Anti-CD20 Therapeutic Agents

The disclosure also features therapeutic agents that specifically target cells (e.g., cancer cells) that express CD20 protein by specifically binding to CD20 on the surface of the cells. The anti-CD20 therapeutic can be, e.g., a small molecule compound that binds to CD20, a protein (e.g., a natural or synthetic ligand for CD20) or fragment thereof, an RNA aptamer, an L-RNA aptamer, or a spiegelmer.

In some embodiments, the anti-CD20 therapeutic agents are antibodies that bind to CD20 polypeptides (sometimes the antibodies are referred to herein as "anti-CD20 antibodies"). Also featured are antigen-binding (CD20-binding) fragments of the antibodies. In some embodiments, an anti-CD20 antibody described herein binds to an epitope in the human CD20 protein. For example, the anti-CD20 antibody can bind to an epitope in the human CD20 protein comprising, or consisting of, the following amino acid sequence: MTTPRNSVNGTF-PAEPMKGPIAMQSGPKPLFRRMSS-LVGPTQSFFMRESKTLG AVQIMNGLFHIALGGLLMI-PAGIYAPICVTVWYPLWGGIMYIISGSLLAATEK NSRKCLVKGKMIMNSLSLFAAISGMIL-SIMDILNIKISHFLKMESLNFIRAHTPY INIYNCE-PANPSEKNSPSTQYCYSIQSLFLGILS-VMLIFAFFQELVIAGIVENEWK RTCSRPKSNIVLLSAEEKKEQTIE-IKEEVVGLTETSSQPKNEEDIEIIPIQEEEEEE TETNF-PEPPQDQESSPIENDSSP (SEQ ID NO:40; Genbank Accession No. NP_068769.2). SEQ ID NO:40 depicts the amino acid sequence for a full-length, precursor human CD20 isoform A protein. The amino acid sequence for a full-length human CD20 polypeptide is also described in, e.g., Tedder et al. (1988) *Proc Natl Acad Sci USA* 85(1):208-212.

An anti-CD20 antibody described herein binds to an epitope within the extracellular portion of a CD20 protein. For example, in some embodiments, the anti-CD20 antibody can bind to CD20 protein at an epitope within or overlapping with: (i) amino acids 72 to 80 of the amino acid sequence depicted in SEQ ID NO:40; or (ii) amino acids 140 to 186 of the amino acid sequence depicted in SEQ ID NO:40. See, e.g., Teeling et al. (2006) *J Immunol* 177:362-367. That is, an anti-CD20 antibody described herein can bind to an epitope of human CD20 within or overlapping with the amino acid sequence IPAGIYAPI (SEQ ID NO:41) or NIKISHFLK-MESLNFIRAHTPYINIYNCEPANPSEKNSPSTQYCYSI (SEQ ID NO:42).

In some embodiments, the anti-CD20 antibody specifically binds to a human CD20 protein (e.g., the human CD20 protein having the amino acid sequence depicted in SEQ ID NO:40 or one or more of the extracellular loops of the human CD20 protein). Examples of antibodies that specifically bind to a human CD20 protein are described in, e.g., Teeling et al. (2006) at 363, supra; Levene et al. (2005) *JR Soc Med* 98:146-152; and U.S. Pat. Nos. 7,435,803; 5,595,721; and 7,422,739, the disclosures of each of which are incorporated herein by reference in their entirety.

Exemplary therapeutic anti-CD20 antibodies, which are approved for clinical use or are in clinical development, that can be used in the methods described herein include, without limitation, rituximab (Biogen Idec), $^{90}$Y-ibntumomab tiuxetan (Biogen Idec), $^{131}$I-tositumomab (GlaxoSmithKline), ofatumumab (Genmab), TRU-015 (Trubion), veltuzumab (IMMU-106; Immunomedics), ocrelizumab (Roche), and AME-133v (Applied Molecular Evolution). See, e.g., Levene et al. (2005), supra; Burge et al. (2008) *Clin Ther* 30(10): 1806-1816; Kausar et al. (2009) *Expert Opin Biol Ther* 9(7): 889-895; Morschhauser et al. (2009) *J Clin Oncol* 27(20): 3346-3353; and Milani and Castillo (2009) *Curr Opin Mol Ther* 11(2):200-207.

Methods for determining whether an antibody binds to CD20 and/or the affinity of an antibody for CD20 are known in the art. In some embodiments, the anti-CD20 antibody can crossblock binding of another antibody that binds to an epitope within, or overlapping with, a human CD20 protein. In some embodiments, the anti-CD20 antibody can cross-block binding of an antibody that binds to an epitope within, or overlapping with, a peptide fragment of a human CD20 protein. The peptide fragment can be a fragment of a human CD200 protein having the amino acid sequence depicted in, e.g., any one of SEQ ID NO:41 or SEQ ID NO:42.

It is understood that any of the above-described anti-CD200 antibodies can be incorporated into the bispecific anti-CD200/anti-CD20 antibodies described herein.

Pharmaceutical Compositions and Formulations

The compositions containing an anti-CD200 antibody, an anti-CD20 therapeutic agent such as an anti-CD20 antibody, or both, can be formulated as a pharmaceutical composition, e.g., for administration to a human to treat cancer or an autoimmune disorder. The pharmaceutical compositions will generally include a pharmaceutically acceptable carrier. As used herein, a "pharmaceutically acceptable carrier" refers to, and includes, any and all solvents, dispersion media, coatings, antibacterial and antifungal agents, isotonic and absorption delaying agents, and the like that are physiologically compatible. The compositions can include a pharmaceutically acceptable salt, e.g., an acid addition salt or a base addition salt. See, e.g., Berge et al. (1977) *J Pharm Sci* 66:1-19.

The compositions can be formulated according to standard methods. Pharmaceutical formulation is a well-established art, and is further described in, e.g., Gennaro (2000) "Remington: The Science and Practice of Pharmacy," 20th Edition, Lippincott, Williams & Wilkins (ISBN: 0683306472); Ansel et al. (1999) "Pharmaceutical Dosage Forms and Drug Delivery Systems," 7th Edition, Lippincott Williams & Wilkins Publishers (ISBN: 0683305727); and Kibbe (2000) "Handbook of Pharmaceutical Excipients American Pharmaceutical Association," 3rd Edition (ISBN: 091733096X). In some embodiments, a composition can be formulated, for example, as a buffered solution at a suitable concentration and suitable for storage at 2-8° C. In some embodiments, a composition can be formulated for storage at a temperature below 0° C. (e.g., −20° C. or −80° C.).

The pharmaceutical compositions can be in a variety of forms. These forms include, e.g., liquid, semi-solid and solid dosage forms, such as liquid solutions (e.g., injectable and infusible solutions), dispersions or suspensions, tablets, pills, powders, liposomes and suppositories. The preferred form depends, in part, on the intended mode of administration and therapeutic application. For example, compositions containing an anti-CD200 antibody or an anti-CD20 antibody, intended for systemic or local delivery can be in the form of injectable or infusible solutions. Accordingly, the compositions can be formulated for administration by a parenteral mode (e.g., intravenous, subcutaneous, intraperitoneal, or intramuscular injection). "Parenteral administration," "administered parenterally," and other grammatically equivalent phrases, as used herein, refer to modes of administration other than enteral and topical administration, usually by injection, and include, without limitation, intravenous, intranasal, intraocular, pulmonary, intramuscular, intraarterial, intrathecal, intracapsular, intraorbital, intracardiac, intradermal, intrapulmonary, intraperitoneal, transtracheal, subcutaneous, subcuticular, intraarticular, subcapsular, subarachnoid, intraspinal, epidural, intracerebral, intracranial, intracarotid and intrasternal injection and infusion (see below).

The compositions can be formulated as a solution, microemulsion, dispersion, liposome, or other ordered structure suitable for stable storage at high concentration. Sterile injectable solutions can be prepared by incorporating an antibody described herein in the required amount in an appropriate solvent with one or a combination of ingredients enumerated above, as required, followed by filtered sterilization. Generally, dispersions are prepared by incorporating an anti-CD200 antibody (and/or an anti-CD20 therapeutic agent such as an anti-CD20 antibody) described herein into a sterile vehicle that contains a basic dispersion medium and the required other ingredients from those enumerated above. In the case of sterile powders for the preparation of sterile injectable solutions, methods for preparation include vacuum drying and freeze-drying that yield a powder of the antibody described herein plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition a reagent that delays absorption, for example, monostearate salts and gelatin.

In certain embodiments, the anti-CD200 antibody (and/or the anti-CD20 therapeutic agent such as an anti-CD20 antibody) can be prepared with a carrier that will protect the compound against rapid release, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are known in the art. (See, e.g., J. R. Robinson (1978) "Sustained and Controlled Release Drug Delivery Systems," Marcel Dekker, Inc., New York.)

In some embodiments, an antibody described herein can be formulated in a composition suitable for intrapulmonary administration (e.g., for administration via nebulizer) to a mammal such as a human. Methods for preparing such compositions are well known in the art and described in, e.g., U.S. Patent Application Publication No. 20080202513; U.S. Pat. Nos. 7,112,341 and 6,019,968; and PCT Publication Nos. WO 00/061178 and WO 06/122257, the disclosures of each of which are incorporated herein by reference in their entirety. Dry powder inhaler formulations and suitable systems for administration of the formulations are described in, e.g., U.S. Patent Application Publication No. 20070235029, PCT Publication No. WO 00/69887; and U.S. Pat. No. 5,997,848.

In some embodiments, an anti-CD200 antibody (and/or an anti-CD20 therapeutic agent such as an anti-CD20 antibody) described herein can be modified, e.g., with a moiety that improves its stabilization and/or retention in circulation, e.g., in blood, serum, or other tissues. The stabilization moiety can improve the stability, or retention of, the antibody by at least 1.5 (e.g., at least 2, 5, 10, 15, 20, 25, 30, 40, or 50 or more) fold.

In some embodiments, an anti-CD200 antibody described herein can be formulated with one or more additional active agents useful for treating cancer or ameliorating a symptom thereof. For example, an anti-CD200 antibody can be formulated with an anti-CD20 therapeutic agent (e.g., an anti-CD20 antibody such as any of the anti-CD20 antibodies described herein), a genotoxic agent or a chemotherapeutic agent, or one or more kinase inhibitors. The genotoxic or chemotherapeutic agent can be, but is not limited to: carboplatin, procarbazine, mechlorethamine, cyclophosphamide, camptothecin, ifosfamide, melphalan, chlorambucil, bisulfan, nitrosurea, dactinomycin, daunorubicin, doxorubicin, bleomycin, plicomycin, mitomycin, etoposide, podophyllotoxin, taxol, satraplatinum, 5-fluorouracil, vincristin, vinblastin, methotrexate, ara-C, taxotere, gemcitabine, cisplatin (CDDP), adriamycin (ADR), or an analog of any of the aforementioned. Kinase inhibitors include, e.g., one or more of: trastuzumab, gefitinib, erlotinib, imatinib mesylate, or sunitinib malate. Additional agents are known in the art and described herein.

When the anti-CD200 antibody is to be used in combination with a second active agent, or when two or more different anti-CD200 antibodies are to be used, the agents can be formulated separately or together. For example, the respective pharmaceutical compositions can be mixed, e.g., just prior to administration, and administered together or can be administered separately, e.g., at the same or different times (see below).

As described above, a composition can be formulated such that it includes a therapeutically effective amount of an anti-CD200 antibody or the composition can be formulated to include a sub-therapeutic amount of the antibody and a sub-therapeutic amount of one or more additional active agents such that the components in total are therapeutically effective for treating a cancer or an autoimmune disorder. In some embodiments, a composition can be formulated to include two or more anti-CD200 antibodies, each at sub-therapeutic doses, such that the antibodies in combination are at a concentration that is therapeutically effective for treating a cancer or an autoimmune disorder in a human. Methods for determining a therapeutically effective dose of an anti-CD200 antibody are known in the art and described herein.

Methods for Producing an Anti-CD200 or an Anti-CD20 Antibody

Suitable methods for producing an antibody (e.g., an anti-CD200 antibody or an anti-CD20 antibody) or antigen-binding fragments thereof, in accordance with the disclosure are known in the art (see, e.g., U.S. Pat. Nos. 7,427,665; 7,435,412; and 7,408,041, the disclosures of each of which are incorporated herein by reference in their entirety) and described herein. For example, monoclonal anti-CD200 antibodies may be generated using human CD200-expressing cells, a human CD200 polypeptide, or an antigenic fragment of a human CD200 polypeptide as an immunogen, thus raising an immune response in animals from which antibody-producing cells and in turn monoclonal antibodies may be isolated. Similarly, a monoclonal anti-CD20 antibody can be generated using human CD20-expressing cells, a human CD20 polypeptide, or an antigenic fragment of the human CD20 polypeptide as an immunogen in an animal. The sequence of such antibodies may be determined and the antibodies or variants thereof produced by recombinant techniques. Recombinant techniques may be used to produce chimeric, CDR-grafted, humanized and fully human antibodies based on the sequence of the monoclonal antibodies as well as polypeptides capable of binding to the antigen of interest (e.g., CD200 or CD20).

Moreover, anti-CD200 antibodies derived from recombinant libraries ("phage antibodies") may be selected using CD200-expressing cells, or polypeptides derived therefrom, as bait to isolate the antibodies or polypeptides on the basis of target specificity. The production and isolation of non-human and chimeric anti-CD200 antibodies are well within the purview of the skilled artisan. It is understood that anti-CD20 antibodies can be selected using merely routine adaptations of the methods described above.

Recombinant DNA technology can be used to modify one or more characteristics of the antibodies produced in non-human cells. Thus, chimeric antibodies can be constructed in order to decrease the immunogenicity thereof in diagnostic or therapeutic applications. Moreover, immunogenicity can be minimized by humanizing the antibodies by CDR grafting and, optionally, framework modification. See, U.S. Pat. Nos. 5,225,539 and 7,393,648, the contents of each of which are incorporated herein by reference.

Antibodies can be obtained from animal serum or, in the case of monoclonal antibodies or fragments thereof, produced in cell culture. Recombinant DNA technology can be used to produce the antibodies according to established procedure, including procedures in bacterial or preferably mammalian cell culture. The selected cell culture system preferably secretes the antibody product.

In another embodiment, a process for the production of an antibody disclosed herein includes culturing a host, e.g. *E. coli* or a mammalian cell, which has been transformed with a hybrid vector. The vector includes one or more expression cassettes containing a promoter operably linked to a first DNA sequence encoding a signal peptide linked in the proper reading frame to a second DNA sequence encoding the antibody protein. The antibody protein is then collected and isolated. Optionally, the expression cassette may include a promoter operably linked to a polycistronic (e.g., bicistronic) DNA sequence encoding antibody proteins each individually operably linked to a signal peptide in the proper reading frame.

Multiplication of hybridoma cells or mammalian host cells in vitro is carried out in suitable culture media, which include the customary standard culture media (such as, for example Dulbecco's Modified Eagle Medium (DMEM) or RPMI 1640 medium), optionally replenished by a mammalian serum (e.g. fetal calf serum), or trace elements and growth sustaining supplements (e.g. feeder cells such as normal mouse peritoneal exudate cells, spleen cells, bone marrow macrophages, 2-aminoethanol, insulin, transferrin, low density lipoprotein, oleic acid, or the like). Multiplication of host cells which are bacterial cells or yeast cells is likewise carried out in suitable culture media known in the art. For example, for bacteria suitable culture media include medium LE, NZCYM, NZYM, NZM, Terrific Broth, SOB, SOC, 2×YT, or M9 Minimal Medium. For yeast, suitable culture media include medium YPD, YEPD, Minimal Medium, or Complete Minimal Dropout Medium.

In vitro production provides relatively pure antibody preparations and allows scale-up production to give large amounts of the desired antibodies. Techniques for bacterial cell, yeast, plant, or mammalian cell cultivation are known in the art and include homogeneous suspension culture (e.g. in an airlift reactor or in a continuous stirrer reactor), and immobilized or entrapped cell culture (e.g. in hollow fibers, microcapsules, on agarose microbeads or ceramic cartridges).

Large quantities of the desired antibodies can also be obtained by multiplying mammalian cells in vivo. For this purpose, hybridoma cells producing the desired antibodies are injected into histocompatible mammals to cause growth of antibody-producing tumors. Optionally, the animals are primed with a hydrocarbon, especially mineral oils such as pristane (tetramethyl-pentadecane), prior to the injection. After one to three weeks, the antibodies are isolated from the body fluids of those mammals. For example, hybridoma cells obtained by fusion of suitable myeloma cells with antibody-producing spleen cells from Balb/c mice, or transfected cells derived from hybridoma cell line Sp2/0 that produce the desired antibodies are injected intraperitoneally into Balb/c mice optionally pre-treated with pristane. After one to two weeks, ascitic fluid is taken from the animals.

The foregoing, and other, techniques are discussed in, for example, Kohler and Milstein, (1975) *Nature* 256:495-497; U.S. Pat. No. 4,376,110; Harlow and Lane, Antibodies: a Laboratory Manual, (1988) Cold Spring Harbor, the disclosures of which are all incorporated herein by reference. Techniques for the preparation of recombinant antibody molecules are described in the above references and also in, e.g.: WO97/08320; U.S. Pat. No. 5,427,908; U.S. Pat. No. 5,508,717; Smith (1985) *Science* 225:1315-1317; Parmley and Smith (1988) *Gene* 73:305-318; De La Cruz et al. (1988) *Journal of Biological Chemistry* 263:4318-4322; U.S. Pat. No. 5,403,484; U.S. Pat. No. 5,223,409; WO88/06630; WO92/15679; U.S. Pat. No. 5,780,279; U.S. Pat. No. 5,571,698; U.S. Pat. No. 6,040,136; Davis et al. (1999) *Cancer Metastasis Rev.* 18(4):421-5; and Taylor et al. (1992) *Nucleic Acids Research* 20: 6287-6295; Tomizuka et al. (2000) *Proc. Natl. Acad. Sci. USA* 97(2): 722-727, the contents of each of which are incorporated herein by reference in their entirety.

The cell culture supernatants are screened for the desired antibodies, preferentially by immunofluorescent staining of CD200-expressing cells, by immunoblotting, by an enzyme immunoassay, e.g. a sandwich assay or a dot-assay, or a radioimmunoassay.

For isolation of the antibodies, the immunoglobulins in the culture supernatants or in the ascitic fluid may be concentrated, e.g., by precipitation with ammonium sulfate, dialysis against hygroscopic material such as polyethylene glycol, filtration through selective membranes, or the like. If necessary and/or desired, the antibodies are purified by the customary chromatography methods, for example gel filtration, ion-exchange chromatography, chromatography over DEAE-cellulose and/or (immuno-) affinity chromatography, e.g., affinity chromatography with one or more surface polypeptides derived from a CD200-expressing cell line or synthetic CD200 fragment peptides, or with Protein-A or -G.

Another embodiment provides a process for the preparation of a bacterial cell line secreting antibodies directed against a human CD200 protein or a human CD20 (depending on the antibody being generated) in a suitable mammal. For example a rabbit is immunized with pooled samples from CD200-expressing tissue or cells or CD200 polypeptide or fragments thereof. A phage display library produced from the immunized rabbit is constructed and panned for the desired antibodies in accordance with methods well known in the art (such as, e.g., the methods disclosed in the various references incorporated herein by reference).

Hybridoma cells secreting the monoclonal antibodies are also disclosed. The preferred hybridoma cells are genetically stable, secrete monoclonal antibodies described herein of the desired specificity, and can be expanded from deep-frozen cultures by thawing and propagation in vitro or as ascites in vivo.

In another embodiment, a process is provided for the preparation of a hybridoma cell line secreting monoclonal antibodies against a human CD200 protein. In that process, a suitable mammal, for example a Balb/c mouse, is immunized with one or more polypeptides or antigenic fragments of CD200 or with one or more polypeptides or antigenic fragments derived from a CD200-expressing cell, the CD200-expressing cell itself, or an antigenic carrier containing a purified polypeptide as described. Antibody-producing cells of the immunized mammal are grown briefly in culture or fused with cells of a suitable myeloma cell line. The hybrid cells obtained in the fusion are cloned, and cell clones secreting the desired antibodies are selected. For example, spleen cells of Balb/c mice immunized with a protein fragment of human CD200 are fused with cells of the myeloma cell line PAI or the myeloma cell line Sp2/0-Ag 14. The obtained hybrid cells are then screened for secretion of the desired antibodies and positive hybridoma cells are cloned.

Methods for preparing a hybridoma cell line include immunizing Balb/c mice by injecting subcutaneously and/or intraperitoneally a peptide fragment of human CD200 several times, e.g., four to six times, over several months, e.g., between two and four months. Spleen cells from the immunized mice are taken two to four days after the last injection and fused with cells of the myeloma cell line PAI in the presence of a fusion promoter, preferably polyethylene glycol. Preferably, the myeloma cells are fused with a three- to twenty-fold excess of spleen cells from the immunized mice in a solution containing about 30% to about 50% polyethylene glycol of a molecular weight around 4000. After the fusion, the cells are expanded in suitable culture media as described supra, supplemented with a selection medium, for example HAT medium, at regular intervals in order to prevent normal myeloma cells from overgrowing the desired hybridoma cells.

The antibodies and fragments thereof can be "chimeric." Chimeric antibodies and antigen-binding fragments thereof comprise portions from two or more different species (e.g., mouse and human). Chimeric antibodies can be produced with mouse variable regions of desired specificity spliced into human constant domain gene segments (for example, U.S. Pat. No. 4,816,567). In this manner, non-human antibodies can be modified to make them more suitable for human clinical application (e.g., methods for treating or preventing a cancer in a human subject).

The monoclonal antibodies of the present disclosure include "humanized" forms of the non-human (e.g., mouse) antibodies. Humanized or CDR-grafted mAbs are particularly useful as therapeutic agents for humans because they are not cleared from the circulation as rapidly as mouse antibodies and do not typically provoke an adverse immune reaction. Generally, a humanized antibody has one or more amino acid residues introduced into it from a non-human source. These non-human amino acid residues are often referred to as "import" residues, which are typically taken from an "import" variable domain. Methods of preparing humanized antibodies are generally well known in the art. For example, humanization can be essentially performed following the method of Winter and co-workers (see, e.g., Jones et al. (1986) *Nature* 321:522-525; Riechmann et al. (1988) *Nature* 332:323-327; and Verhoeyen et al. (1988) *Science* 239:1534-1536), by substituting rodent CDRs or CDR sequences for the corresponding sequences of a human antibody. Also see, e.g., Staelens et al. (2006) *Mol Immunol* 43:1243-1257. In some embodiments, humanized forms of non-human (e.g., mouse) antibodies are human antibodies (recipient antibody) in which hypervariable (CDR) region residues of the recipient antibody are replaced by hypervariable region residues from a non-human species (donor antibody) such as a mouse, rat, rabbit, or non-human primate having the desired specificity, affinity, and binding capacity. In some instances, framework region residues of the human immunoglobulin are also replaced by corresponding non-human residues (so called "back mutations"). In addition, phage display libraries can be used to vary amino acids at chosen positions within the antibody sequence. The properties of a humanized antibody are also affected by the choice of the human framework. Furthermore, humanized and chimerized antibodies can be modified to comprise residues that are not found in the recipient antibody or in the donor antibody in order to further improve antibody properties, such as, for example, affinity or effector function.

Fully human antibodies are also provided in the disclosure. The term "human antibody" includes antibodies having variable and constant regions (if present) derived from human germline immunoglobulin sequences. Human antibodies can include amino acid residues not encoded by human germline immunoglobulin sequences (e.g., mutations introduced by random or site-specific mutagenesis in vitro or by somatic mutation in vivo). However, the term "human antibody" does not include antibodies in which CDR sequences derived from the germline of another mammalian species, such as a mouse, have been grafted onto human framework sequences (i.e., humanized antibodies). Fully human or human antibodies may be derived from transgenic mice carrying human antibody genes (carrying the variable (V), diversity (D), joining (J), and constant (C) exons) or from human cells. For example, it is now possible to produce transgenic animals (e.g., mice) that are capable, upon immunization, of producing a full repertoire of human antibodies in the absence of endogenous immunoglobulin production. See, e.g., Jakobovits et al. (1993) *Proc Natl Acad Sci USA* 90:2551; Jakobovits et al. (1993) *Nature* 362:255-258; Bruggemann et al. (1993) *Year in Immunol* 7:33; and Duchosal et al. (1992) *Nature* 355:258. Transgenic mouse strains can be engineered to contain gene sequences from unrearranged human immunoglobulin genes. The human sequences may code for both the heavy and light chains of human antibodies and would function correctly in the mice, undergoing rearrangement to provide a wide antibody repertoire similar to that in humans. The transgenic mice can be immunized with the target protein (e.g., a human CD200 protein, fragments thereof, or cells expressing CD200 protein; or a human CD20 protein, fragments thereof, or cells expressing CD20 protein) to create a diverse array of specific antibodies and their encoding RNA. Nucleic acids encoding the antibody chain components of such antibodies may then be cloned from the animal into a display vector. Typically, separate populations of nucleic acids encoding heavy and light chain sequences are cloned, and the separate populations then recombined on insertion into the vector, such that any given copy of the vector receives a random combination of a heavy and a light chain. The vector is designed to express antibody chains so that they can be assembled and displayed on the outer surface of a display package containing the vector. For example, antibody chains can be expressed as fusion proteins with a phage coat protein from the outer surface of the phage. Thereafter, display packages can be screened for display of antibodies binding to a target.

In addition, human antibodies can be derived from phage-display libraries (Hoogenboom et al. (1991) *J Mol Biol* 227: 381; Marks et al. (1991) *J Mol Biol* 222:581-597; and Vaughan et al. (1996) *Nature Biotech* 14:309 (1996)). Synthetic phage libraries can be created which use randomized combinations of synthetic human antibody V-regions. By selection on antigen fully human antibodies can be made in which the V-regions are very human-like in nature. See, e.g., U.S. Pat. Nos. 6,794,132, 6,680,209, 4,634,666, and Ostberg et al. (1983) *Hybridoma* 2:361-367, the contents of each of which are incorporated herein by reference in their entirety.

For the generation of human antibodies, also see Mendez et al. (1998) *Nature Genetics* 15:146-156, Green and Jakobovits (1998) *J Exp Med* 188:483-495, the disclosures of which are hereby incorporated by reference in their entirety. Human antibodies are further discussed and delineated in U.S. Pat. Nos. 5,939,598; 6,673,986; 6,114,598; 6,075,181; 6,162,963; 6,150,584; 6,713,610; and 6,657,103 as well as U.S. Patent Publication Nos. 20030229905 A1, 20040010810 A1, US 20040093622 A1, 20060040363 A1, 20050054055 A1, 20050076395 A1, 20050287630 A1. See also International Publication Nos. WO 94/02602, WO 96/34096, and WO 98/24893, and European Patent No. EP 0 463 151 B1. The disclosures of each of the above-cited patents, applications, and references are hereby incorporated by reference in their entirety.

In an alternative approach, others, including GenPharm International, Inc., have utilized a "minilocus" approach. In the minilocus approach, an exogenous Ig locus is mimicked through the inclusion of pieces (individual genes) from the Ig locus. Thus, one or more $V_H$ genes, one or more $D_H$ genes, one or more $J_H$ genes, a mu constant region, and a second constant region (preferably a gamma constant region) are formed into a construct for insertion into an animal. This approach is described in, e.g., U.S. Pat. Nos. 5,545,807; 5,545,806; 5,625, 825; 5,625,126; 5,633,425; 5,661,016; 5,770,429; 5,789,650; and 5,814,318; 5,591,669; 5,612,205; 5,721,367; 5,789,215; 5,643,763; 5,569,825; 5,877,397; 6,300,129; 5,874,299; 6,255,458; and 7,041,871, the disclosures of which are hereby incorporated by reference. See also European Patent No. 0 546 073 B1, International Patent Publication Nos. WO 92/03918, WO 92/22645, WO 92/22647, WO 92/22670, WO 93/12227, WO 94/00569, WO 94/25585, WO 96/14436, WO 97/13852, and WO 98/24884, the disclosures of each of which are hereby incorporated by reference in their entirety. See further Taylor et al. (1992) *Nucleic Acids Res* 20: 6287; Chen et al. (1993) *Int Immunol* 5: 647; Tuaillon et al. (1993) *Proc Natl Acad Sci USA* 90: 3720-4; Choi et al. (1993) *Nature Genetics* 4: 117; Lonberg et al. (1994) *Nature* 368: 856-859; Taylor et al. (1994) *International Immunology* 6: 579-591; Tuaillon et al. (1995) *J. Immunol.* 154: 6453-65; Fishwild et al. (1996) *Nature Biotechnology* 14: 845; and Tuaillon et al. (2000) *Eur J Immunol* 10: 2998-3005, the disclosures of each of which are hereby incorporated by reference in their entirety.

In certain embodiments, de-immunized anti-CD200 antibodies or antigen-binding fragments thereof are provided. De-immunized antibodies or antigen-binding fragments thereof are those modified so as to render the antibody or antigen-binding fragment thereof non-immunogenic, or less immunogenic, to a given species. De-immunization can be achieved by modifying the antibody or antigen-binding fragment thereof utilizing any of a variety of techniques known to those skilled in the art (see, e.g., PCT Publication Nos. WO 04/108158 and WO 00/34317). For example, an antibody or antigen-binding fragment thereof may be de-immunized by identifying potential T cell epitopes and/or B cell epitopes within the amino acid sequence of the antibody or antigen-binding fragment thereof and removing one or more of the potential T cell epitopes and/or B cell epitopes from the antibody or antigen-binding fragment thereof, for example, using recombinant techniques. The modified antibody or antigen-binding fragment thereof may then optionally be produced and tested to identify antibodies or antigen-binding fragments thereof that have retained one or more desired biological activities, such as, for example, binding affinity, but have reduced immunogenicity. Methods for identifying potential T cell epitopes and/or B cell epitopes may be carried out using techniques known in the art, such as, for example, computational methods (see e.g., PCT Publication No. WO 02/069232), in vitro or in silico techniques, and biological assays or physical methods (such as, for example, determination of the binding of peptides to MHC molecules, determination of the binding of peptide:MHC complexes to the T cell receptors from the species to receive the antibody or antigen-binding fragment thereof, testing of the protein or peptide parts thereof using transgenic animals with the MHC molecules of the species to receive the antibody or antigen-binding fragment thereof, or testing with transgenic animals reconstituted with immune system cells from the species to receive the antibody or antigen-binding fragment thereof, etc.). In various embodiments, the de-immunized antibodies (e.g., deimmunized anti-CD200 antibodies or deimmunized anti-CD20 antibodies) described herein include de-immunized antigen-binding fragments, Fab, Fv, scFv, Fab' and F(ab')$_2$, monoclonal antibodies, murine antibodies, engineered antibodies (such as, for example, chimeric, single chain, CDR-grafted, humanized, fully human antibodies, and artificially selected antibodies), synthetic antibodies and semi-synthetic antibodies.

In some embodiments, a recombinant DNA comprising an insert coding for a heavy chain variable domain and/or for a light chain variable domain of an anti-CD200 antibody or a CD200 protein-expressing cell line is produced. The term DNA includes coding single stranded DNAs, double stranded DNAs consisting of said coding DNAs and of complementary DNAs thereto, or these complementary (single stranded) DNAs themselves.

Furthermore, a DNA encoding a heavy chain variable domain and/or a light chain variable domain of anti-CD200 antibodies, or the CD200-expressing cell line, can be enzymatically or chemically synthesized to contain the authentic DNA sequence coding for a heavy chain variable domain and/or for the light chain variable domain, or a mutant thereof. A mutant of the authentic DNA is a DNA encoding a heavy chain variable domain and/or a light chain variable domain of the above-mentioned antibodies in which one or more amino acids are deleted, inserted, or exchanged with one or more other amino acids. Preferably said modification(s) are outside the CDRs of the heavy chain variable domain and/or of the light chain variable domain of the antibody in humanization and expression optimization applications. The term mutant DNA also embraces silent mutants wherein one or more nucleotides are replaced by other nucleotides with the new codons coding for the same amino acid(s). The term mutant sequence also includes a degenerate sequence. Degenerate sequences are degenerate within the meaning of the genetic code in that an unlimited number of nucleotides are replaced by other nucleotides without resulting in a change of the amino acid sequence originally encoded. Such degenerate sequences may be useful due to their different restriction sites and/or frequency of particular codons which are preferred by the specific host, particularly *E. coli*, to obtain an optimal expression of the heavy chain murine variable domain and/or a light chain murine variable domain.

The term mutant is intended to include a DNA mutant obtained by in vitro mutagenesis of the authentic DNA according to methods known in the art.

For the assembly of complete tetrameric immunoglobulin molecules and the expression of chimeric antibodies, the recombinant DNA inserts coding for heavy and light chain variable domains are fused with the corresponding DNAs coding for heavy and light chain constant domains, then transferred into appropriate host cells, for example after incorporation into hybrid vectors.

Recombinant DNAs including an insert coding for a heavy chain murine variable domain of an anti-CD200 antibody or a CD200-expressing cell line fused to a human constant domain IgG, for example γ1, γ2, γ3 or γ4, in particular embodiments γ1 or γ4, may be used. Recombinant DNAs including an insert coding for a light chain murine variable domain of an antibody fused to a human constant domain κ or λ, preferably κ, are also provided.

Another embodiment pertains to recombinant DNAs coding for a recombinant polypeptide wherein the heavy chain variable domain and the light chain variable domain are linked by way of a spacer group, optionally comprising a signal sequence facilitating the processing of the antibody in the host cell and/or a DNA sequence encoding a peptide facilitating the purification of the antibody and/or a cleavage site and/or a peptide spacer and/or an agent. The DNA coding for an agent is intended to be a DNA coding for the agent useful in diagnostic or therapeutic applications. Thus, agent molecules which are toxins or enzymes, especially enzymes capable of catalyzing the activation of prodrugs, are particularly indicated. The DNA encoding such an agent has the sequence of a naturally occurring enzyme or toxin encoding DNA, or a mutant thereof, and can be prepared by methods well known in the art.

Accordingly, the monoclonal antibodies or antigen-binding fragments of the disclosure can be naked antibodies or antigen-binding fragments that are not conjugated to other agents, for example, a therapeutic agent or detectable label. Alternatively, the monoclonal antibody or antigen-binding fragment can be conjugated to an agent such as, for example, a cytotoxic agent, a small molecule, a hormone, an enzyme, a growth factor, a cytokine, a ribozyme, a peptidomimetic, a chemical, a prodrug, a nucleic acid molecule including coding sequences (such as antisense, RNAi, gene-targeting constructs, etc.), or a detectable label (e.g., an NMR or X-ray contrasting agent, fluorescent molecule, etc.). In certain embodiments, an anti-CD200 antibody or antigen-binding fragment (e.g., Fab, Fv, single-chain scFv, Fab', and F(ab')$_2$) is linked to a molecule that increases the half-life of the antibody or antigen-binding fragment (see above).

Several possible vector systems are available for the expression of cloned heavy chain and light chain genes in mammalian cells. One class of vectors relies upon the integration of the desired gene sequences into the host cell genome. Cells which have stably integrated DNA can be selected by simultaneously introducing drug resistance genes such as *E. coli* gpt (Mulligan and Berg (1981) *Proc Natl Acad Sci USA*, 78:2072) or Tn5 neo (Southern and Berg (1982) *Mol Appl Genet.* 1:327). The selectable marker gene can be either linked to the DNA gene sequences to be expressed, or introduced into the same cell by co-transfection (Wigler et al. (1979) *Cell* 16:77). A second class of vectors utilizes DNA elements which confer autonomously replicating capabilities to an extrachromosomal plasmid. These vectors can be derived from animal viruses, such as bovine papillomavirus (Sarver et al. (1982) *Proc Natl Acad Sci USA*, 79:7147), polyoma virus (Deans et al. (1984) *Proc Natl Acad Sci USA* 81:1292), or SV40 virus (Lusky and Botchan (1981) *Nature* 293:79).

Since an immunoglobulin cDNA is comprised only of sequences representing the mature mRNA encoding an antibody protein, additional gene expression elements regulating transcription of the gene and processing of the RNA are required for the synthesis of immunoglobulin mRNA. These elements may include splice signals, transcription promoters, including inducible promoters, enhancers, and termination signals. cDNA expression vectors incorporating such elements include those described by Okayama and Berg (1983) *Mol Cell Biol* 3:280; Cepko et al. (1984) *Cell* 37:1053; and Kaufman (1985) *Proc Natl Acad Sci USA* 82:689.

As is evident from the disclosure, the anti-CD200 antibodies and/or anti-CD20 antibodies can be used in therapies (e.g., therapies for treating a cancer), including combination therapies, as well as in the monitoring of disease progression.

In the therapeutic embodiments of the present disclosure, bispecific antibodies are contemplated. Bispecific antibodies are monoclonal, preferably human or humanized, antibodies that have binding specificities for at least two different antigens. In the present case, one of the binding specificities is for the CD200 antigen on a cell (such as, e.g., an immune cell), the other one is for any other antigen, and preferably for a cell-surface protein or receptor or receptor subunit. In some embodiments, the bispecific antibody is one that binds to human CD200 and human CD20.

Methods for making bispecific antibodies are within the purview of those skilled in the art. Traditionally, the recombinant production of bispecific antibodies is based on the co-expression of two immunoglobulin heavy-chain/light-chain pairs, where the two heavy chains have different specificities (Milstein and Cuello (1983) *Nature* 305:537-539). Antibody variable domains with the desired binding specificities (antibody-antigen combining sites) can be fused to immunoglobulin constant domain sequences. The fusion preferably is with an immunoglobulin heavy-chain constant domain, including at least part of the hinge, $C_H2$, and $C_H3$ regions. DNAs encoding the immunoglobulin heavy-chain fusions and, if desired, the immunoglobulin light chain, are inserted into separate expression vectors, and are co-transfected into a suitable host organism. For further details of illustrative currently known methods for generating bispecific antibodies see, e.g., Suresh et al. (1986) *Methods in Enzymology* 121:210; PCT Publication No. WO 96/27011; Brennan et al. (1985) *Science* 229:81; Shalaby et al. *J Exp Med* (1992) 175:217-225; Kostelny et al. (1992) *J Immunol* 148(5):1547-1553; Hollinger et al. (1993) *Proc. Natl. Acad. Sci. USA* 90:6444-6448; Gruber et al. (1994) *J Immunol* 152: 5368; and Tutt et al. (1991) J Immunol 147:60. Bispecific antibodies also include cross-linked or heteroconjugate antibodies. Heteroconjugate antibodies may be made using any convenient cross-linking methods. Suitable cross-linking agents are well known in the art, and are disclosed in U.S. Pat. No. 4,676,980, along with a number of cross-linking techniques.

Various techniques for making and isolating bispecific antibody fragments directly from recombinant cell culture have also been described. For example, bispecific antibodies have been produced using leucine zippers. See, e.g., Kostelny et al. (1992) *J Immunol* 148(5):1547-1553. The leucine zipper peptides from the Fos and Jun proteins may be linked to the Fab' portions of two different antibodies by gene fusion. The antibody homodimers may be reduced at the hinge region to form monomers and then re-oxidized to form the antibody heterodimers. This method can also be utilized for the production of antibody homodimers. The "diabody" technology described by Hollinger et al. (1993) *Proc Natl Acad Sci USA* 90:6444-6448 has provided an alternative mechanism for making bispecific antibody fragments. The fragments comprise a heavy-chain variable domain (VH) connected to a light-chain variable domain (VL) by a linker which is too short to allow pairing between the two domains on the same chain. Accordingly, the VH and VL domains of one fragment are forced to pair with the complementary VL and VH domains of another fragment, thereby forming two antigen-binding sites. Another strategy for making bispecific antibody fragments by the use of single-chain Fv (scFv) dimers has also been reported. See, e.g., Gruber et al. (1994) *J Immunol* 152:5368. Alternatively, the antibodies can be "linear antibodies" as described in, e.g., Zapata et al. (1995) *Protein Eng* 8(10):1057-1062. Briefly, these antibodies comprise a pair of tandem Fd segments ($V_H$-$C_H1$-$V_H$-$C_H1$) which form a pair of antigen binding regions. Linear antibodies can be bispecific or monospecific.

The disclosure also embraces variant forms of bispecific antibodies such as the tetravalent dual variable domain immunoglobulin (DVD-Ig) molecules described in Wu et al. (2007) *Nat Biotechnol* 25(11):1290-1297. The DVD-Ig molecules are designed such that two different light chain variable domains (VL) from two different parent antibodies are linked in tandem directly or via a short linker by recombinant DNA techniques, followed by the light chain constant domain. Methods for generating DVD-Ig molecules from two parent antibodies are further described in, e.g., PCT Publication Nos. WO 08/024,188 and WO 07/024,715, the disclosures of each of which are incorporated herein by reference in their entirety.

In some embodiments, anti-CD200 antibodies and/or anti-CD20 antibodies can be modified, e.g., with a moiety that improves the stabilization and/or retention of the antibodies themselves in circulation, e.g., in blood, serum, or other tissues. For example, an anti-CD200 antibody described herein can be PEGylated as described in, e.g., Lee et al. (1999) *Bioconjug Chem* 10(6): 973-8; Kinstler et al. (2002) *Advanced Drug Deliveries Reviews* 54:477-485; and Roberts et al. (2002) *Advanced Drug Delivery Reviews* 54:459-476. The stabilization moiety can improve the stability, or retention of, the antibody in a subject's body (e.g., blood or tissue) by at least 1.5 (e.g., at least 2, 5, 10, 15, 20, 25, 30, 40, or 50 or more) fold.

Modification of the Antibodies or Antigen-Binding Fragments Thereof

The anti-CD200 antibodies or anti-CD20 antibodies, or antigen-binding fragments thereof, can be modified following their expression and purification. The modifications can be covalent or non-covalent modifications. Such modifications can be introduced into the antibodies or fragments by, e.g., reacting targeted amino acid residues of the polypeptide with an organic derivatizing agent that is capable of reacting with selected side chains or terminal residues. Suitable sites for modification can be chosen using any of a variety of criteria including, e.g., structural analysis or amino acid sequence analysis of the antibodies or fragments.

In some embodiments, the antibodies or antigen-binding fragments thereof can be conjugated to a heterologous moiety. The heterologous moiety can be, e.g., a heterologous polypeptide, a therapeutic agent (e.g., a toxin or a drug), or a detectable label such as, but not limited to, a radioactive label, an enzymatic label, a fluorescent label, or a luminescent label. Suitable heterologous polypeptides include, e.g., an antigenic tag (e.g., FLAG, polyhistidine, hemagglutinin (HA), glutathione-S-transferase (GST), or maltose-binding protein (MBP)) for use in purifying the antibodies or fragments. Heterologous polypeptides also include polypeptides that are useful as diagnostic or detectable markers, for example, luciferase, green fluorescent protein (GFP), or chloramphenicol acetyl transferase (CAT). Suitable radioactive labels include, e.g., $^{32}P$, $^{33}P$, $^{14}C$, $^{125}I$, $^{131}I$, $^{35}S$, and $^{3}H$. Suitable fluorescent labels include, without limitation, fluorescein, fluorescein isothiocyanate (FITC), green fluorescence protein (GFP), DyLight 488, phycoerythrin (PE), propidium iodide (PI), PerCP, PE-Alexa Fluor® 700, Cy5, allophycocyanin, and Cy7. Luminescent labels include, e.g., any of a variety of luminescent lanthanide (e.g., europium or terbium) chelates. For example, suitable europium chelates include the europium chelate of diethylene triamine pentaacetic acid (DTPA) or tetraazacyclododecane-1,4,7,10-tetraacetic acid (DOTA). Enzymatic labels include, e.g., alkaline phosphatase, CAT, luciferase, and horseradish peroxidase. Heterologous polypeptides can be incorporated into the anti-CD200 antibodies as fusion proteins. Methods for generating nucleic acids encoding an antibody-heterologous polypeptide fusion protein are well known in the art of antibody engineering and described in, e.g., Dakappagari et al. (2006) *J Immunol* 176:426-440.

In some embodiments, the heterologous polypeptide is one that is toxic to a cell. For example, the toxic polypeptide can be selected from the group consisting of *Pseudomonas* exotoxin (PE), bryodin, gelonin, aspergillin, restrictocin, angiogenin, saporin, abrin, a prokaryotic ribonuclease, a eukaryotic ribonuclease, ricin, pokeweed antiviral protein (PAP), a pro-apoptotic polypeptide, a ribosomal inhibitory protein, or a biologically active fragment of any of the foregoing. Pro-apoptotic polypeptides include, e.g., Bax, Bad, Bak, Bim, Bik, Bok, Hrk, FasL, TRAIL, and TNF-α, and pro-apoptotic, biologically-active fragments thereof.

In some embodiments, an anti-CD200 antibody, an anti-CD20 antibody, or antigen-binding fragments thereof can be conjugated to a small molecule or radioactive agent that is toxic to a cell. For example, an anti-CD200 antibody or anti-CD20 antibody can be conjugated to a toxic small molecule selected from the group consisting of cisplatin, carboplatin, procarbazine, mechlorethamine, cyclophosphamide, calicheamicin, camptothecin, adriamycin, ifosfamide, melphalan, chlorambucil, bisulfan, nitrosurea, dactinomycin, daunorubicin, doxorubicin, bleomycin, platinum, plicomycin, monomethyl auristatin, auristatin E, mitomycin, etoposide, verampil, podophyllotoxin, tamoxifen, taxol, transplatinum, 5-fluorouracil, vincristine, vinblastine, methotrexate, or an analog of any of the aforementioned. The antibody or fragment can be conjugated to a radioactive agent that is toxic to a cell. Such radioactive agents include, e.g., $^{90}$Y, $^{186}$Re, $^{188}$Re, $^{64}$Cu, $^{67}$Cu, $^{212}$Pb, $^{212}$Bi, $^{213}$Bi, $^{123}$I, $^{125}$I, $^{131}$I, $^{111}$In, $^{211}$At, $^{32}$P, $^{177}$Lu, $^{47}$Sc, $^{105}$Rh, $^{109}$Pd, $^{153}$Sm, or $^{199}$Au.

Two proteins (e.g., an anti-CD200 antibody or an anti-CD20 antibody and a heterologous moiety) can be cross-linked using any of a number of known chemical cross linkers. Examples of such cross linkers are those which link two amino acid residues via a linkage that includes a "hindered" disulfide bond. In these linkages, a disulfide bond within the cross-linking unit is protected (by hindering groups on either side of the disulfide bond) from reduction by the action, for example, of reduced glutathione or the enzyme disulfide reductase. One suitable reagent, 4-succinimidyloxycarbonyl-α-methyl-α (2-pyridyldithio) toluene (SMPT), forms such a linkage between two proteins utilizing a terminal lysine on one of the proteins and a terminal cysteine on the other. Heterobifunctional reagents that cross-link by a different coupling moiety on each protein can also be used. Other useful cross-linkers include, without limitation, reagents which link two amino groups (e.g., N-5-azido-2-nitrobenzoyloxysuccinimide), two sulfhydryl groups (e.g., 1,4-bis-maleimidobutane), an amino group and a sulfhydryl group (e.g., m-maleimidobenzoyl-N-hydroxysuccinimide ester), an amino group and a carboxyl group (e.g., 4-[p-azidosalicylamido]butylamine), and an amino group and a guanidinium group that is present in the side chain of arginine (e.g., p-azidophenyl glyoxal monohydrate).

In some embodiments, a radioactive label can be directly conjugated to the amino acid backbone of the antibody. Alternatively, the radioactive label can be included as part of a larger molecule (e.g., $^{125}$I in meta-[$^{125}$I]iodophenyl-N-hydroxysuccinimide ([$^{125}$I]mIPNHS) which binds to free amino groups to form meta-iodophenyl (mIP) derivatives of relevant proteins (see, e.g., Rogers et al. (1997) *J Nucl Med* 38:1221-1229) or chelate (e.g., to DOTA or DTPA) which is in turn bound to the protein backbone. Methods of conjugating the radioactive labels or larger molecules/chelates containing them to the anti-CD200 antibodies or anti-CD20 antibodies described herein are known in the art. Such methods involve incubating the proteins with the radioactive label under conditions (e.g., pH, salt concentration, and/or temperature) that facilitate binding of the radioactive label or chelate to the protein (see, e.g., U.S. Pat. No. 6,001,329).

Methods for conjugating a fluorescent label (sometimes referred to as a "fluorophore") to a protein (e.g., an anti-CD200 antibody, an anti-CD20 antibody or antigen-binding fragments of any of the foregoing) are known in the art of protein chemistry. For example, fluorophores can be conjugated to free amino groups (e.g., of lysines) or sulfhydryl groups (e.g., cysteines) of proteins using succinimidyl (NHS) ester or tetrafluorophenyl (TFP) ester moieties attached to the fluorophores. In some embodiments, the fluorophores can be conjugated to a heterobifunctional cross-linker moiety such as sulfo-SMCC. Suitable conjugation methods involve incubating an antibody protein, or fragment thereof, with the fluorophore under conditions that facilitate binding of the fluorophore to the protein. See, e.g., Welch and Redvanly (2003) "Handbook of Radiopharmaceuticals: Radiochemistry and Applications," John Wiley and Sons (ISBN 0471495603).

In some embodiments, the anti-CD200 antibodies or anti-CD20 antibodies can be modified, e.g., with a moiety that improves the stabilization and/or retention of the antibodies in circulation, e.g., in blood, serum, or other tissues. For example, the antibody or fragment can be PEGylated as described in, e.g., Lee et al. (1999) *Bioconjug Chem* 10(6): 973-8; Kinstler et al. (2002) *Advanced Drug Deliveries Reviews* 54:477-485; and Roberts et al. (2002) *Advanced Drug Delivery Reviews* 54:459-476. The stabilization moiety can improve the stability, or retention of, the antibody (or fragment) by at least 1.5 (e.g., at least 2, 5, 10, 15, 20, 25, 30, 40, or 50 or more) fold.

In some embodiments, the anti-CD200 antibodies, or antigen-binding fragments thereof, described herein can be glycosylated. In some embodiments, an antibody or antigen-binding fragment thereof described herein can be subjected to enzymatic or chemical treatment, or produced from a cell, such that the antibody or fragment has reduced or absent glycosylation. Methods for producing antibodies with reduced glycosylation are known in the art and described in, e.g., U.S. Pat. No. 6,933,368; Wright et al. (1991) *EMBO J* 10(10):2717-2723; and Co et al. (1993) *Mol Immunol* 30:1361.

Biological Samples and Sample Collection

Suitable biological samples for use in the methods described herein include any biological fluid, population of cells, or tissue or fraction thereof, which includes one or more white blood cells and/or one or more red blood cells. A biological sample can be, for example, a specimen obtained from a subject (e.g., a mammal such as a human) or can be derived from such a subject. For example, a sample can be a tissue section obtained by biopsy, or cells that are placed in or adapted to tissue culture. A biological sample can also be a biological fluid such as urine, whole blood or a fraction thereof (e.g., plasma), saliva, semen, sputum, cerebral spinal fluid, tears, or mucus. A biological sample can be further fractionated, if desired, to a fraction containing particular cell types. For example, a whole blood sample can be fractionated into serum or into fractions containing particular types of blood cells such as red blood cells or white blood cells (leukocytes). If desired, a biological sample can be a combination of different biological samples from a subject such as a combination of a tissue and fluid sample.

The biological samples can be obtained from a subject, e.g., a subject having, suspected of having, or at risk of developing, a cancer (e.g., a cancer that expresses one or both of CD200 and CD20), e.g., a B-CLL. Any suitable methods for obtaining the biological samples can be employed, although exemplary methods include, e.g., phlebotomy, swab (e.g., buccal swab), lavage, or fine needle aspirate biopsy procedure. Non-limiting examples of tissues susceptible to fine needle aspiration include lymph node, lung, thyroid, breast, and liver. Biological samples can also be obtained from bone marrow. Samples can also be collected, e.g., by microdissection (e.g., laser capture microdissection (LCM) or laser microdissection (LMD)), bladder wash, smear (PAP smear), or ductal lavage.

Methods for obtaining and/or storing samples that preserve the activity or integrity of cells in the biological sample are well known to those skilled in the art. For example, a biological sample can be further contacted with one or more additional agents such as appropriate buffers and/or inhibitors, including protease inhibitors, the agents meant to preserve or minimize changes in the cells (e.g., changes in osmolarity or pH) or denaturation of cell surface proteins (e.g., GPI-linked proteins) or GPI moieties on the surface of the cells. Such inhibitors include, for example, chelators such as ethylenediamine tetraacetic acid (EDTA), ethylene glycol tetraacetic acid (EGTA), protease inhibitors such as phenylmethylsulfonyl fluoride (PMSF), aprotinin, and leupeptin. Appropriate buffers and conditions for storing or otherwise manipulating whole cells are described in, e.g., Pollard and Walker (1997), "Basic Cell Culture Protocols," volume 75 of *Methods in molecular biology*, Humana Press; Masters (2000) "Animal cell culture: a practical approach," volume 232 of *Practical approach series*, Oxford University Press; and Jones (1996) "Human cell culture protocols," volume 2 of *Methods in molecular medicine*, Humana Press.

A sample also can be processed to eliminate or minimize the presence of interfering substances. For example, a biological sample can be fractionated or purified to remove one or more materials (e.g., cells) that are not of interest. Methods of fractionating or purifying a biological sample include, but are not limited to, flow cytometry, fluorescence activated cell sorting, and sedimentation.

Applications

The compositions described herein can be used in a number of therapeutic and diagnostic applications, e.g., the anti-CD200 antibodies described herein can be used in methods for treating or diagnosing cancer or autoimmune disorders. For example, after it is determined that a patient is afflicted with a cancer that is resistant to treatment with an anti-CD20 therapeutic agent (e.g., an anti-CD20 antibody such as rituximab), a medical practitioner may elect to administer to the human the anti-CD200 antibody in an amount and with a frequency sufficient to treat the patient's cancer. In some embodiments, a medical practitioner may administer to a patient afflicted with a cancer (e.g., a liquid tumor) an anti-CD200 antibody and an anti-CD20 therapeutic agent to treat the cancer, after it has been determined that the patient's cancer comprises cancer cells expressing CD5. Methods for therapeutically administering an anti-CD200 antibody to a human are well known in the art and described in, e.g., U.S. Pat. No. 7,408,041.

Methods for Treating Autoimmune Disorders

The disclosure also provides therapeutic and diagnostic applications for treating autoimmune disorders, e.g., by reducing the concentration of autoimmune disease-associated autoantibodies in a subject afflicted with the disorder. For example, a medical practitioner may elect to administer to a human with an autoimmune disorder (e.g., autoimmune hemolytic disease) an anti-CD200 antibody in an amount and with a frequency sufficient to reduce the expression (or production) of the disorder-associated autoantibody, or to reduce the concentration of the autoantibody in the blood of the patient, to thereby treat the patient's autoimmune disorder. Methods for therapeutically administering an anti-CD200 antibody to a human are well known in the art and described in, e.g., U.S. Pat. No. 7,408,041.

An "autoimmune disorder," as used herein, refers to a disease state in which, via the action of white blood cells (e.g., B cells, T cells, macrophages, monocytes, or dendritic cells), a pathological immune response (e.g., pathological in duration and/or magnitude) has been generated in a host organism against a substance or a tissue that is normally present within the host organism. Types of autoimmune diseases include, but are not limited to, chronic obstructive pulmonary disease, diabetes mellitus type 1, Goodpasture's syndrome, Grave's disease, Guillain-Barré syndrome, IgA nephropathy, scleroderma, Sjögren's syndrome, Wegener's granulomatosis, pemphigus vulgaris, rheumatoid arthritis, Crohn's disease, Hashimoto's disease, idiopathic thrombocytopenic purpura, myasthenia gravis (MG), pulmonary biliary cirrhosis, and Miller Fisher syndrome. Autoimmune disorders also include certain autoimmune hemolytic disorders such as antiphospholipid syndrome (APS), catastrophic anti-phospholipid syndrome (CAPS), typical or atypical hemolytic uremic syndrome (HUS), and autoimmune hemolytic anemia (AIHA). AIHA refers to a family of related diseases that are characterized by production of autoantibodies to host red blood cells. AIHA includes, e.g., warm AIHA (WAIHA), cold AIHA (CAD), paroxysmal cold hemoglobinuria (PCH), and drug-induced hemolytic anemias (DIHA).

A human "at risk of developing an autoimmune disorder" refers to a human with a family history of autoimmune disorders (e.g., a genetic predisposition to one or more inflammatory disorders) or one exposed to one or more autoimmune disorder/autoantibody-inducing conditions. For example, a human exposed to a shiga toxin is at risk for developing typical HUS. Humans with certain cancers (e.g., liquid tumors such as multiple myeloma or chronic lymphocytic leukemia) can pre-dispose patients to developing certain autoimmune hemolytic diseases. For example, PCH can follow a variety of infections (e.g., syphilis) or neoplasms such as non-Hodgkin's lymphoma. In another example, CAD can be associated with HIV infection, *Mycoplasma pneumonia* infection, non-Hodgkin's lymphoma, or Waldenstrom's macroglobulinemia. In yet another example, autoimmune hemolytic anemia is a well-known complication of human chronic lymphocytic leukemia, approximately 11% of CLL patients with advanced disease will develop AIHA. As many as 30% of CLL may be at risk for developing AIHA. See, e.g., Diehl et al. (1998) *Semin Oncol* 25(1):80-97 and Gupta et al. (2002) *Leukemia* 16(10):2092-2095. From the above it will be clear that humans "at risk of developing an autoimmune disorder" are not all the humans within a species of interest.

A human "suspected of having an autoimmune disorder" is one who presents with one or more symptoms of an autoimmune disorder. Symptoms of autoimmune disorders can vary in severity and type with the particular autoimmune disorder and include, but are not limited to, redness, swelling (e.g., swollen joints), joints that are warm to the touch, joint pain, stiffness, loss of joint function, fever, chills, fatigue, loss of energy, pain, fever, pallor, icterus, urticarial dermal eruption, hemoglobinuria, hemoglobinemia, and anemia (e.g., severe anemia), headaches, loss of appetite, muscle stiffness, insomnia, itchiness, stuffy nose, sneezing, coughing, one or more neurologic symptoms such as dizziness, seizures, or pain. From the above it will be clear that not all humans are "suspected of having an autoimmune disorder."

In some embodiments, the medical practitioner can administer an anti-CD200 antibody to a human in an amount effective to reduce the expression or production of an autoimmune disorder-associated autoantibody in the human. For example, PCH most commonly results from the production by a subject of an autoantibody (known as the "Donath-Landsteiner antibody") that binds to the P antigen of red blood cells in cold temperatures. Once bound to the red blood cells, the antibody facilitates complement-mediated hemolysis of the cells at warmer temperatures. As many as 40% of immune hemolytic anemias in children are associated with the Donath-Landsteiner antibody. See, e.g., Sokol et al. (1982) *Acta Haematol* 68(4):268-77. Thus, e.g., an anti-CD200 antibody can be administered to a PCH patient in an amount sufficient to reduce the production or expression of the Donath-Landsteiner antibody in the human to thereby treat the human's PCH.

Similarly, CAD (or cold hemagglutinin disease or CHD/CHAD) is an autoimmune disorder characterized by autoantibodies that bind to the I antigen on red blood cells at colder temperatures. Once bound, the antibodies facilitate hemagglutination, and complement-mediated hemolysis, of the cells. Thus, a medical practitioner can administer an anti-CD200 antibody in an amount sufficient to reduce the production or expression of the anti-I antigen antibodies in the human to thereby treat the human's CAD.

In another example, a large number of patients with MG express antibodies that bind to and inhibit the activity of the nicotinic acetylcholine receptor (AChR). The antibodies cause loss of acetylcholine receptors and diminished receptor function at the muscle end-plate of the mature neuromuscular junction. Some patients who are lacking in detectable anti-AChR antibodies instead express auto-antibodies directed to a muscle-specific receptor tyrosine kinase (MuSK). See, e.g., Hoch et al. (2001) *Nature Med.* 7(3):365-368). Thus, a medical practitioner can administer an anti-CD200 antibody in an amount sufficient to reduce the production or expression of the anti-AChR or anti-MuSK antibodies in the human to thereby treat the human's MG.

Methods for detecting the presence or amount of an autoimmune disorder-associated autoantibody in a human are well known in the art and are described in, e.g., Burbelo et al. (2009) *J Transl Med* 7:83; Hanke et al. (2009) *Arthritis Res Ther* 11(1):R22; Hoch et al. (2001), supra; Vernino et al. (2008) *J Neuroimmunol* 197(1):63-69; Sokol et al. (1982), supra; and Littleton et al. (2009) *Mol Cell Proteomics* 8(7): 1688-1696.

In some embodiments, the anti-CD200 antibody is administered to a subject in an amount and with a frequency to maintain a reduced concentration (or a reduced expression or production) of the autoimmune disorder-associated autoantibody. Methods for detecting expression or a change in concentration of autoantibodies are well known in the art (e.g., Western blot, immunohistochemistry, and flow cytometry techniques) and described herein. Through an iterative process, a medical practitioner can determine the appropriate dose amount, and frequency of administration of each dose, required to maintain a reduced concentration of the autoimmune disorder-associated autoantibodies in the patient. For example, a medical practitioner can administer to a patient with an autoimmune disorder such as AIHA one or more (e.g., one, two, three, four, five, six, seven, eight, nine, or 10 or more or, e.g., at least two, at least three, four, five, six, seven, or eight or more) times an anti-CD200 antibody in an amount that reduces (or is at least expected to reduce) the concentration of autoantibodies in the human. The at least two doses should be spaced apart in time by at least one (e.g., at least two, three, four, five, six, seven, eight, nine, 10, 11, 12, 13, or even 14) day(s). Biological samples (e.g., blood samples) containing the autoantibodies are obtained from the patient at various times, e.g., prior to the first anti-CD200 antibody administration, between the first dose and at least one additional dose, and at least one biological sample collection following the second dose. In some embodiments, biological samples may be collected at least two times between doses and/or at least one time after the final dose administered to the patient. The autoantibodies in each biological sample obtained are then interrogated for relative titer of the autoimmune-disease associated autoantibody to determine whether the amount and/or the frequency of administration of the anti-CD200 antibody are sufficient to maintain a reduced concentration of the autoantibody in the patient. The medical practitioner (and/or a computer) can determine an anti-CD200 antibody dosing schedule for the patient that is sufficient to maintain a reduced concentration of autoimmune disorder-associated autoantibodies in the patient over the course of the treatment.

In some embodiments, administration of the anti-CD200 antibody to the human reduces the autoantibody concentration by at least 5 (e.g., at least 6, 7, 8, 9, 10, 11, 12, 13, 14, 15, 16, 17, 18, 19, 20, 25, 30, 35, 40, 45, 50, 55, 60, 65, 70, 75, 80, or 85 or more) %.

In some embodiments, the anti-CD200 antibody can be chronically administered to the human. As used herein, "chronically administered," "chronic treatment," "treating chronically," or similar grammatical variations thereof refer to a treatment regimen that is employed to maintain a certain threshold concentration of a therapeutic agent in the blood of a patient in order to maintain a particular state in the patient over a prolonged period of time. For example, an anti-CD200 antibody can be chronically administered a patient with MG to maintain a reduced concentration of anti-AChR antibodies in the blood of the patient for a prolonged period of time. Accordingly, a patient chronically treated with a anti-CD200 antibody can be treated for a period of time that is greater than or equal to 2 weeks (e.g., 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, or 52 weeks; 1, 2, 3, 4, 5, 6, 7, 8, 9, 10, 11, or 12 months; or 1, 1.5, 2, 2.5, 3, 3.5, 4, 4.5, 5, 5.5, 6, 6.5, 7, 7.5, 8, 8.5, 9, 9.5, 10, 10.5, or 12 years or for the remainder of the patient's life).

The inventors have identified and provided herein several biomarkers consistent with the production in a human of an immunomodulatory effect by an anti-CD200 antibody administered to the human. That is, upon administration of the antibody to mice with an autoimmune disease (autoimmune hemolytic disease), the concentration of a number of splenocyte and bone marrow cell subsets changed in the mice. An "immunomodulatory effect" and grammatically similar terms, as used herein, refer to a measurable immunological effect in an animal (e.g., a human) attributable to the biological activity of an anti-CD200 antibody administered to an animal (e.g., a human). For example, the inventors have observed that following administration of an anti-CD200 antibody to a mouse, the concentration of the following CD200$^+$ leukocyte populations is reduced: CD3$^+$/CD200$^+$ cells, CD45R$^+$/CD200$^+$ cells, CD5$^+$/CD200$^+$ cells, CD19$^+$/CD200$^+$ cells, CD138$^+$/CD200$^+$ cells, CD45R$^+$/CD138$^+$/CD200$^+$, and CD200R$^+$/CD200$^+$ cells. In some embodiments, the CD200$^+$ leukocytes are localized in the spleen. The reduction of the aforementioned CD200$^+$ cell subsets can also be observed in peripheral blood. Also observed was that upon administration of an anti-CD200 antibody to a mouse, the concentration of the following CD200$^+$ bone marrow cell subsets is reduced: CD200$^+$ bone marrow cells, Igk$^+$/CD200$^+$ bone marrow cells, CD45R$^+$/CD138$^+$/CD200$^+$ bone marrow cells, CD138$^+$/CD200$^+$ bone marrow cells, c-kit$^+$/CD200$^+$ bone marrow cells, and c-kit$^+$/CD200$^+$/Lin$^-$ bone marrow cells. While not being bound by any particular theory or mechanism of action, the inventors believe that monitoring a patient treated with an anti-CD200 antibody for the occurrence of one or more of these biomarkers is useful for, at bottom, determining whether the anti-CD200 antibody is capable of producing a biological effect in the human to whom the antibody is administered. Moreover, one or more of the biomarkers are also useful for identifying a dose—a threshold dose—of an anti-CD200 antibody, such as samalizumab (ALXN6000), that by virtue of its immunomodulatory effect in the human is sufficient to achieve a clinically-meaningful effect in the disease (i.e., sufficient to treat a disease such as an autoimmune disorder or a cancer). To wit, mice with autoimmune hemolytic disease treated with an anti-CD200 antibody exhibited a reduced concentration of the disease-associated autoantibody in the mice.

Thus, in accordance with the present disclosure, a medical practitioner can administer to a human in need thereof an anti-CD200 antibody in an amount and with a frequency sufficient to treat the autoimmune disorder by maintaining one or more of the following physiological conditions (immunological effects) in the human: (i) a decreased concentration of at least one CD200$^+$ leukocyte subset (e.g., at least one CD200$^+$ splenocyte subset); (ii) an increased concentration of splenic or peripheral F4/80$^+$ cells; and (iii) a decreased concentration of at least one bone marrow stem cell subset. The CD200$^+$ leukocyte subsets can be, e.g., CD3$^+$/CD200$^+$ cells, CD45R$^+$/CD200$^+$ cells, CD5$^+$/CD200$^+$ cells, CD19$^+$/CD200$^+$ cells, CD138$^+$/CD200$^+$ cells, CD45R$^+$/CD138$^+$/CD200$^+$, and CD200R$^+$/CD200$^+$ cells. The CD200$^+$ bone marrow cell subsets can be, e.g., CD200$^+$ bone marrow cells, Igk$^+$/CD200$^+$ bone marrow cells, CD45R$^+$/CD138$^+$/CD200$^+$ bone marrow cells, CD138$^+$/CD200$^+$ bone marrow cells, c-kit$^+$/CD200$^+$ bone marrow cells, and c-kit$^+$/CD200$^+$/Lin$^-$ bone marrow cells. The splenic or peripheral F4/80$^+$ cells can be macrophages. In some cases, at least two of the physiological conditions are maintained. In some embodiments, all of the conditions are maintained in the human throughout the treatment period.

Methods for measuring the concentration of CD200$^+$ cells (e.g., any of the CD200$^+$ leukocyte or bone marrow cell subsets) are well known in the art and include, among other methods, flow cytometry. See, e.g., Chen et al. (2009) *Mol Immunol* 46(10):1951-1963. A suitable method for detecting and/or measuring the concentration of CD200$^+$ bone marrow cell, splenocyte, or peripheral blood leukocyte subsets is also set forth in the working examples. In some embodiments, a practitioner can interrogate a biological sample obtained from a post-treatment patient (a patient to which an anti-CD200 antibody has been administered) for the concentration of cells of a particular subset of CD200$^+$ cells. For example, a practitioner can determine the concentration of CD45R$^+$/CD200$^+$ leukocytes and/or the concentration of c-kit$^+$/CD200$^+$/Lin$^-$ bone marrow cells present in a biological sample from a post-treatment patient.

In some embodiments, following administration of an anti-CD200 antibody to a human the concentration of a CD200$^+$ leukocyte (e.g., CD200$^+$ leukocyte population in spleen) or bone marrow cell subset that is at least 5% less than the concentration of the corresponding subset in the human prior to the treatment. In some embodiments, a post-treatment CD200$^+$ splenocyte or bone marrow cell subset concentration that is at least 10 (e.g., 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 50, 55, 60, 65, 70, 75, 80, or more than 80) % less than the concentration of the corresponding subset prior to treatment with the antibody.

An anti-CD200 antibody described herein can be co-administered with one or more additional therapeutic agents useful for treating or preventing an inflammatory condition. The one or more agents include, e.g., a non-steroidal anti-inflammatory drug (NSAID), a disease-modifying anti-rheumatic drug (DMARD), a biological response modifier, or a corticosteroid. Biological response modifiers include, e.g., an anti-TNF agent (e.g., a soluble TNF receptor or an antibody specific for TNF such as adulimumab, infliximab, or etanercept). In some embodiments, the one or more additional therapeutic agents can be, e.g., steroids, anti-malarials, aspirin, non-steroidal anti-inflammatory drugs, immunosuppressants, cytotoxic drugs, corticosteroids (e.g., prednisone, dexamethasone, and prednisolone), methotrexate, methylprednisolone, macrolide immunosuppressants (e.g., sirolimus and tacrolimus), mitotic inhibitors (e.g., azathioprine, cyclophosphamide, and methotrexate), fungal metabolites that inhibit the activity of T lymphocytes (e.g., cyclosporine), mycophenolate mofetil, glatiramer acetate, and cytotoxic and DNA-damaging agents (e.g., chlorambucil or any other DNA-damaging agent described herein or known in the art).

Methods for Treating Cancers

The disclosure also provides therapeutic and diagnostic applications for treating cancers. For example, after it is determined that a human has a tumor that comprises tumor cells expressing CD200, a medical practitioner may elect to administer to the human the anti-CD200 antibody in an amount and with a frequency sufficient to treat the patient's cancer. Methods for therapeutically administering an anti-CD200 antibody to a human are well known in the art and described in, e.g., U.S. Pat. No. 7,408,041.

Cancer is a class of diseases or disorders characterized by uncontrolled division of cells and the ability of these to spread, either by direct growth into adjacent tissue through invasion, or by implantation into distant sites by metastasis (where cancer cells are transported through the bloodstream or lymphatic system). Cancer can affect people at all ages, but risk tends to increase with age. Types of cancers can include, e.g., lung cancer, breast cancer, colon cancer, pancreatic cancer, renal cancer, stomach cancer, liver cancer, bone cancer, hematological cancer, neural tissue cancer (e.g., neuroblastoma), melanoma, thyroid cancer, ovarian cancer, a liquid tumor, testicular cancer, prostate cancer, cervical cancer, vaginal cancer, or bladder cancer. Liquid tumors include, e.g., leukemias (e.g., chronic lymphocytic leukemia such as B cell or T cell type chronic lymphocytic leukemia) and multiple myeloma. Bone cancers include, without limitation, osteosarcoma and osteocarcinomas.

As used herein, a human "at risk of developing a cancer" is a human that has a predisposition to develop a cancer, i.e., a genetic predisposition to develop cancer such as a mutation in a tumor suppressor gene (e.g., mutation in BRCA1, p53, RB, or APC or other genetic rearrangements) or has been exposed to conditions that can result in cancer. Thus, a human can also be one "at risk of developing a cancer" when the human has been exposed to mutagenic or carcinogenic levels of certain compounds (e.g., carcinogenic compounds in cigarette smoke such as acrolein, arsenic, benzene, benz {a} anthracene, benzo{a}pyrene, polonium-210 (radon), urethane, or vinyl chloride). Moreover, the human can be "at risk of developing a cancer" when the human has been exposed to, e.g., large doses of ultraviolet light or X-irradiation, or infected by a tumor-causing/associated virus such as a papillomavirus, Epstein-Barr virus, hepatitis B virus, or human T-cell leukemia-lymphoma virus. From the above it will be clear that not all humans are "at risk of developing a cancer."

A human "suspected of having a cancer" is one having one or more symptoms of a cancer. Symptoms of cancer are well-known to those of skill in the art and include, without limitation, breast lumps, pain, weight loss, weakness, excessive fatigue, difficulty eating, loss of appetite, chronic cough, worsening breathlessness, coughing up blood, blood in the urine, blood in stool, nausea, vomiting, liver metastases, lung metastases, bone metastases, abdominal fullness, bloating, fluid in peritoneal cavity, vaginal bleeding, constipation, abdominal distension, perforation of colon, acute peritonitis (infection, fever, pain), pain, vomiting blood, heavy sweating, fever, high blood pressure, anemia, diarrhea, jaundice, dizziness, chills, muscle spasms, and difficulty swallowing. Symptoms of a primary cancer (e.g., a large primary cancer) can include, e.g., any one of colon metastases, lung metastases, bladder metastases, liver metastases, bone metastases, kidney metastases, and pancreas metastases.

The inventors have discovered that administration of an anti-CD200 antibody to an animal resulted in a marked reduction in the concentration of $CD5^+$ cells in the spleen of the animal. While the disclosure is not bound by any particular theory or mechanism of action, it is likely that $CD5^+$ CLL cells may be refractory to rituximab therapy at least in part because of a reduced expression by the cells of CD20. The inventors have shown that a therapeutic composition containing an anti-CD200 antibody is useful for reducing $CD5^+$ cell populations in an animal and thus believe that the composition is particularly useful for treating a subset of CLL patients that are refractory to treatment with anti-CD20 therapy (e.g., rituximab-resistant).

Accordingly, the disclosure features a variety of methods for treating cancers, particularly for selecting or identifying which cancers may most benefit from treatment with an anti-CD200 antibody. For example, the disclosure features a method for treating a human afflicted with cancer that is resistant, suspected to be resistant, or likely to be resistant, to treatment with an anti-CD20 therapeutic agent such as rituximab. "Resistance" to a therapy, "refractory" to therapy, and like grammatical phrases, as used herein, refer to a patient's clinical state of being, in which there is a reduction in the effectiveness of a given treatment (e.g., treatment with an anti-CD20 therapeutic agent) in treating or curing a given disorder (e.g., a cancer) or a reduction in the effectiveness of the treatment in ameliorating one or more symptoms associated with the disorder. For example, the therapeutic benefits of an anti-CD20 therapy to a patient afflicted with a liquid tumor such as B cell chronic lymphocytic leukemia may diminish over time such that the cancer recurs, remains, or progresses even in the presence of the therapy. Resistance by cancers to therapeutic agents such as anti-CD20 therapeutic agents is well-documented in the art of medicine and is described in, e.g., Reddy et al. (2006) *J Clin Oncol* 24(18S): 17509; Bello and Sotomayor (2007) *Hematology* 1:233; Hernandez-Ilizaliturri et al. (2009) *J Clin Oncol* 27(15s):8543; and Friedberg et al. (2005) *Hematology* 1:329.

In some embodiments, a patient can have a cancer that is suspected of being resistant or is likely to become resistant to an anti-CD20 therapy. One biomarker useful in assessing whether a cancer is likely to become resistant to an anti-CD20 therapeutic agent such as rituximab is the presence or concentration of $CD5^+$ cancer cells in the population. As described above, because the $CD5^+$ cells express reduced levels of CD20, the cells are less affected by the anti-CD20 therapy and thus can be selected for due to a growth advantage over cancer cells that express higher levels of CD20. Methods for detecting the expression of CD5 are well known in the art of molecular biology and include, without limitation, Western blotting, dot blotting, and flow cytometry, which are useful for quantifying expression of CD5 protein, or reverse transcriptase polymerase chain reaction (RT-PCR) and Northern blotting analysis for quantifying expression of CD5 mRNA. See, e.g., Ennishi et al. (2008), supra; Holodick et al. (2009), supra; Garaud et al. (2009) *J Immunol* 182(9):5623-5632; and McNab et al. (2009) *Ann Clin Lab Sci* 39(2):108-113. See generally Sambrook et al. (1989) *"Molecular Cloning: A Laboratory Manual, $2^{nd}$ Edition,"* Cold Spring Harbor Laboratory Press, Cold Spring Harbor, N.Y. and Ausubel et al. (1992) "Current Protocols in Molecular Biology," Greene Publishing Associates. A suitable method for detecting and/or quantifying the expression of CD5 by cells, or for determining the percentages of CD5 expressing cells in a population, is flow cytometry and is exemplified in the working examples.

In some embodiments, a cancer that is likely to be resistant to an anti-CD20 therapeutic agent comprises at least a plurality or a portion (e.g., two or more; at least 0.5%, 0.6%, 0.7%, 0.8%, 0.9%, 1.0%, 1.5%, 2%, 3%, 4%, 5%, 6%, 7%, 8%, 9%, 10%, 12%, 15%, 17%, 20%, 25%, 30%, 35%, 40%, or 45% or more) of cancer cells (e.g., B cell chronic lymphocytic leukemia cells) expressing CD5. In some embodiments, greater than 45 (e.g., greater than 50, 55, 60, 65, 70, 75, or 80 or more) % of a patient's cancer cells can express CD5. In some embodiments, the cancer comprises cells (e.g., a plurality or even a majority of cells) that express or overexpress CD5 (e.g., CD5 protein and/or CD5 mRNA). In some embodiments, at least (or greater than) 10 (e.g., 15, 20, 25, 30, 35, 40, 45, 50, 55, 60, 65, 70, 75, 80, 85, 90, or 95) % of the cancer cells of the human's cancer overexpress CD5. In some embodiments, all assayed cancer cells overexpress CD5 relative to normal cells. In some embodiments, a cancer cell (e.g., a plurality of cancer cells, at least 10% of cancer cells, or all assayed cancer cells) can express CD5 protein at levels at least about 1.4 (e.g., at least about 1.5, 1.6, 1.7, 1.8, 1.9, 2.0, 2.2, 2.5, 3.0, 3.5, 4.0, 4.5, or 5 or more)-fold higher than the expression levels found on normal cells of the same histological type or higher than the average expression of normal cells from one or more patients who do not have cancer.

In some embodiments, the methods described herein can include determining whether the human has a cancer. In some embodiments, the methods described herein can include the step of determining whether one or more cancer cells of a human's cancer express CD200. In some embodiments, the methods can include determining whether one or more cancer cells of the human's cancer overexpress CD200, relative to a control sample. In some embodiments, the control sample is obtained from the same human and comprises normal cells of the same tissue type as the human's cancer. For example, a skilled artisan could measure the level of CD200 protein present on colon cancer cells from a patient as compared to normal colon cells from the patient. In some embodiments, the control sample can be the expression level (or average expression level) of cells obtained from one or more humans who do not have cancer. In some embodiments, the cancer comprises cells (e.g., a plurality or even a majority of cells) that express or overexpress CD200 (e.g., CD200 protein and/or CD200 mRNA). In some embodiments, at least (or greater than) 10 (e.g., 15, 20, 25, 30, 35, 40, 45, 50, 55, 60, 65, 70, 75, 80, 85, 90, or 95) % of the cancer cells of the human's cancer overexpress CD200. In some embodiments, all assayed cancer cells overexpress CD200 relative to normal cells. In some embodiments, a cancer cell (e.g., a plurality of cancer cells, at least 10% of cancer cells, or all assayed cancer cells) can express CD200 protein at levels at least about 1.4 (e.g., at least about 1.5, 1.6, 1.7, 1.8, 1.9, 2.0, 2.2, 2.5, 3.0, 3.5, 4.0, 4.5, or 5 or more)-fold higher than the expression levels found on normal cells of the same histological type or higher than the average expression of normal cells from one or more patients who do not have cancer.

In some embodiments, an anti-CD200 antibody is only administered to a human if the human's cancer expresses or overexpresses CD200. Methods for detecting expression of CD200 are well known in the art and include, e.g., Western blot, immunohistochemistry, and flow cytometry techniques. Suitable methods for detecting CD200 expression are described in detail in, e.g., Kretz-Rommel et al. (2007) *J Immunol* 178:5595-5605 and Kretz-Rommel et al. (2008) *J Immunol* 180:699-705. In some embodiments, an anti-CD200 antibody is only administered to a human if the human's cancer expresses or overexpresses CD200 and CD5.

In some embodiments, an anti-CD200 antibody blocks immune suppression in cancer by targeting cancer cells that express CD200. Eradication, or inhibition, of these cancer cells can stimulate the immune system and allow further eradication of cancer cells.

In some embodiments, the combination of direct cancer cell killing and driving the immune response towards a Th1 profile provides enhanced efficacy in cancer treatment. Thus, in one embodiment, a cancer treatment is provided wherein an antibody or antibody fragment, which binds to CD200 and both a) blocks the interaction between CD200 and its receptor and b) directly kills the cancer cells expressing CD200, is administered to a cancer patient. The mechanisms by which the cancer cells are killed can include, but are not limited to, ADCC or CDC; fusion with a toxin; fusion with a toxic radioactive agent; fusion with a toxic polypeptide such as granzyme B or perforin; fusion with a cytotoxic virus (e.g., cytotoxic reovirus such as Reolysin®); or fusion with a cytokine such as TNF-α or IFN-α. In an alternative embodiment, a cancer treatment involves administering an antibody that both a) blocks the interaction between CD200 and its receptor and b) enhances cytotoxic T cell or NK cell activity against the tumor. Such enhancement of the cytotoxic T cell or NK cell activity may, for example, be combined by fusing the antibody with cytokines such as, e.g., IL-2, IL-12, IL-18, IL-13, and IL-5. In addition, such enhancement may be achieved by administration of an anti-CD200 antibody in combination with inhibitors such as IMiDs, thalidomide, or thalidomide analogs.

In yet another embodiment, the cancer treatment involves administering an antibody that both a) blocks the interaction between CD200 and its receptor and b) attracts T cells to the tumor cells. T cell attraction can be achieved by fusing the Ab with chemokines such as MIG, IP-10, I-TAC, CCL21, CCL5 or LIGHT. Also, treatment with chemotherapeutics can result in the desired upregulation of LIGHT. The combined action of blocking immune suppression and killing directly through antibody targeting of the tumor cells is a unique approach that provides increased efficacy.

The disclosure also provides a method of treating a cancer using a combination therapy of an anti-CD200 antibody and an anti-CD20 therapeutic agent. While not being bound by any particular theory or mechanism of action, the inventors believe that administration of an anti-CD200 antibody will enhance the efficacy of an anti-CD20 therapeutic agent by reducing the proportion of cancer cells that are likely to be refractory, namely the CD5$^+$ cancer cells. The anti-CD20 therapeutic agent can be any of those described herein or known in the art such as, e.g., rituximab (Biogen Idec), $^{90}$Y-ibritumomab tiuxetan (Biogen Idec), $^{131}$I-tositumomab (GlaxoSmithKline), ofatumumab (Genmab), TRU-015 (Trubion), veltuzumab (IMMU-106; Immunomedics), ocrelizumab (Roche), and AME-133v (Applied Molecular Evolution).

In some embodiments, the anti-CD200 antibody and the anti-CD20 therapeutic agent are separate agents. Accordingly, the anti-CD200 antibody and the anti-CD20 therapeutic agent can be administered at the same time. In other embodiments, the anti-CD200 antibody is administered first in time and the anti-CD20 therapeutic agent is administered second in time. In some embodiments, the anti-CD20 therapy is administered first in time and the anti-CD200 antibody is administered second in time.

The anti-CD200 antibody can replace or augment a previously or currently administered therapy such as an anti-CD20 therapeutic agent. For example, upon treating with an anti-CD200 antibody or antigen-binding fragment thereof, administration of the anti-CD20 therapeutic agent can cease or diminish, e.g., be administered at lower levels. In some embodiments, administration of the anti-CD20 therapeutic agent can be maintained. In some embodiments, administration of the anti-CD20 therapeutic agent will be maintained until the level of the anti-CD200 antibody reaches a level sufficient to provide a therapeutic effect. The two therapies can be administered in combination as a single agent, e.g., a bispecific antibody that binds to both CD200 and CD20 (see above).

An anti-CD200 antibody described herein can also be co-administered to a human with cancer along with one or more additional therapeutic anti-cancer agents. Likewise an anti-CD200 antibody described herein can be co-administered to a human with cancer along with an anti-CD20 therapeutic agent and one or more additional therapeutic anti-cancer agents. Anti-cancer agents include, e.g., chemotherapeutic agents, ionizing radiation, immunotherapy agents, or hyperthermotherapy agents. Chemotherapeutic agents include, but are not limited to, aminoglutethimide, amsacrine, anastrozole, asparaginase, bcg, bicalutamide, bleomycin, buserelin, busulfan, camptothecin, capecitabine, carboplatin, carmustine, chlorambucil, cisplatin, cladribine, clodronate, colchicine, cyclophosphamide, cyproterone, cytarabine, dacarbazine, dactinomycin, daunorubicin, dienestrol, diethylstilbestrol, docetaxel, doxorubicin, epirubicin, estradiol, estramustine, etoposide, exemestane, filgrastim, fludarabine, fludrocortisone, fluorouracil, fluoxymesterone, flutamide, gemcitabine, genistein, goserelin, hydroxyurea, idarubicin, ifosfamide, imatinib, interferon, irinotecan, letrozole, leucovorin, leuprolide, levamisole, lomustine, mechlorethamine, medroxyprogesterone, megestrol, melphalan, mercaptopurine, mesna, methotrexate, mitomycin, mitotane, mitoxantrone, nilutamide, nocodazole, octreotide, oxaliplatin, paclitaxel, pamidronate, pentostatin, plicamycin, porfimer, procarbazine, raltitrexed, rituximab, streptozocin, suramin, tamoxifen, taxol, temozolomide, teniposide, testosterone, thioguanine, thiotepa, titanocene dichloride, topotecan, trastuzumab, tretinoin, vinblastine, vincristine, vindesine, and vinorelbine. In some embodiments, a pharmaceutical composition comprising an anti-CD200 antibody or CD200-binding fragment thereof can be co-formulated with one or more of any of the foregoing agents or any other anti-cancer agent described herein.

These chemotherapeutic anti-tumor compounds may be categorized by their mechanism of action into groups, including, for example, the following: anti-metabolites/anti-cancer agents, such as pyrimidine analogs (5-fluorouracil, floxuridine, capecitabine, gemcitabine and cytarabine) and purine analogs, folate antagonists and related inhibitors (mercaptopurine, thioguanine, pentostatin and 2-chlorodeoxyadenosine (cladribine)); antiproliferative/antimitotic agents including natural products such as vinca alkaloids (vinblastine, vincristine, and vinorelbine), microtubule disruptors such as taxane (paclitaxel, docetaxel), vincristine, vinblastine, nocodazole, epothilones and navelbine, epidipodophyllotoxins (etoposide, teniposide), DNA damaging agents (actinomycin, amsacrine, anthracyclines, bleomycin, busulfan, camptothecin, carboplatin, chlorambucil, cisplatin, cyclophosphamide, cytoxan, dactinomycin, daunorubicin, doxorubicin, epirubicin, hexamethylmelamineoxaliplatin, iphosphamide, melphalan, mechlorethamine, mitomycin, mitoxantrone, nitrosourea, plicamycin, procarbazine, taxol, taxotere, teniposide, triethylenethiophosphoramide and etoposide (VP16)); antibiotics such as dactinomycin (actinomycin D), daunorubicin, doxorubicin (adriamycin), idarubicin, anthracyclines, mitoxantrone, bleomycins, plicamycin (mithramycin) and mitomycin; enzymes (L-asparaginase which systemically metabolizes L-asparagine and deprives cells which do not have the capacity to synthesize their own asparagine); antiplatelet agents; antiproliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nitrosoureas (carmustine (BCNU) and analogs, streptozocin), trazenes—dacarbazinine (DTIC); antiproliferative/antimitotic antimetabolites such as folic acid analogs (methotrexate); platinum coordination complexes (cisplatin, carboplatin), procarbazine, hydroxyurea, mitotane, aminoglutethimide; hormones, hormone analogs (estrogen, tamoxifen, goserelin, bicalutamide, nilutamide) and aromatase inhibitors (letrozole, anastrozole); anticoagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory agents; antisecretory agents (breveldin); immunosuppressives (cyclosporine, tacrolimus (FK-506), sirolimus (rapamycin), azathioprine, mycophenolate mofetil); immunomodulatory agents (thalidomide and analogs thereof such as lenalidomide (Revlimid, CC-5013) and CC-4047 (Actimid)), cyclophosphamide; anti-angiogenic compounds (TNP-470, genistein) and growth factor inhibitors (vascular endothelial growth factor (VEGF) inhibitors, fibroblast growth factor (FGF) inhibitors); angiotensin receptor blocker; nitric oxide donors; anti-sense oligonucleotides; antibodies (trastuzumab); cell cycle inhibitors and differentiation inducers (tretinoin); mTOR inhibitors, topoisomerase inhibitors (doxorubicin (adriamycin), amsacrine, camptothecin, daunorubicin, dactinomycin, eniposide, epirubicin, etoposide, idarubicin and mitoxantrone, topotecan, irinotecan), corticosteroids (cortisone, dexamethasone, hydrocortisone, methylprednisolone, prednisone, and prednisolone); growth factor signal transduction kinase inhibitors; mitochondrial dysfunction inducers and caspase activators; and chromatin disruptors.

In some embodiments, the methods described herein can include, after administering the anti-CD200 antibody, monitoring the human for an improvement in the disorder and/or one or more symptoms thereof. Monitoring a human for an improvement in a disorder (e.g., a cancer, an inflammatory condition, or a disorder associated with bone loss), as defined herein, means evaluating the subject for a change in a disease parameter, e.g., an improvement in one or more symptoms of the disease. In some embodiments, the evaluation is performed at least 1 hour, e.g., at least 2, 4, 6, 8, 12, 24, or 48 hours, or at least 1 day, 2 days, 4 days, 10 days, 13 days, 20 days or more, or at least 1 week, 2 weeks, 4 weeks, 10 weeks, 13 weeks, 20 weeks or more, after an administration. The human can be evaluated in one or more of the following periods: prior to beginning of treatment; during the treatment; or after one or more elements of the treatment have been administered. Evaluating can include evaluating the need for further treatment, e.g., evaluating whether a dosage, frequency of administration, or duration of treatment should be altered. It can also include evaluating the need to add or drop a selected therapeutic modality, e.g., adding or dropping any of the treatments for a disorder described herein.

In some embodiments, monitoring the progress and/or effectiveness of a therapeutic treatment includes monitoring the level of CD200 expression by cancer cells before and after treatment. In some embodiments, monitoring the progress and/or effectiveness of a therapeutic treatment includes monitoring the level of CD5 expression by cancer cells before and after treatment. In some embodiments, monitoring the progress and/or effectiveness of a therapeutic treatment includes monitoring the level of CD200 and CD5 expression by cancer cells before and after treatment. For example, pretreatment levels of CD200 and/or CD5 expression by cancer cells can be ascertained and, after at least one administration of the therapy, levels of CD200 and/or CD5 can again be determined. A decrease in CD200 and/or CD5 expression by cancer cells can be indicative of an effective treatment (see below). Measurement of CD200 and/or CD5 expression levels by the cancer cells can be used by the practitioner as a guide for increasing dosage amount or frequency of the therapy. It should of course be understood that CD200 and/or CD5 levels can be directly monitored or, alternatively, any marker that correlates with CD200 and/or CD5 can be monitored.

Because administration of an anti-CD200 antibody to an animal reduces the concentration of CD5$^+$ cells in the animal, it is believed to be beneficial to administer to the human an anti-CD200 antibody in an amount and with a frequency sufficient to sustain the reduced concentration of CD5$^+$ cells in a human particularly in the case of CD5$^+$ chronic lymphocytic leukemia for the reasons described above. Methods for detecting expression or a change in expression of CD5 by cells (e.g., cancer cells such as B cell CLL cells) are well known in the art (e.g., Western blot, immunohistochemistry, and flow cytometry techniques) and described herein. For example, following the administration of an anti-CD200 antibody to a human, the concentration of CD5$^+$ cancer cells in the human can be determined by flow cytometry analysis of the cancer cells present in a biological sample obtained from a patient. The concentration of CD5$^+$ cancer cells post-treatment can be compared to a control concentration (e.g., the concentration of CD5$^+$ cancer cells in the human prior to treatment with the antibody), wherein a reduction in the concentration of CD5+ cancer cells indicates that the anti-CD200 antibody has been administered to the human in an amount and with a frequency sufficient to reduce the concentration of CD5+ cells in the human and is thus therapeutically effective.

Through an iterative process, a medical practitioner can determine the appropriate dose amount, and frequency of administration of each dose, required to maintain a reduced concentration of CD5+ cancer cells in the patient. For example, a medical practitioner can administer to a cancer patient one or more (e.g., one, two, three, four, five, six, seven, eight, nine, or 10 or more or, e.g., at least three, four, five, six, seven, or eight or more) times an anti-CD200 antibody in an amount that reduces (or is at least expected to reduce) the concentration of CD5+ cancer cells. The at least two doses should be spaced apart in time by at least one (e.g., at least two, three, four, five, six, seven, eight, nine, 10, 11, 12, 13, or even 14) day(s). Biological samples (e.g., blood samples) containing cancer cells are obtained from the patient at various times, e.g., prior to the first anti-CD200 antibody administration, between the first dose and at least one additional dose, and at least one biological sample collection following the second dose. In some embodiments, biological samples may be collected at least two times between doses and/or at least one time after the final dose administered to the patient. The cancer cells in each biological sample obtained are then interrogated for relative percentage of CD5+ cancer cells to determine whether the amount and/or the frequency of administration of the anti-CD200 antibody are sufficient to maintain a reduced concentration of CD5+ cancer cells. Armed with information on CD5+ cancer cell concentration in the patient over time and the effect on the concentration of CD5+ cancer cells over time by administering the anti-CD200 antibody to the patient, a medical practitioner (and/or a computer) can determine an anti-CD200 antibody dosing schedule for the patient that is sufficient to maintain a reduced concentration of CD5+ cancer cells in the patient over the course of the treatment. As described above, the treatment can be performed in conjunction with an anti-CD20 therapy such as rituximab.

An antibody described herein (e.g., an anti-CD20 antibody or an anti-CD200 antibody) can be administered as a fixed dose, or in a milligram per kilogram (mg/kg) dose. In some embodiments, the dose can also be chosen to reduce or avoid production of antibodies or other host immune responses against one or more of the active antibodies in the composition. While in no way intended to be limiting, exemplary dosages of an antibody include, e.g., 1-100 µg/kg, 0.5-50 µg/kg, 0.1-100 µg/kg, 0.5-25 µg/kg, 1-20 µg/kg, and 1-10 µg/kg, 1-100 mg/kg, 0.5-50 mg/kg, 0.1-100 mg/kg, 0.5-25 mg/kg, 1-20 mg/kg, and 1-10 mg/kg. Exemplary dosages of an antibody described herein include, without limitation, 0.1 µg/kg, 0.5 µg/kg, 1.0 µg/kg, 2.0 µg/kg, 4 µg/kg, and 8 µg/kg, 0.1 mg/kg, 0.5 mg/kg, 1.0 mg/kg, 2.0 mg/kg, 4 mg/kg, and 8 mg/kg. Exemplary doses also include, e.g., greater than or equal to 50 mg/m$^2$, 75 mg/m$^2$, 100 mg/m$^2$, 150 mg/m$^2$, 200 mg/m$^2$, 250 mg/m$^2$, 300 mg/m$^2$, 350 mg/m$^2$, 400 mg/m$^2$, 450 mg/m$^2$, 500 mg/m$^2$, 550 mg/m$^2$, and/or 600 mg/m$^2$.

A pharmaceutical composition can include a therapeutically effective amount of an antibody described herein. Such effective amounts can be readily determined by one of ordinary skill in the art based, in part, on the effect of the administered antibody, or the combinatorial effect of the antibody and one or more additional active agents, if more than one agent is used. A therapeutically effective amount of an antibody described herein can also vary according to factors such as the disease state, age, sex, and weight of the individual, and the ability of the antibody (and one or more additional active agents) to elicit a desired response in the individual, e.g., amelioration of at least one condition parameter, e.g., amelioration of at least one symptom of the cancer and/or the presence of at least one of the immunomodulatory effect biomarkers described herein. A therapeutically effective amount is also one in which any toxic or detrimental effects of the composition are outweighed by the therapeutically beneficial effects.

Toxicity and therapeutic efficacy of such compositions can be determined by known pharmaceutical procedures in cell cultures or experimental animals (e.g., animal models of cancer or autoimmune disorders). These procedures can be used, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. An anti-CD200 antibody and/or anti-CD20 therapeutic agent (e.g., an anti-CD20 antibody) that exhibits a high therapeutic index is preferred. While compositions that exhibit toxic side effects may be used, care should be taken to design a delivery system that targets such compounds to the site of affected tissue and to minimize potential damage to normal cells and, thereby, reduce side effects.

The following examples are intended to illustrate, not limit, the invention.

EXAMPLES

Example 1

Efficacy of an Anti-CD200 Antibody in a Mouse Model of Autoimmune Hemolytic Disease Study 0 (Prevention Model).

Therapeutic anti-CD200 antibodies were tested for their ability to prevent, delay, or lessen the severity of, the production of autoantibodies associated with autoimmune hemolytic disease using a mouse model of the disease. See, e.g., Playfair and Marshall-Clarke (1973) *Nat New Biol* 243: 213-214; Naysmith et al. (1981) *Immunol Rev* 55:55-87.

To elicit in mice the production of autoantibodies that bind to mouse red blood cells (RBCs), $2\times10^8$ rat RBCs were administered intraperitoneally (i.p.) to female C57BL/6 mice once on study day 0 and then once per week thereafter for the remainder of the study. Production of anti-rat RBC alloantibodies by the immunized mice was observed by the second week of the study and production by the mice of anti-mouse RBC autoantibodies was observed by week three.

The rat RBC-immunized mice were divided into six experimental groups designated: Group 1 (six mice), Group 2 (6 mice), Group 3 (8 mice), Group 4 (7 mice), Group 5 (9 mice), and Group 6 (9 mice). One additional group—Group 7 (6 mice)—was also evaluated as a control. The Group 7 mice were neither immunized with rat RBCs nor did they receive any of the additional treatments described below.

Starting at day 0 (that is the day of the first administration of the rat RBCs), the mice of each of Groups 2 to 6 were administered a therapeutic agent or vehicle under the following schedule: for each week of the study, five doses of agent or vehicle administered as one dose per day for five consecutive days. Group 1 mice were treated with only vehicle—phosphate-buffered saline (PBS). Group 2 mice were treated under the above treatment schedule using 5 mg/kg of a Control antibody that does not bind to CD200, but possesses effector function (IgG2a). Group 3 mice were treated under the aforementioned treatment schedule with Antibody 1—an anti-CD200 antibody (IgG2a) having effector function—each dose being 5 mg/kg. Group 4 mice were treated with cyclosporine at a dose of 15 mg/kg. Group 5 mice were treated with the Control Antibody at 5 mg/kg and cyclosporine at 15 mg/kg. Group 6 mice were treated with Antibody 1 at a dose of 5 mg/kg and cyclosporine at a dose of 15 mg/kg. The antibody treatments were administered i.p. Cyclosporine was administered to the mice subcutaneously (s.c.). The Group design and treatment schedules for each group are summarized in Table 1.

TABLE 1

Group Design and Treatment Schedule for Study 0.

| Groups | N | Therapeutic Administered | Dose |
|---|---|---|---|
| Group 1 | 6 | Vehicle | N/A |
| Group 2 | 6 | Control antibody (IgG2a) that does not bind to CD200 but possesses effector function | 5 mg/kg |
| Group 3 | 8 | Antibody 1 (anti-CD200 antibody IgG2a with effector function) | 5 mg/kg |
| Group 4 | 7 | Cyclosporine | 15 mg/kg |
| Group 5 | 9 | Control antibody (IgG2a) that does not bind to CD200 but possesses effector function; and | 5 mg/kg |
| | | Cyclosporine | 15 mg/kg |
| Group 6 | 9 | Antibody 1 (anti-CD200 antibody IgG2a with effector function); and | 5 mg/kg |
| | | Cyclosporine | 15 mg/kg |
| Group 7 | 6 | Non-immunized, non-treated control group | N/A |

N refers to the number of mice in each group.
N/A = not applicable.

Figure 1:
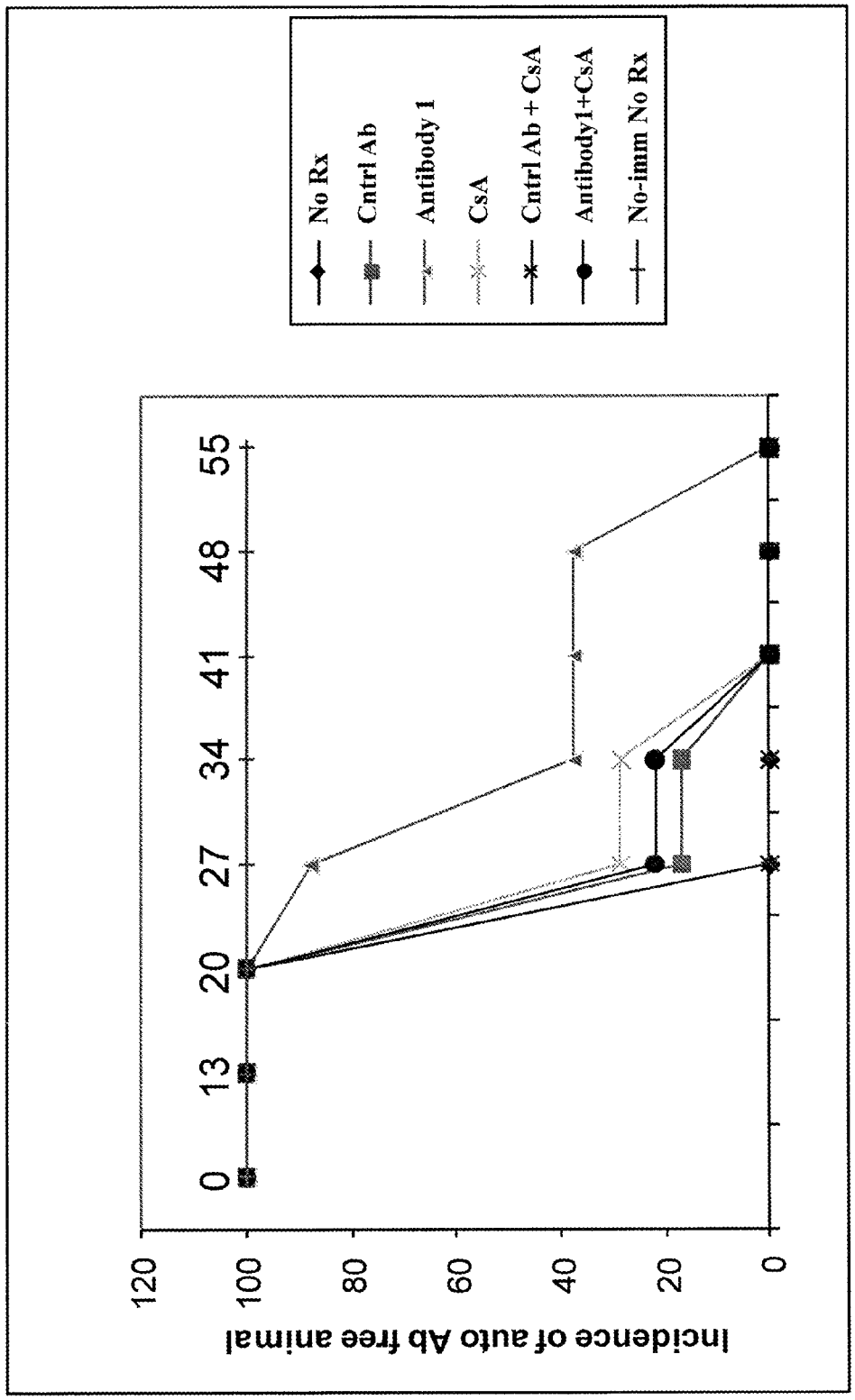
FIG. 1 is a line graph depicting the delay in anti-mouse RBC autoantibody production in mice with autoimmune hemolytic disease treated with an anti-CD200 antibody. The Y-axis represents the incidence (%) of autoantibody production in the mice in each group. The X-axis represents the time in which the presence of autoantibodies in each mouse was detected. The seven groups of mice evaluated included: mice that were immunized with rat RBCs, but not treated with an antibody (No Rx); mice that were immunized with rat RBCs and treated with a control antibody (Cntrl Ab); mice that were immunized with rat RBCs and treated with an anti-CD200 antibody (Antibody 1); mice that were immunized with rat RBCs and treated with cyclosporine (CsA); mice that were immunized with rat RBCs and treated with the control antibody and cyclosporine A (Cntrl Ab+CsA); mice that were immunized with rat RBCs and treated with an anti-CD200 antibody and cyclosporine A (Antibody 1+CsA); and mice that were neither immunized with rat RBCs nor treated with antibody or cyclosporine (No-imm No Rx).

On a weekly basis, blood was drawn from the mice of Groups 1 to 7 prior to, during, and after the above treatments to evaluate by flow cytometry whether treatment affected the titer of anti-mouse RBC autoantibodies and/or anti-rat RBC alloantibodies in the mice. To determine the relative concentration of anti-mouse autoantibodies produced in a subject mouse (e.g., a treated mouse from Group 3), whole blood obtained from the mouse was incubated with a preparation of fluorescently-labeled anti-mouse antibody to thereby detect the presence of anti-mouse RBC antibodies present on the surface of mouse RBC in the blood of the animals. The cells were washed with PBS and then subjected to flow cytometry to evaluate the relative amount of mouse anti-mouse RBCs bound to the mouse RBCs as a function of the mean fluorescence intensity. Between day 13 and 27, the concentration of anti-mouse RBC autoantibodies in the mice of Groups 1, 2, 4, 5, and 6 increased. In contrast, the concentration of anti-mouse RBC autoantibodies in the mice of Group 3 was markedly reduced as compared to the concentration of autoantibody in the other groups. In addition, the production of autoantibody by the mice in Group 3 was markedly delayed as compared to the mice in the other groups (FIG. 1). For example, 50% of mice in Groups 1, 2, 4, 5, and 6 developed autoantibodies between day 20 and 27 of the study. In contrast, autoantibody production in at least 50% of mice in Group 3 did not occur until between day 27 and day 34. These results indicate that Antibody 1, an anti-CD200 antibody, at 5 mg/kg was capable of not only reducing the concentration of anti-mouse RBC autoantibodies in a mice model of autoimmune hemolytic disease, but was also capable of delaying significantly the production of the autoantibodies in the mice.

To determine the relative concentration of alloantibodies produced in a subject mouse (e.g., a treated mouse from Group 3), serum obtained from the mouse was incubated with a sample of isolated rat RBCs for a time and under conditions sufficient for any rat RBC-specific alloantibodies present in the serum to bind to the rat RBCs. The cells were washed with PBS and then incubated with a fluorescently-labeled antibody that binds to mouse antibodies. Following an additional washing step, the cells were subjected to flow cytometry to evaluate the relative amount of mouse anti-rat RBCs bound to the rat RBCs as the mean fluorescence intensity. Sera obtained from mice of Groups 1, 2, 4, 5, and 6 contained an increasing concentration of anti-rat RBC alloantibodies over the course of the experiment. In contrast, sera obtained from the mice of Group 3 contained much less detectable anti-rat RBC autoantibodies as compared to the other Groups. These results further indicated that Antibody 1, an anti-CD200 antibody, at 5 mg/kg was capable of reducing the titer of RBC-specific alloantibodies, as well as anti-RBC autoantibodies, produced in a mouse model of autoimmune hemolytic disease.

Study 1 (Treatment Model).

Therapeutic anti-CD200 antibodies were tested for their ability to reduce the production of autoantibodies associated with autoimmune hemolytic disease using a mouse model of the disease. To elicit in mice the production of autoantibodies that bind to mouse red blood cells (RBCs), $2 \times 10^8$ rat RBCs were administered intraperitoneally (i.p.) to female C57BL/6 mice once on study day 0 and then once per week thereafter for the remainder of the study. Production of anti-rat RBC alloantibodies by the immunized mice was observed by the second week of the study and production by the mice of anti-mouse RBC autoantibodies was observed by week three.

The rat RBC-immunized mice were divided into five groups designated Group 1 (8 mice), Group 2 (8 mice), Group 3 (8 mice), Group 4 (7 mice), and Group 5 (8 mice). A sixth group of mice (designated Group 6; 6 mice) was also evaluated as a control. The Group 6 mice were neither immunized with rat RBCs nor did they receive any of the additional treatments described below.

Starting on day 112, the mice of each of Groups 1 to 5 received an additional treatment of 14 doses of a therapeutic agent or vehicle control administered under the following schedule: (i) five doses of agent or vehicle administered as one dose per day for five consecutive days; (ii) a two day break in treatment; (iii) an additional five doses of the agent or vehicle administered one dose per day for five consecutive days; another two day break in treatment; and (iv) four more doses of agent or vehicle administered one dose per day for four consecutive days. Group 1 mice were treated with only vehicle—phosphate-buffered saline (PBS). Group 2 mice were treated under the aforementioned treatment schedule with Antibody 1—an anti-CD200 antibody (IgG2a) having effector function—each dose being 5 mg/kg. Group 3 mice were treated with Antibody 1 at a dose of 1 mg/kg. Group 4 mice were treated under the above treatment schedule with Antibody 2—an anti-CD200 antibody that lacked effector function—each dose at 5 mg/kg. Group 5 mice were treated under the above treatment schedule using a dose of 5 mg/kg of a Control antibody that does not bind to CD200, but possesses effector function (IgG2a). The Group design and treatment schedules for each group are summarized in Table 2.

TABLE 2

Group Design and Treatment Schedule for Study 1.

| Groups | N | Therapeutic Administered | Dose |
|---|---|---|---|
| Group 1 | 8 | Vehicle | N/A |
| Group 2 | 8 | Antibody 1 (anti-CD200 antibody IgG2a with effector function) | 5 mg/kg |

TABLE 2-continued

Group Design and Treatment Schedule for Study 1.

| Groups | N | Therapeutic Administered | Dose |
|---|---|---|---|
| Group 3 | 8 | Antibody 1 (anti-CD200 antibody IgG2a with effector function) | 1 mg/kg |
| Group 4 | 7 | Antibody 2 (anti-CD200 antibody that does not possess effector function) | 5 mg/kg |
| Group 5 | 8 | Control antibody (IgG2a) that does not bind to CD200 but possesses effector function | 5 mg/kg |
| Group 6 | 6 | Non-immunized, non-treated control group | N/A |

N refers to the number of mice in each group.
N/A = not applicable.

On a weekly basis, blood was drawn from the mice of Groups 1 to 6 prior to, during, and after the above treatments to evaluate by flow cytometry whether treatment affected the titer of anti-mouse RBC autoantibodies and/or anti-rat RBC alloantibodies in the mice. Between day 133 and 137 of the study, the mice were sacrificed and their spleens harvested. To determine the relative concentration of alloantibodies produced in a subject mouse (e.g., a treated mouse from Group 2), serum obtained from the mouse (e.g., at day 133) was contacted to a sample of isolated rat RBCs for a time and under conditions sufficient for any rat RBC-specific alloantibodies present in the serum to bind to the rat RBCs. The cells were washed with PBS and then incubated with a fluorescently-labeled antibody that binds to mouse antibodies. Following an additional washing step, the cells were subjected to flow cytometry to evaluate the relative amount of mouse anti-rat RBCs bound to the rat RBCs as the mean fluorescence intensity. The inventors observed that the post-treatment sera obtained from mice of Groups 1, 3, 4, and 5 contained an increased concentration of anti-rat RBC alloantibodies as compared to the corresponding sera obtained from the mice prior to treatment. In contrast, sera obtained from the mice of Group 2 post-treatment contained less detectable anti-rat RBC alloantibodies as compared to the corresponding sera obtained from the mice prior to treatment. These results indicated that Antibody 1, an anti-CD200 antibody, at 5 mg/kg was capable of reducing the production of RBC-specific antibodies in a mouse model of autoimmune hemolytic disease.

The inventors subsequently observed that Antibody 2 had a significantly shorter half-life in the treated mice as compared to the half-life of Antibody 1. Thus the results observed with Antibody 2 in Study 1 and in other studies described herein may not fully reflect the true efficacy of the Antibody 2 in the autoimmune hemolytic disease model nor the immunodulatory effect of the antibody in animals.

Study 2 (Prevention Model).

Therapeutic anti-CD200 antibodies were tested for their ability to prevent, delay, or lessen the severity of, the production of autoantibodies associated with autoimmune hemolytic disease using the above-described mouse model of the disease.

To elicit in mice the production of autoantibodies that bind to mouse red blood cells (RBCs), rat RBCs were administered intraperitoneally (i.p.) to female BALB/c mice once on study day 0 and then once per week thereafter for the remainder of the study. As described above, production of anti-rat RBC alloantibodies by the immunized mice was observed by the second week of the study and production by the mice of anti-mouse RBC autoantibodies was observed by week three.

The rat RBC-immunized mice were divided into five groups designated Group 1 (8 mice), Group 2 (8 mice), Group 3 (8 mice), Group 4 (8 mice), and Group 5 (8 mice). A sixth group of mice (designated Group 6; 6 mice) was also evaluated as a control. The Group 6 mice were neither immunized with rat RBCs nor did they receive any of the additional treatments described below.

Starting at day 0 (that is the day of the first administration of the rat RBCs), the mice of each of Groups 1 to 5 were administered a therapeutic agent or vehicle under the following schedule: for each week of the study, five doses of agent or vehicle administered as one dose per day for five consecutive days. Group 1 mice were treated with only vehicle— phosphate-buffered saline (PBS). Group 2 mice were treated under the aforementioned treatment schedule with Antibody 1—an anti-CD200 antibody (IgG2a) having effector function—each dose being 5 mg/kg. Group 3 mice were treated with Antibody 1 at a dose of 1 mg/kg. Group 4 mice were treated under the above treatment schedule with Antibody 2—an anti-CD200 antibody that lacked effector function— each dose at 5 mg/kg. Group 5 mice were treated under the above treatment schedule using 5 mg/kg of a Control antibody that does not bind to CD200, but possesses effector function (IgG2a). The Group design and treatment schedules for each group are summarized in Table 3.

TABLE 3

Group Design and Treatment Schedule for Study 2.

| Groups | N | Therapeutic Administered | Dose |
|---|---|---|---|
| Group 1 | 8 | Vehicle | N/A |
| Group 2 | 8 | Antibody 1 (anti-CD200 antibody IgG2a with effector function) | 5 mg/kg |
| Group 3 | 8 | Antibody 1 (anti-CD200 antibody IgG2a with effector function) | 1 mg/kg |
| Group 4 | 8 | Antibody 2 (anti-CD200 antibody that does not possess effector function) | 5 mg/kg |
| Group 5 | 8 | Control antibody (IgG2a) that does not bind to CD200 but possesses effector function | 5 mg/kg |
| Group 6 | 6 | Non-immunized, non-treated control group | N/A |

N refers to the number of mice in each group.
N/A = not applicable.

Figure 2:
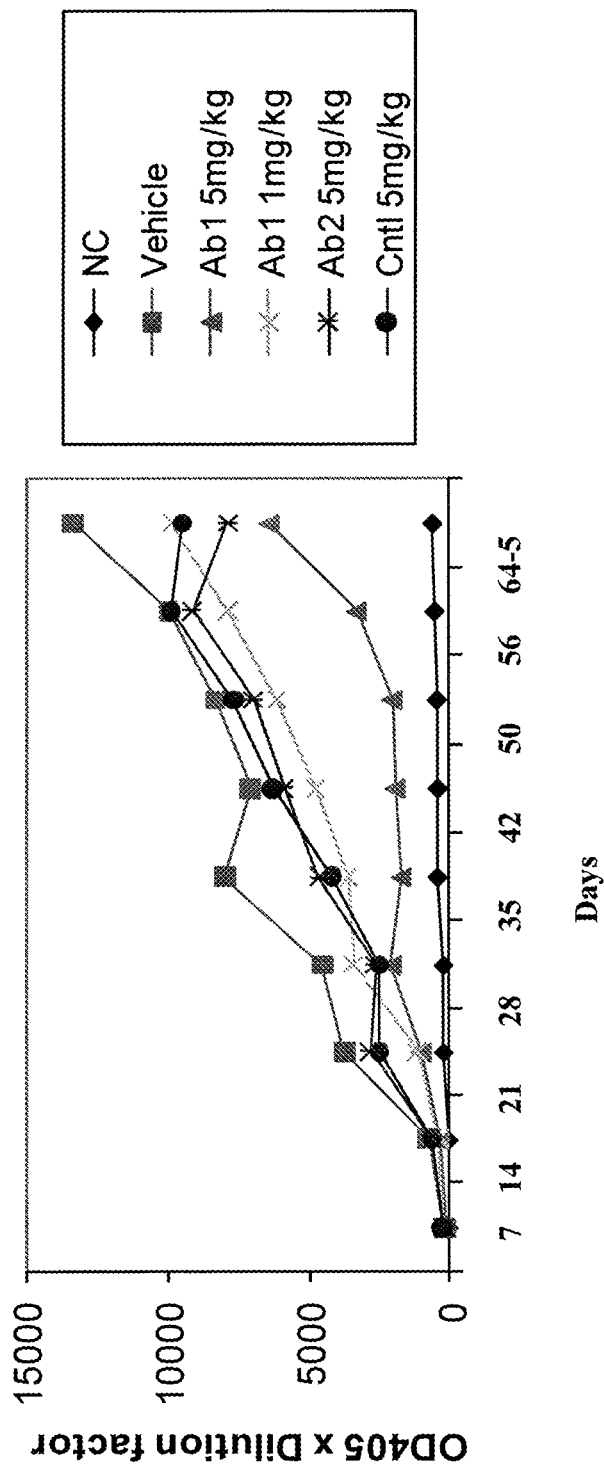
FIG. 2 is a line graph depicting the effect of an anti-CD200 antibody on anti-RBC antibody titer in a mouse model of autoimmune hemolytic disease. C57BL/6 mice were administered $2 \times 10^8$ rat RBCs intraperitoneally (i.p.) once on study day 0 and then once per week thereafter for the remainder of the study. The rat RBC-immunized mice were then treated with an anti-CD200 antibody that possessed effector function (Antibody 1; Ab 1) at 5 mg/kg or 1 mg/kg; an anti-CD200 antibody that did not possess effector function (Antibody 2; Ab 2) at 5 mg/kg; or a control antibody (Cntl) at 5 mg/kg. A group of mice was also treated with vehicle only. A final group of mice received no immunization or antibody treatment (NC). The Y-axis depicts the relative fluorescence intensity reflected as the OD405× serum dilution factor and the X-axis represents the number of days following the start of the study.

On a weekly basis, blood was drawn from the mice of Groups 1 to 6 prior to, during, and after the above treatments to evaluate by flow cytometry whether treatment affected the titer of anti-mouse RBC autoantibodies and/or anti-rat RBC alloantibodies in the mice. On day 64 or 65 of the study, the mice were sacrificed and their spleens harvested. (Four mice in each group were sacrificed on day 64 and the other four mice in each group were sacrificed on day 65.) To determine the relative concentration of alloantibodies produced in a subject mouse (e.g., a treated mouse from Group 3), serum obtained from the mouse was contacted to a sample of isolated rat RBCs for a time and under conditions sufficient for any rat RBC-specific alloantibodies present in the serum to bind to the rat RBCs. The cells were washed with PBS and then incubated with a fluorescently-labeled antibody that binds to mouse antibodies. Following an additional washing step, the cells were subjected to flow cytometry to evaluate the relative amount of mouse anti-rat RBCs bound to the rat RBCs as the mean fluorescence intensity. As shown in FIG. 2, sera obtained from mice of Groups 1, 3, 4, and 5 contained an increasing concentration of anti-rat RBC alloantibodies over the course of the experiment. In contrast, sera obtained from the mice of Group 2 post-treatment contained much less detectable anti-rat RBC alloantibodies as compared to the other Groups. These results further indicated that Antibody 1, an anti-CD200 antibody, at 5 mg/kg was capable of reducing the titer of RBC-specific alloantibodies produced in a mouse model of autoimmune hemolytic disease.

Study 3 (Treatment Model).

Therapeutic anti-CD200 antibodies were tested for their ability to treat autoimmune hemolytic disease using a mouse model of the disease. To elicit in mice the production of autoantibodies that bind to mouse red blood cells (RBCs), rat RBCs were administered intraperitoneally (i.p.) to female C57BL/6 mice once on study day 0 and then once per week thereafter for the remainder of the study. As described above, production of anti-rat RBC alloantibodies by the immunized mice was observed by the second week of the study and production by the mice of anti-mouse RBC autoantibodies was observed by week three. The rat RBC-immunized mice were divided into three groups designated Group 1 (6 mice), Group 2 (3 mice), and Group 3 (5 mice).

Starting on day 86, the mice of each of Groups 1 to 3 received an additional treatment of 10 doses of a therapeutic agent or vehicle control administered under the following schedule: (i) five doses of agent or vehicle administered as one dose per day for five consecutive days; (ii) a two day break in treatment; and (iii) an additional five doses of the agent or vehicle administered one dose per day for five consecutive days. Group 1 mice were treated under the aforementioned treatment schedule with Antibody 1—an anti-CD200 antibody (IgG2a) having effector function—each dose being 5 mg/kg. Group 2 mice were treated with Antibody 1 at a dose of 1 mg/kg. Group 3 mice were treated under the above treatment schedule with Antibody 2—an anti-CD200 antibody that lacked effector function—each dose at 5 mg/kg. The Group design and treatment schedules for each group are summarized in Table 4.

TABLE 4

Group Design and Treatment Schedule for Study 3.

| Groups | N | Therapeutic Administered | Dose |
|---|---|---|---|
| Group 1 | 6 | Antibody 1 (anti-CD200 antibody IgG2a with effector function) | 5 mg/kg |
| Group 2 | 3 | Antibody 1 (anti-CD200 antibody IgG2a with effector function) | 1 mg/kg |
| Group 3 | 5 | Control Antibody | 5 mg/kg |
| Group 4 | 3 | Non-immunized, non-treated control group | N/A |

N refers to the number of mice in each group.
N/A = not applicable.

At the conclusion of the study, the mice were sacrificed and their spleens harvested. To determine whether administration of Antibody 1 to the mice affected activation of splenocytes by RBC, in addition to affecting the production of anti-RBC antibodies in the mice, splenocyte activation in the presence of RBCs was evaluated using an in vitro proliferation assay. Briefly, isolated splenocytes were cultured with one of three different antigens—mouse RBCs, rat RBCs, or bovine serum albumin (control)—or with media alone. Following contact of the splenocytes with the antigens, $^3$H-thymidine was added to the splenocyte culture media for approximately 16 hours. The media was removed and the cells harvested. The relative activation of the splenocytes by the antigens was then measured as a function of the amount of $^3$H-thymidine incorporated into the DNA of the splenocytes.

As shown in FIG. 3, splenocytes from Group 2 and 3 mice exhibited a robust proliferative response following contact with rat RBCs. In contrast, splenocytes from Group 1 mice proliferated very little in the presence of rat RBCs indicating that administration of an anti-CD200 antibody at 5 mg/kg was capable of inhibiting the activation of splenocytes by rat RBCs in a mouse model of autoimmune hemolytic disease.

Study 4 (Treatment Model).

As described above, to elicit in mice the production of autoantibodies that bind to mouse red blood cells (RBCs), rat RBCs were administered intraperitoneally (i.p.) to female C57BL/6 mice once on study day 0 and then once per week thereafter for the remainder of the study.

The rat RBC-immunized mice were divided into seven (7) groups designated Group 1, Group 2, Group 3, Group 4, Group 5, Group 6, and Group 7. An eighth group of mice (designated Group 8) was also evaluated as a control. The Group 8 mice were neither immunized with rat RBCs nor did they receive any of the additional treatments described below. Ten mice were in each group.

Starting on day 21, the mice of each of Groups 1 to 7 received an additional treatment of one or more therapeutic agents or vehicle control administered under the following schedule: for each week of the study, five doses of one or more agents or vehicle administered as one dose per day for five consecutive days. Group 1 mice were treated with only vehicle—phosphate-buffered saline (PBS). Group 2 mice were treated under the above treatment schedule using a dose of 5 mg/kg of a Control antibody that does not bind to CD200, but possesses effector function (IgG2a). Group 3 mice were treated under the aforementioned treatment schedule with Antibody 1—an anti-CD200 antibody (IgG2a) having effector function—each dose being 5 mg/kg. Group 4 mice were treated under the above schedule with 15 mg/kg cyclosporine. Group 5 mice were treated under the above dosing schedule with both the Control antibody (at 5 mg/kg) and cyclosporine (at 15 mg/kg). Group 6 mice were treated under the above dosing schedule with both Antibody 1 (at 5 mg/kg) and cyclosporine (at 15 mg/kg). Group 7 mice were treated under the above dosing schedule with both Antibody 1 (at 1 mg/kg) and cyclosporine (at 15 mg/kg). The Group design and treatment schedules for each group are summarized in Table 5.

TABLE 5

Group Design and Treatment Schedule for Study 4.

| Groups | N | Therapeutic Administered | Dose |
|---|---|---|---|
| Group 1 | 10 | Vehicle | N/A |
| Group 2 | 10 | Control antibody (IgG2a) that does not bind to CD200 but possesses effector function | 5 mg/kg |
| Group 3 | 10 | Antibody 1 (anti-CD200 antibody IgG2a with effector function) | 5 mg/kg |
| Group 4 | 10 | Cyclosporine | 15 mg/kg |
| Group 5 | 10 | Control antibody; and cyclosporine | 5 mg/kg 15 mg/kg |
| Group 6 | 10 | Antibody 1; and cyclosporine | 5 mg/kg 15 mg/kg |
| Group 7 | 10 | Antibody 1; and cyclosporine | 1 mg/kg 15 mg/kg |
| Group 8 | 10 | Non-immunized, non-treated control group | N/A |

N refers to the number of mice in each group.
N/A = not applicable.

On a weekly basis, blood was drawn from the mice of Groups 1 to 8 prior to, during, and after the above treatments to evaluate by flow cytometry whether treatment affected the titer of anti-mouse RBC autoantibodies and/or anti-rat RBC alloantibodies in the mice. On day 37 of the study, the mice were sacrificed and their spleens harvested. Bone marrow cells were also obtained from the two mouse femur and tibia bones. The spleen and bone marrow cells were subjected to flow cytometry as described below (Example 2).

A reduced concentration of anti-rat RBC alloantibodies was present in post-treatment sera obtained from mice of Groups 3 and 4 as compared to the corresponding pre-treatment sera. The post-treatment reduction in anti-rat RBC alloantibodies was even greater in the mice of Groups 6 and 7, indicating that cyclosporine and Antibody 1 have a synergistic effect on reducing alloantibody production in the mice. These results even further indicated that an anti-CD200 antibody was capable of reducing the titer of RBC-specific antibodies produced in a mouse model of autoimmune hemolytic disease and that an anti-CD200 antibody is useful for treating the disease.

Example 2

Figure 4:
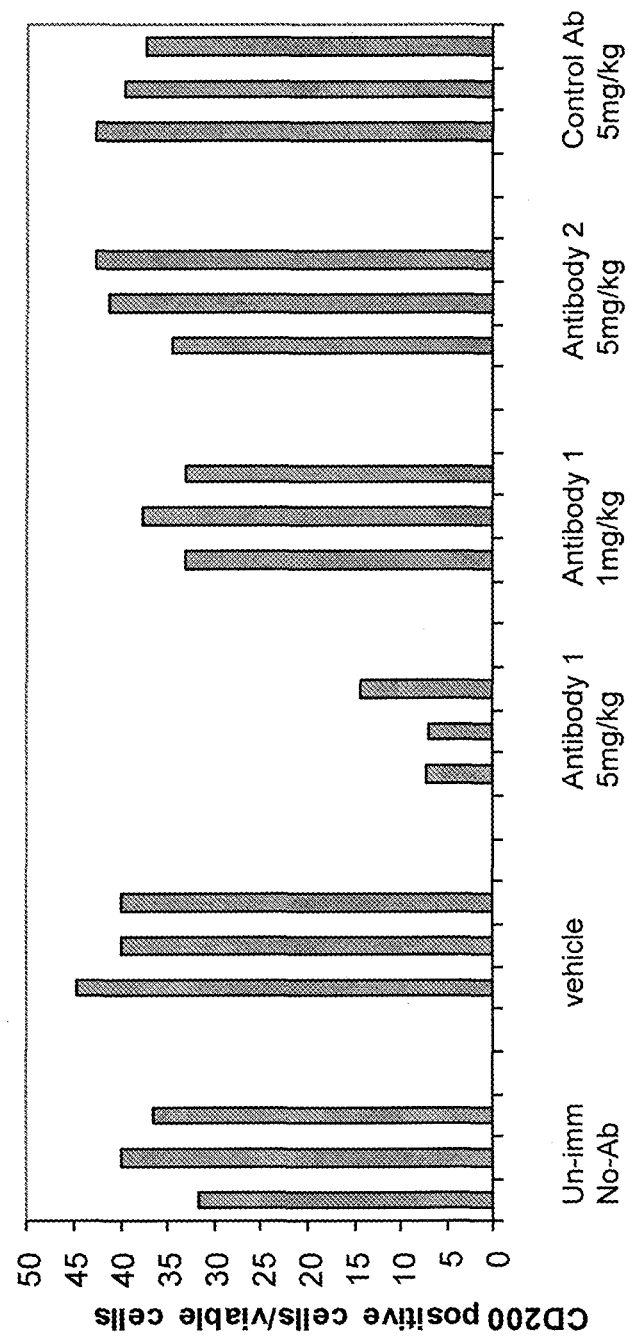
FIG. 4 is a bar graph depicting the reduction in CD200$^+$ splenocytes in mice treated with an anti-CD200 antibody. C57BL/6 mice were administered $2 \times 10^8$ rat RBCs intraperitoneally (i.p.) once on study day 0 and then once per week thereafter for the remainder of the study. The rat RBC-immunized mice were then treated with an anti-CD200 antibody that possessed effector function (Antibody 1; Ab 1) at 5 mg/kg or 1 mg/kg; an anti-CD200 antibody that did not possess effector function (Antibody 2; Ab 2) at 5 mg/kg; or a control antibody (Cntl) at 5 mg/kg. A group of mice was also treated with vehicle only. A final group of mice received no immunization or antibody treatment (Un-imm, No-Ab). The Y-axis represents the percentage of CD200$^+$ cells in the total population of viable splenocytes. The X-axis represents individual mice, three (3) depicted in each group.

Administration of an Anti-CD200 Antibody to Mice Affects the Concentration of Splenocyte and Bone Marrow Cell Populations in the Mice Splenocytes obtained from the mice of Study 1 were evaluated to determine the percentage of cells that express CD200. Cells were harvested from the spleens of the mice and incubated with a composition of biotin-labeled anti-CD200 antibodies (polyclonal) for an amount of time and under conditions sufficient to allow for binding of the antibodies to CD200, if present on the cells. The polyclonal antibody preparation was used to prevent or lessen any masking effect due to the presence of residual therapeutic anti-CD200 antibody (e.g., Antibody 1 or Antibody 2) on the cells. The cells were washed and incubated with a fluorescently-labeled streptavidin moiety. Following an additional washing step, the cells were then subjected to flow cytometry. As shown in FIG. 4, there was a marked reduction in the concentration of $CD200^+$ splenocytes in mice treated with 14, 5 mg/kg doses of Antibody 1 as compared to the concentration of $CD200^+$ splenocytes in mice treated with vehicle, the Control antibody, or Antibody 2.

Splenocytes harvested from the spleens of the mice of Study 2 were also subjected to staining and flow cytometry analysis as described above. There was a marked reduction in the concentration of $CD200^+$ splenocytes in mice chronically treated with 5 mg/kg of Antibody 1, as compared to the concentration of $CD200^+$ splenocytes in mice treated with vehicle or the Control antibody. There was also no change in the concentration of $CD200^+$ splenocytes in the Group 3 mice treated with 1 mg/kg dose of Antibody 1 and Group 4 mice trated with 5 mg/kg Antibody 2.

Splenocytes harvested from the spleens of the mice of Study 4 were also subjected to staining and flow cytometry analysis as described above. There was a marked reduction in the concentration of $CD200^+$ splenocytes in mice treated with 5 mg/kg of Antibody 1 with or without cyclosporine, as compared to the concentration of $CD200^+$ splenocytes in mice treated with vehicle, the Control antibody, cyclosporine alone, or a combination of the Control antibody and cyclosporine. There was also no change in the concentration of $CD200^+$ splenocytes in the Group 7 mice treated with a combination schedule of cyclosporine and a 1 mg/kg dose of Antibody 1. An analysis of the mean fluorescence intensity (MFI) of the $CD200^+$ splenocytes from each mouse (which is a measure of the relative expression level of CD200 by each $CD200^+$ splenocyte) was also performed. The MFI of $CD200^+$ splenocytes from Groups 4 and 7 was markedly reduced as compared to the MFI of $CD200^+$ splenocytes in the remaining Groups (save Group 8). This indicated that not only does administration of Antibody 1 to the mice reduce the total number of $CD200^+$ splenocytes, but the remaining cells that do express $CD200^+$ in Antibody 1-treated mice express CD200 at much lower levels.

Taken together, these results confirm that administration of an anti-CD200 antibody to an animal reduces the concentration of $CD200^+$ splenocytes in the animal. The results also indicate that the anti-CD200 antibody-mediated reduction in $CD200^+$ splenocytes is not positively or negatively affected by cyclosporine.

The inventors also further examined the effect of anti-CD200 antibodies on: (i) the concentration of particular $CD200^+$ lymphocyte subsets of splenocytes from the mice of Study 4 and (ii) the concentration of particular $CD200^+$ subsets of bone marrow-derived cells from the mice of Study 4.

Concentration of Splenic Lymphocyte Subsets in the Mice of Study 4

$CD3^+/CD200^+$ Lymphocyte Subset.

A sample of splenocytes from each of the mice of Study 4 was incubated with the polyclonal anti-CD200 antibody preparation and a detectably-labeled antibody that binds to CD3 to thereby identify the proportion of $CD3^+/CD200^+$ cells in the spleens of mice from Groups 1 to 8. The $CD3^+$ population of cells includes T cells such as $CD4^+$ and $CD8^+$ T cells. The labeled cells were subjected to flow cytometry. There was a marked reduction in the concentration of $CD3^+/CD200^+$ splenocytes in mice chronically treated with 5 mg/kg of Antibody 1 with or without cyclosporine, as compared to the concentration of $CD3^+/CD200^+$ splenocytes in mice treated with vehicle, the Control antibody, cyclosporine alone, or a combination of the Control antibody and cyclosporine. There was also no significant change in the concentration of $CD3^+/CD200^+$ splenocytes in the Group 7 mice treated with a combination schedule of cyclosporine and a 1 mg/kg dose of Antibody 1.

$CD5^+/CD200^+$ Lymphocyte Subset.

A sample of splenocytes from each of the mice of Study 4 was incubated with the polyclonal anti-CD200 antibody preparation and a detectably-labeled antibody that binds to CD5 to thereby identify the proportion of $CD5^+/CD200^+$ cells in the spleens of mice from Groups 1 to 8. The $CD5^+$ population of cells includes T cells as well as B cells (the B1 cell population). The labeled cells were subjected to flow cytometry. There was a marked reduction in the concentration of $CD5^+/CD200^+$ splenocytes in mice chronically treated with 5 mg/kg of Antibody 1 with or without cyclosporine, as compared to the concentration of $CD5^+/CD200^+$ splenocytes in mice treated with vehicle, the Control antibody, cyclosporine alone, or a combination of the Control antibody and cyclosporine. There was also no significant change in the concentration of $CD5^+/CD200^+$ splenocytes in the Group 7 mice treated with a combination schedule of cyclosporine and a 1 mg/kg dose of Antibody 1.

$CD19^+/CD200^+$ Lymphocyte Subset.

A sample of splenocytes from each of the mice of Study 4 was incubated with the polyclonal anti-CD200 antibody preparation and a detectably-labeled antibody that binds to CD19 to thereby identify the proportion of $CD19^+/CD200^+$ cells in the spleens of mice from Groups 1 to 8. The $CD19^+$ population of cells includes B cells. The labeled cells were subjected to flow cytometry. Like $CD5^+/CD200^+$ cells and $CD3^+/CD200^+$ cells, there was also a marked reduction in the concentration of $CD19^+/CD200^+$ splenocytes in mice chronically treated with 5 mg/kg of Antibody 1 with or without cyclosporine, as compared to the concentration of CD19+/CD200+ splenocytes in mice treated with vehicle, the Control antibody, cyclosporine alone, or a combination of the Control antibody and cyclosporine. There was also no significant change in the concentration of CD19+/CD200+ splenocytes in the Group 7 mice treated with a combination schedule of cyclosporine and a 1 mg/kg dose of Antibody 1.

CD138+/CD200+ Lymphocyte Subset.

A sample of splenocytes from each of the mice of Study 4 was incubated with the polyclonal anti-CD200 antibody preparation and a detectably-labeled antibody that binds to CD138 to thereby identify the proportion of CD138+/CD200+ cells in the spleens of mice from Groups 1 to 8. The CD138+ population of cells includes plasma cells. The labeled cells were subjected to flow cytometry. There was a marked reduction in the concentration of CD138+/CD200+ splenocytes in mice chronically treated with 5 mg/kg of Antibody 1 with or without cyclosporine, as compared to the concentration of CD138+/CD200+ splenocytes in mice treated with vehicle, the Control antibody, cyclosporine alone, or a combination of the Control antibody and cyclosporine. There was also no significant change in the concentration of CD138+/CD200+ splenocytes in the Group 7 mice treated with a combination schedule of cyclosporine and a 1 mg/kg dose of Antibody 1.

F4/80+ Lymphocyte Subset.

F4/80 is 125 kDa transmembrane protein present on the cell-surface of mature mouse macrophages. To determine whether administration of an anti-CD200 antibody affects the concentration of resident macrophages in spleen, a sample of splenocytes from each mouse of Study 4 was incubated with a detectably-labeled antibody that binds to F4/80. The labeled cells were subjected to flow cytometry to thereby identify the proportion of F4/80+ cells in the spleens of mice from Groups 1 to 8. The concentration of F4/80+ splenocytes increased in mice treated with 5 mg/kg of Antibody 1 (10 doses) with or without cyclosporine, as compared to the concentration of F4/80+ splenocytes in mice treated with vehicle, the Control antibody, cyclosporine alone, or a combination of the Control antibody and cyclosporine. There was also no significant change in the concentration of F4/80+ splenocytes in the Group 7 mice treated with a combination schedule of cyclosporine and a 1 mg/kg dose of Antibody 1.

Taken together, these results indicate that administration of an anti-CD200 antibody reduces a variety of CD200+ splenocyte subsets, but increases certain macrophage subsets, in the treated animals.

Concentration of Bone Marrow Cell Subsets in the Mice of Study 4

CD34+/CD200+ Bone Marrow Cell Subset.

A sample of bone marrow cells from each of the mice was incubated with the polyclonal anti-CD200 antibody preparation and a detectably-labeled antibody that binds to CD34 to thereby identify the proportion of CD34+/CD200+ cells in the bone marrow of mice from Groups 1 to 8. The CD34+ cells include a population of hematopoietic stem cells (HSCs). The labeled cells were subjected to flow cytometry also selecting for those cells that are lineage low ($Lin^{-/Low}$). There was a marked reduction in the concentration of CD34+/CD200+ bone marrow cells in mice treated with 5 mg/kg of Antibody 1 (10 doses) with or without cyclosporine, as compared to the concentration of CD34+/CD200+ bone marrow cells in mice treated with vehicle, the Control antibody, cyclosporine alone, or a combination of the Control antibody and cyclosporine. There was also no significant change in the concentration of CD34+/CD200+ bone marrow cells in the Group 7 mice treated with a combination schedule of cyclosporine and a 1 mg/kg dose of Antibody 1.

Sca-1+/CD200+ Bone Marrow Cell Subsets.

A sample of bone marrow cells from each of the mice was incubated with the polyclonal anti-CD200 antibody preparation and a detectably-labeled antibody that binds to Sca-1 to thereby identify the proportion of Sca-1+/CD200+ cells in the bone marrow of mice from Groups 1 to 8. The Sca-1+ cells include a population of HSCs and mesenchymal stem cells (MSCs). The labeled cells were subjected to flow cytometry also selecting for those cells that are lineage low ($Lin^{-/Low}$). There was a marked reduction in the concentration of Sca-1+/CD200+ bone marrow cells in mice treated with 5 mg/kg of Antibody 1 (10 doses) with or without cyclosporine, as compared to the concentration of Sca-1+/CD200+ bone marrow cells in mice treated with vehicle, the Control antibody, cyclosporine alone, or a combination of the Control antibody and cyclosporine. There was also no significant change in the concentration of Sca-1+/CD200+ bone marrow cells in the Group 7 mice treated with a combination schedule of cyclosporine and a 1 mg/kg dose of Antibody 1.

Sca-1+/CD34+ Bone Marrow Cell Subsets.

A sample of bone marrow cells from each of the mice was incubated with a first detectably-labeled antibody that binds to CD34 and a second detectably-labeled antibody that binds to Sca-1 to thereby identify the proportion of Sca-1+/CD34+ cells in the bone marrow of mice from Groups 1 to 8. The labeled cells were subjected to flow cytometry also selecting for those cells that are lineage low ($Lin^{-/Low}$). The Sca-1+/CD34+/Lin– cells include a population of MSCs. There was a marked reduction in the concentration of Sca-1+/CD34+ bone marrow cells in mice treated with 5 mg/kg of Antibody 1 (10 doses) with or without cyclosporine, as compared to the concentration of Sca-1+/CD34+ bone marrow cells in mice treated with vehicle, the Control antibody, cyclosporine alone, or a combination of the Control antibody and cyclosporine. There was also no significant change in the concentration of Sca-1+/CD34+ bone marrow cells in the Group 7 mice treated with a combination schedule of cyclosporine and a 1 mg/kg dose of Antibody 1.

c-kit+/CD200+ Bone Marrow Cell Subsets.

A sample of bone marrow cells from each of the mice was incubated with the polyclonal anti-CD200 antibody preparation and a detectably-labeled antibody that binds to c-kit to thereby identify the proportion of c-kit+/CD200+ cells in the bone marrow of mice from Groups 1 to 8. The c-kit+ cells include a population of HSCs and MSCs. The labeled cells were subjected to flow cytometry also selecting for those cells that are lineage low ($Lin^{-/Low}$). There was a marked reduction in the concentration of c-kit+/CD200+ bone marrow cells in mice chronically treated with 5 mg/kg of Antibody 1 with or without cyclosporine, as compared to the concentration of c-kit+/CD200+ bone marrow cells in mice treated with vehicle, the Control antibody, cyclosporine alone, or a combination of the Control antibody and cyclosporine. There was also no significant change in the concentration of c-kit+/CD200+ bone marrow cells in the Group 7 mice treated with a combination schedule of cyclosporine and a 1 mg/kg dose of Antibody 1.

CD200+/CD200R+ Bone Marrow Cell Subset.

A sample of bone marrow cells from each of the mice was incubated with the polyclonal anti-CD200 antibody preparation and a detectably-labeled antibody that binds to CD200R to thereby identify the proportion of CD200+/CD200R+ cells in the bone marrow of mice from Groups 1 to 8. The labeled cells were subjected to flow cytometry. There was a marked reduction in the concentration of CD200+/CD200R+ bone marrow cells in mice chronically treated with 5 mg/kg of Antibody 1 with or without cyclosporine, as compared to the concentration of CD200+/CD200R+ bone marrow cells in mice treated with vehicle, the Control antibody, cyclosporine alone, or a combination of the Control antibody and cyclosporine. There was also no significant change in the concentration of CD200+/CD200R+ bone marrow cells in the Group 7 mice treated with a combination schedule of cyclosporine and a 1 mg/kg dose of Antibody 1.

Example 3

Recovery of Bone Marrow Cell and CD200+ Splenocyte Subsets after Withdrawal of Anti-CD200 Therapy Study 5 (Treatment Model).

The therapeutic anti-CD200 antibodies were again tested for their ability modulate the concentration of specific subset populations of splenocytes and bone marrow cells. The antibodies were administered to the mice in the context of a mouse model of autoimmune hemolytic disease. As described above, to elicit in mice the production of autoantibodies that bind to mouse red blood cells (RBCs), $2\times10^8$ rat RBCs were administered intraperitoneally (i.p.) to female BALB/c mice once on study day 0 and then once per week thereafter for the remainder of the study. Production of anti-rat RBC alloantibodies by the immunized mice was observed by the second week of the study and production by the mice of anti-mouse RBC autoantibodies was observed by week three.

The rat RBC-immunized mice were divided into five groups designated Group 2 (20 mice), Group 3 (20 mice), Group 4 (20 mice), Group 5 (15 mice), and Group 6 (15 mice). A sixth group of mice (designated Group 1; 20 mice) was also evaluated as a control. The Group 1 mice were neither immunized with rat RBCs nor did they receive any of the additional treatments described below.

Starting on day 21, the mice of each of Groups 2 to 6 received an additional treatment of 10 doses of a therapeutic agent or vehicle control administered under the following schedule: (i) five doses of agent or vehicle administered as one dose per day for five consecutive days; (ii) a two day break in treatment; and (iii) an additional five doses of the agent or vehicle administered one dose per day for five consecutive days. Group 6 mice were treated with only vehicle—phosphate-buffered saline (PBS). Group 2 mice were treated under the aforementioned treatment schedule with Antibody 1—an anti-CD200 antibody (IgG2a) having effector function—each dose being 5 mg/kg. Group 3 mice were treated under the above treatment schedule with Antibody 2—an anti-CD200 antibody that lacked effector function—each dose at 5 mg/kg. Group 4 mice were treated under the above treatment schedule using a dose of 5 mg/kg of a Control antibody that does not bind to CD200, but possesses effector function (IgG2a). Group 5 mice were treated under the above treatment schedule using a dose of 5 mg/kg of a Control antibody that does not bind to CD200 and does not possess effector function. The Group design and treatment schedules for each group are summarized in Table 6.

TABLE 6

Group Design and Treatment Schedule for Study 5.

| Groups | N | Therapeutic Administered | Dose |
|---|---|---|---|
| Group 1 | 20 | Non-immunized, non-treated control group | N/A |
| Group 2 | 20 | Antibody 1 (anti-CD200 antibody IgG2a with effector function) | 5 mg/kg |
| Group 3 | 20 | Antibody 2 (anti-CD200 antibody that does not possess effector function) | 5 mg/kg |
| Group 4 | 20 | Control antibody (IgG2a) that does not bind to CD200 but possesses effector function | 5 mg/kg |
| Group 5 | 15 | Control antibody (IgG2a) that does not bind to CD200 and does not possess effector function | 5 mg/kg |
| Group 6 | 15 | Vehicle | N/A |

N refers to the number of mice in each group.
N/A = not applicable.

On a weekly basis, blood was drawn from the mice of Groups 1 to 6 prior to, during, and after the above treatments to evaluate by flow cytometry whether treatment affected the titer of anti-mouse RBC autoantibodies and/or anti-rat RBC alloantibodies in the mice. On day 35 of the study, three of the mice in each group were sacrificed and their spleens harvested. Bone marrow was also isolated from the femurs and tibias of each mouse. As described above, the cells were labeled with detectably-labeled antibodies (e.g., the polyclonal anti-CD200 antibody preparation and an additional fluorescently-labeled antibody) and subjected to flow cytometry. A summary of the results are shown below in Table 7.

TABLE 7

Effect of Anti-CD200 Antibodies on Splenocyte and Bone Marrow Cell Subsets at day 35

| Tissue Type | Cell Subset/ Expression Profile | Reduction (R) or Increase (I) in Group 2 Mice** | Reduction (R) or Increase (I) in Group 3 Mice** |
|---|---|---|---|
| Spleen | CD200+ | R | R |
| Spleen | CD3+/CD200+ | R | — |
| Spleen | CD5+/CD200+ | R | — |
| Spleen | CD19+/CD200+ | R | — |
| Spleen | CD45R+/CD200+ | R | — |
| Spleen | CD138+/CD200+ (Gated on CD45R+ cells) | R | R |
| Spleen | CD200+ (Gated on CD45R+ cells) | R | R* |
| Bone Marrow | CD200+ | R | — |
| Bone Marrow | CDIgk+/CD200+ | R | — |
| Bone Marrow | CD200+ (Gated on CD45R+ cells) | R | — |
| Bone Marrow | CD200+ (Gated on CD138+/CD45R− cells) | R | — |
| Bone Marrow | c-kit+/CD200+ (Gated on Lin− cells) | R | R |

*indicates that the reduction in concentration of a particular cell subset in mice treated with Antibody 2 is not as profound as the reduction observed in the same cell subset in mice treated with Antibody 1.
**indicates that the reduction or increase in the concentration of a particular cell subset is relative the concentration of the particular subset in vehicle treated mice (Group 6) and the corresponding isotype control. Thus, the reduction of CD200+ splenocytes observed in mice of Group 2 mice is relative to the concentration of CD200+ splenocytes in Group 6 mice and Group 4 mice.
"—" indicates that no difference in the levels was observed between Antibody 2 and its corresponding Control antibody.

From day 35 to day 91, the remaining mice in each group received additional RBC immunizations but no treatments with the antibodies, the purpose being to determine if the populations of splenocytes and bone marrow cells would recover over time. Three mice in each group were sacrificed at day 91 and their spleens and bone marrow harvested as described above. Flow cytometry analysis was performed on the isolated cells to determine whether particular population subsets of splenocytes and bone marrow cells, which were reduced at day 35, recovered by day 91. Each of the cell populations recovered fully by day 91, indicating that the modulatory effects of the anti-CD200 antibody on the concentration of bone marrow cell and splenocyte subsets is reversible upon withdrawal of the antibody.

While the present disclosure has been described with reference to the specific embodiments thereof, it should be understood by those skilled in the art that various changes may be made and equivalents may be substituted without departing from the true spirit and scope of the disclosure. In addition, many modifications may be made to adapt a particular situation, material, composition of matter, process, process step or steps, to the objective, spirit and scope of the present disclosure. All such modifications are intended to be within the scope of the disclosure.

What is claimed is:

1. A method for treating a human afflicted with a cancer, the method comprising:
   (a) identifying a human having a cancer that is resistant to anti-CD20 antibody therapy, and
   (b) administering to the human an anti-CD200 antibody, or a CD200-binding fragment thereof, in an amount that is sufficient to treat the cancer.

2. The method of claim 1, wherein the cancer comprises cancer cells that express CD5.

3. The method of claim 2, further comprising identifying the cancer as comprising cells that express CD5.

4. The method of claim 1, wherein the cancer is a liquid tumor.

5. The method of claim 4, wherein the liquid tumor is a chronic lymphocytic leukemia or multiple myeloma.

6. The method of claim 5, wherein the chronic lymphocytic leukemia is a B cell chronic lymphocytic leukemia.

7. The method of claim 1, wherein the anti-CD200 antibody, or CD200-binding fragment thereof, inhibits the interaction between CD200 and CD200R.

8. The method of claim 1, wherein the anti-CD200 antibody, or CD200-binding fragment thereof, comprises a heavy chain CDR1 (HCDR1) comprising the amino acid sequence: GFTFSGFAMS (SEQ ID NO:4); a heavy chain CDR2 (HCDR2) comprising the amino acid sequence: SISSGGT-TYYLDSVKG (SEQ ID NO:5); a heavy chain CDR3 (HCDR3) comprising the amino acid sequence: GNYYS-GTSYDY (SEQ ID NO:6); a light chain CDR1 (LCDR1) comprising the amino acid sequence: RASESVDSYGNS-FMH (SEQ ID NO:7); a light chain CDR2 (LCDR2) comprising the amino acid sequence: RASNLES (SEQ ID NO:8); and a light chain CDR3 (LCDR3) comprising the amino acid sequence: QQSNEDPRT (SEQ ID NO:9).

9. The method of claim 1, wherein the anti-CD200 antibody, or CD200-binding fragment thereof, is murine, chimeric, humanized, or fully human.

10. The method of claim 1, wherein the CD200-binding fragment is selected from the group consisting of a Fab fragment, a F(ab')$_2$ fragment, a Fab' fragment, an scFv fragment, a minibody, a diabody, or a triabody.

11. The method of claim 1, wherein the cancer comprises cancer cells having reduced CD20 expression, relative to the expression of CD20 by normal cells of the same histological type as the cells from which the cancer cells are derived.

* * * * *

```
SEQUENCE LISTING

<160> NUMBER OF SEQ ID NOS: 42

<210> SEQ ID NO 1
<211> LENGTH: 269
<212> TYPE: PRT
<213> ORGANISM: Homo sapiens

<400> SEQUENCE: 1

Met Glu Arg Leu Val Ile Arg Met Pro Phe Ser His Leu Ser Thr Tyr
1               5                   10                  15

Ser Leu Val Trp Val Met Ala Ala Val Leu Cys Thr Ala Gln Val
            20                  25                  30

Gln Val Val Thr Gln Asp Glu Arg Glu Gln Leu Tyr Thr Pro Ala Ser
            35                  40                  45

Leu Lys Cys Ser Leu Gln Asn Ala Gln Glu Ala Leu Ile Val Thr Trp
    50                  55                  60

Gln Lys Lys Lys Ala Val Ser Pro Glu Asn Met Val Thr Phe Ser Glu
65                  70                  75                  80

Asn His Gly Val Val Ile Gln Pro Ala Tyr Lys Asp Lys Ile Asn Ile
                85                  90                  95

Thr Gln Leu Gly Leu Gln Asn Ser Thr Ile Thr Phe Trp Asn Ile Thr
            100                 105                 110

Leu Glu Asp Glu Gly Cys Tyr Met Cys Leu Phe Asn Thr Phe Gly Phe
        115                 120                 125

Gly Lys Ile Ser Gly Thr Ala Cys Leu Thr Val Tyr Val Gln Pro Ile
    130                 135                 140

Val Ser Leu His Tyr Lys Phe Ser Glu Asp His Leu Asn Ile Thr Cys
145                 150                 155                 160

Ser Ala Thr Ala Arg Pro Ala Pro Met Val Phe Trp Lys Val Pro Arg
                165                 170                 175

Ser Gly Ile Glu Asn Ser Thr Val Thr Leu Ser His Pro Asn Gly Thr
            180                 185                 190

Thr Ser Val Thr Ser Ile Leu His Ile Lys Asp Pro Lys Asn Gln Val
        195                 200                 205

Gly Lys Glu Val Ile Cys Gln Val Leu His Leu Gly Thr Val Thr Asp
    210                 215                 220

Phe Lys Gln Thr Val Asn Lys Gly Tyr Trp Phe Ser Val Pro Leu Leu
225                 230                 235                 240

Leu Ser Ile Val Ser Leu Val Ile Leu Leu Val Leu Ile Ser Ile Leu
                245                 250                 255

Leu Tyr Trp Lys Arg His Arg Asn Gln Asp Arg Glu Pro
            260                 265

<210> SEQ ID NO 2
<211> LENGTH: 294
<212> TYPE: PRT
```

<213> ORGANISM: Homo sapiens

<400> SEQUENCE: 2

```
Met Glu Arg Leu Thr Leu Thr Arg Thr Ile Gly Gly Pro Leu Leu Thr
1               5                   10                  15

Ala Thr Leu Leu Gly Lys Thr Thr Ile Asn Asp Tyr Gln Val Ile Arg
            20                  25                  30

Met Pro Phe Ser His Leu Ser Thr Tyr Ser Leu Val Trp Val Met Ala
        35                  40                  45

Ala Val Val Leu Cys Thr Ala Gln Val Gln Val Val Thr Gln Asp Glu
    50                  55                  60

Arg Glu Gln Leu Tyr Thr Pro Ala Ser Leu Lys Cys Ser Leu Gln Asn
65                  70                  75                  80

Ala Gln Glu Ala Leu Ile Val Thr Trp Gln Lys Lys Lys Ala Val Ser
                85                  90                  95

Pro Glu Asn Met Val Thr Phe Ser Glu Asn His Gly Val Val Ile Gln
            100                 105                 110

Pro Ala Tyr Lys Asp Lys Ile Asn Ile Thr Gln Leu Gly Leu Gln Asn
        115                 120                 125

Ser Thr Ile Thr Phe Trp Asn Ile Thr Leu Glu Asp Glu Gly Cys Tyr
    130                 135                 140

Met Cys Leu Phe Asn Thr Phe Gly Phe Gly Lys Ile Ser Gly Thr Ala
145                 150                 155                 160

Cys Leu Thr Val Tyr Val Gln Pro Ile Val Ser Leu His Tyr Lys Phe
                165                 170                 175

Ser Glu Asp His Leu Asn Ile Thr Cys Ser Ala Thr Ala Arg Pro Ala
            180                 185                 190

Pro Met Val Phe Trp Lys Val Pro Arg Ser Gly Ile Glu Asn Ser Thr
        195                 200                 205

Val Thr Leu Ser His Pro Asn Gly Thr Thr Ser Val Thr Ser Ile Leu
    210                 215                 220

His Ile Lys Asp Pro Lys Asn Gln Val Gly Lys Glu Val Ile Cys Gln
225                 230                 235                 240

Val Leu His Leu Gly Thr Val Thr Asp Phe Lys Gln Thr Val Asn Lys
                245                 250                 255

Gly Tyr Trp Phe Ser Val Pro Leu Leu Leu Ser Ile Val Ser Leu Val
            260                 265                 270

Ile Leu Leu Val Leu Ile Ser Ile Leu Leu Tyr Trp Lys Arg His Arg
        275                 280                 285

Asn Gln Asp Arg Glu Pro
        290
```

<210> SEQ ID NO 3
<211> LENGTH: 274
<212> TYPE: PRT
<213> ORGANISM: Homo sapiens

<400> SEQUENCE: 3

```
Val Ile Arg Met Pro Phe Ser His Leu Ser Thr Tyr Ser Leu Val Trp
1               5                   10                  15

Val Met Ala Ala Val Val Leu Cys Thr Ala Gln Val Gln Val Val Thr
            20                  25                  30

Gln Asp Glu Arg Glu Gln Leu Tyr Thr Thr Ala Ser Leu Lys Cys Ser
        35                  40                  45

Leu Gln Asn Ala Gln Glu Ala Leu Ile Val Thr Trp Gln Lys Lys Lys
```

```
            50                  55                  60
Ala Val Ser Pro Glu Asn Met Val Thr Phe Ser Glu Asn His Gly Val
 65                  70                  75                  80

Val Ile Gln Pro Ala Tyr Lys Asp Lys Ile Asn Ile Thr Gln Leu Gly
                 85                  90                  95

Leu Gln Asn Ser Thr Ile Thr Phe Trp Asn Ile Thr Leu Glu Asp Glu
            100                 105                 110

Gly Cys Tyr Met Cys Leu Phe Asn Thr Phe Gly Phe Gly Lys Ile Ser
            115                 120                 125

Gly Thr Ala Cys Leu Thr Val Tyr Val Gln Pro Ile Val Ser Leu His
        130                 135                 140

Tyr Lys Phe Ser Glu Asp His Leu Asn Ile Thr Cys Ser Ala Thr Ala
145                 150                 155                 160

Arg Pro Ala Pro Met Val Phe Trp Lys Val Pro Arg Ser Gly Ile Glu
                165                 170                 175

Asn Ser Thr Val Thr Leu Ser His Pro Asn Gly Thr Thr Ser Val Thr
            180                 185                 190

Ser Ile Leu His Ile Lys Asp Pro Lys Asn Gln Val Gly Lys Glu Val
        195                 200                 205

Ile Cys Gln Val Leu His Leu Gly Thr Val Thr Asp Phe Lys Gln Thr
210                 215                 220

Val Asn Lys Gly Tyr Trp Phe Ser Val Pro Leu Leu Leu Ser Ile Val
225                 230                 235                 240

Ser Leu Val Ile Leu Leu Val Leu Ile Ser Ile Leu Leu Tyr Trp Lys
                245                 250                 255

Arg His Arg Asn Gln Asp Arg Gly Glu Leu Ser Gln Gly Val Gln Lys
            260                 265                 270

Met Thr

<210> SEQ ID NO 4
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Gly Phe Thr Phe Ser Gly Phe Ala Met Ser
 1               5                  10

<210> SEQ ID NO 5
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Ser Ile Ser Ser Gly Gly Thr Thr Tyr Tyr Leu Asp Ser Val Lys Gly
 1               5                  10                  15

<210> SEQ ID NO 6
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 6

Gly Asn Tyr Tyr Ser Gly Thr Ser Tyr Asp Tyr
1               5                   10

<210> SEQ ID NO 7
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Arg Ala Ser Glu Ser Val Asp Ser Tyr Gly Asn Ser Phe Met His
1               5                   10                  15

<210> SEQ ID NO 8
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Arg Ala Ser Asn Leu Glu Ser
1               5

<210> SEQ ID NO 9
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Gln Gln Ser Asn Glu Asp Pro Arg Thr
1               5

<210> SEQ ID NO 10
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Gly Phe Asn Ile Lys Asp Tyr Tyr Met His
1               5                   10

<210> SEQ ID NO 11
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Trp Ile Asp Pro Glu Asn Gly Asp Thr Lys Tyr Ala Pro Lys Phe Gln
1               5                   10                  15

Gly
```

```
<210> SEQ ID NO 12
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Lys Asn Tyr Tyr Val Ser Asn Tyr Asn Phe Phe Asp Val
1               5                   10

<210> SEQ ID NO 13
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Ser Ala Ser Ser Ser Val Arg Tyr Met Tyr
1               5                   10

<210> SEQ ID NO 14
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Asp Thr Ser Lys Leu Ala Ser
1               5

<210> SEQ ID NO 15
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Phe Gln Gly Ser Gly Tyr Pro Leu Thr
1               5

<210> SEQ ID NO 16
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Gly Phe Asn Ile Lys Asp Tyr Tyr Ile His
1               5                   10

<210> SEQ ID NO 17
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17
```

```
Trp Ile Asp Pro Glu Ile Gly Ala Thr Lys Tyr Val Pro Lys Phe Gln
1               5                   10                  15

Gly

<210> SEQ ID NO 18
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Leu Tyr Gly Asn Tyr Asp Arg Tyr Tyr Ala Met Asp Tyr
1               5                   10

<210> SEQ ID NO 19
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Lys Ala Ser Gln Asn Val Arg Thr Ala Val Ala
1               5                   10

<210> SEQ ID NO 20
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Leu Ala Ser Asn Arg His Thr
1               5

<210> SEQ ID NO 21
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Leu Gln His Trp Asn Tyr Pro Leu Thr
1               5

<210> SEQ ID NO 22
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Gly Tyr Ser Phe Thr Asp Tyr Ile Ile Leu
1               5                   10

<210> SEQ ID NO 23
<211> LENGTH: 17
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

His Ile Asp Pro Tyr Tyr Gly Ser Ser Asn Tyr Asn Leu Lys Phe Lys
1               5                   10                  15
Gly

<210> SEQ ID NO 24
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Ser Lys Arg Asp Tyr Phe Asp Tyr
1               5

<210> SEQ ID NO 25
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Lys Ala Ser Gln Asp Ile Asn Ser Tyr Leu Ser
1               5                   10

<210> SEQ ID NO 26
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Arg Ala Asn Arg Leu Val Asp
1               5

<210> SEQ ID NO 27
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Leu Gln Tyr Asp Glu Phe Pro Tyr Thr
1               5

<210> SEQ ID NO 28
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28
```

```
Gly Tyr Thr Phe Thr Glu Tyr Thr Met His
1               5                   10

<210> SEQ ID NO 29
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Gly Val Asn Pro Asn Gly Gly Ala Leu Tyr Asn Gln Lys Phe Lys
1               5                   10                  15

Gly

<210> SEQ ID NO 30
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Arg Ser Asn Tyr Arg Tyr Asp Asp Ala Met Asp Tyr
1               5                   10

<210> SEQ ID NO 31
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Lys Ser Ser Gln Ser Leu Leu Asp Ile Asp Glu Lys Thr Tyr Leu Asn
1               5                   10                  15

<210> SEQ ID NO 32
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Leu Val Ser Lys Leu Asp Ser
1               5

<210> SEQ ID NO 33
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Trp Gln Gly Thr His Phe Pro Gln Thr
1               5

<210> SEQ ID NO 34
<211> LENGTH: 10
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Ala Phe Asn Ile Lys Asp His Tyr Met His
1               5                   10

<210> SEQ ID NO 35
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Trp Ile Asp Pro Glu Ser Gly Asp Thr Glu Tyr Ala Pro Lys Phe Gln
1               5                   10                  15

Gly

<210> SEQ ID NO 36
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Phe Asn Gly Tyr Gln Ala Leu Asp Gln
1               5

<210> SEQ ID NO 37
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Thr Ala Ser Ser Ser Val Ser Ser Ser Tyr Leu His
1               5                   10

<210> SEQ ID NO 38
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Ser Thr Ser Asn Leu Ala Ser
1               5

<210> SEQ ID NO 39
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39
```

Arg Gln Tyr His Arg Ser Pro Pro Ile Phe Thr
1               5                   10

<210> SEQ ID NO 40
<211> LENGTH: 297
<212> TYPE: PRT
<213> ORGANISM: Homo sapiens

<400> SEQUENCE: 40

Met Thr Thr Pro Arg Asn Ser Val Asn Gly Thr Phe Pro Ala Glu Pro
1               5                   10                  15

Met Lys Gly Pro Ile Ala Met Gln Ser Gly Pro Lys Pro Leu Phe Arg
            20                  25                  30

Arg Met Ser Ser Leu Val Gly Pro Thr Gln Ser Phe Phe Met Arg Glu
        35                  40                  45

Ser Lys Thr Leu Gly Ala Val Gln Ile Met Asn Gly Leu Phe His Ile
    50                  55                  60

Ala Leu Gly Gly Leu Leu Met Ile Pro Ala Gly Ile Tyr Ala Pro Ile
65                  70                  75                  80

Cys Val Thr Val Trp Tyr Pro Leu Trp Gly Gly Ile Met Tyr Ile Ile
                85                  90                  95

Ser Gly Ser Leu Leu Ala Ala Thr Glu Lys Asn Ser Arg Lys Cys Leu
            100                 105                 110

Val Lys Gly Lys Met Ile Met Asn Ser Leu Ser Leu Phe Ala Ala Ile
        115                 120                 125

Ser Gly Met Ile Leu Ser Ile Met Asp Ile Leu Asn Ile Lys Ile Ser
    130                 135                 140

His Phe Leu Lys Met Glu Ser Leu Asn Phe Ile Arg Ala His Thr Pro
145                 150                 155                 160

Tyr Ile Asn Ile Tyr Asn Cys Glu Pro Ala Asn Pro Ser Glu Lys Asn
                165                 170                 175

Ser Pro Ser Thr Gln Tyr Cys Tyr Ser Ile Gln Ser Leu Phe Leu Gly
            180                 185                 190

Ile Leu Ser Val Met Leu Ile Phe Ala Phe Phe Gln Glu Leu Val Ile
        195                 200                 205

Ala Gly Ile Val Glu Asn Glu Trp Lys Arg Thr Cys Ser Arg Pro Lys
    210                 215                 220

Ser Asn Ile Val Leu Leu Ser Ala Glu Glu Lys Lys Glu Gln Thr Ile
225                 230                 235                 240

Glu Ile Lys Glu Glu Val Val Gly Leu Thr Glu Thr Ser Ser Gln Pro
                245                 250                 255

Lys Asn Glu Glu Asp Ile Glu Ile Ile Pro Ile Gln Glu Glu Glu Glu
            260                 265                 270

Glu Glu Thr Glu Thr Asn Phe Pro Glu Pro Pro Gln Asp Gln Glu Ser
        275                 280                 285

Ser Pro Ile Glu Asn Asp Ser Ser Pro
    290                 295

<210> SEQ ID NO 41
<211> LENGTH: 9
<212> TYPE: PRT
<213> ORGANISM: Homo sapiens

<400> SEQUENCE: 41

Ile Pro Ala Gly Ile Tyr Ala Pro Ile
1               5

```
<210> SEQ ID NO 42
<211> LENGTH: 47
<212> TYPE: PRT
<213> ORGANISM: Homo sapiens

<400> SEQUENCE: 42

Asn Ile Lys Ile Ser His Phe Leu Lys Met Glu Ser Leu Asn Phe Ile
1               5                   10                  15

Arg Ala His Thr Pro Tyr Ile Asn Ile Tyr Asn Cys Glu Pro Ala Asn
            20                  25                  30

Pro Ser Glu Lys Asn Ser Pro Ser Thr Gln Tyr Cys Tyr Ser Ile
        35                  40                  45
```